US008551536B2

(12) United States Patent
Gladwin et al.

(10) Patent No.: US 8,551,536 B2
(45) Date of Patent: Oct. 8, 2013

(54) NITRITE AND NITRITE-METHEME THERAPY TO DETOXIFY STROMA-FREE HEMOGLOBIN BASED BLOOD SUBSTITUTES

(75) Inventors: Mark T. Gladwin, Pittsburg, PA (US); Daniel B. Kim-Shapiro, Winston-Salem, NC (US); Rakesh P. Patel, Hoover, AL (US); Jeffrey Kerby, Birmingham, AL (US)

(73) Assignees: The United States of America as represented by the Secretary of the Department of Health and Human Services, Washington, DC (US); University of Alabama at Birmingham, Birmingham, AL (US); Wake Forest University, Winston-Salem, NC (US)

( * ) Notice: Subject to any disclaimer, the term of this patent is extended or adjusted under 35 U.S.C. 154(b) by 633 days.

(21) Appl. No.: 12/675,347

(22) PCT Filed: Aug. 29, 2008

(86) PCT No.: PCT/US2008/074856
§ 371 (c)(1),
(2), (4) Date: Feb. 25, 2010

(87) PCT Pub. No.: WO2009/029836
PCT Pub. Date: Mar. 5, 2009

(65) Prior Publication Data
US 2010/0247681 A1    Sep. 30, 2010

Related U.S. Application Data

(60) Provisional application No. 60/969,530, filed on Aug. 31, 2007.

(51) Int. Cl.
*A01N 35/10* (2006.01)
*C07K 14/00* (2006.01)

(52) U.S. Cl.
USPC .......................................... 424/718; 530/385

(58) Field of Classification Search
None
See application file for complete search history.

(56) References Cited

U.S. PATENT DOCUMENTS

| | | | |
|---|---|---|---|
| 6,187,744 B1 | 2/2001 | Rooney | |
| 6,197,745 B1 | 3/2001 | Stamler | |
| 6,291,424 B1 | 9/2001 | Stamler et al. | |
| 6,583,113 B2 | 6/2003 | Stamler et al. | |
| 6,627,738 B2 | 9/2003 | Stamler et al. | |
| 6,884,773 B1 | 4/2005 | Stamler et al. | |
| 7,033,999 B2 | 4/2006 | Stamler et al. | |
| 7,202,340 B2 | 4/2007 | Stamler et al. | |
| 2001/0034323 A1 | 10/2001 | Rooney | |
| 2002/0037839 A1 | 3/2002 | Stamler et al. | |

2006/0252671 A1    11/2006  Stamler et al.

FOREIGN PATENT DOCUMENTS

| | | |
|---|---|---|
| WO | WO 96/30006 | 10/1996 |
| WO | WO 96/34974 | 11/1996 |
| WO | WO 97/10265 | 3/1997 |
| WO | WO 03/102575 A1 | 12/2003 |
| WO | WO 2004/054433 A2 | 7/2004 |
| WO | WO 2006/096774 A2 | 9/2006 |
| WO | WO 2006/113540 A2 | 10/2006 |

OTHER PUBLICATIONS

Basu et al., "Catalytic generation of $N_2O_3$ by the concerted nitrite reductase and anhydrase activity of hemoglobin," *Nat Chem Biol* 3:785-794, 2007.
Bryan et al., "Bound NO in human red blood cells: fact or artifact?" *Nitric Oxide-Biol Ch* 10:221-228, 2004.
Bryan et al., "Nitrite is a signaling molecule and regulator of gene expression in mammalian tissues," *Nature Chemical Biology* 1:290-297, 2005.
Doherty et al., "Rate of reaction with nitric oxide determines the hypertensive effect of cell-free hemoglobin," *Nat Biotechnol* 16:672-676, 1998.
Dou et al., "Myoglobin as a model system for designing heme protein based blood substitutes," *Biophys Chem* 98:127-148, 2002.
Gladwin et al., "The biochemistry of nitric oxide, nitrite, and hemoglobin: role in blood flow regulation," *Free Radic Biol Med* 36:707-717, 2004.
Hess et al., "Systemic and pulmonary hypertension after resuscitation with cell-free hemoglobin," *J Appl Physiol* 74:1769-1778, 1993.
Hess et al., "Increased vascular resistance with hemoglobin-based oxygen carriers," *Artif Cells Blood Substit Immobil Biotechnol* 22:361-372, 1994.
Kim-Shapiro, "Hemoglobin-nitric oxide cooperativity: is NO the third respiratory ligand?" *Free Radic. Biol. Med.* 36:402-412, 2004.
Ali et al., "A Method to Attenuate Pneumoperitoneum-Induced Reductions in Splanchnic Blood Flow," *Annals of Surgery* 241(2):256-261, 2005.
Angelo et al., "An S-nitrosothiol (SNO) synthase function of hemoglobin that utilizes nitrite as a substrate," *PNAS* 103(22): 8366-8371, 2006.
Cosby et al., "Nitrite reduction to nitric oxide by deoxyhemoglobin vasodilates the human circulation," *Nat. Med.* 9:1498-1505, 2003.
Crawford et al., "Hypoxia, red blood cells, and nitrite regulate NO-dependent hypoxic vasodilation," *Blood* 107(2):566-574, 2006.
Duranski et al., "Cytoprotective effects of nitrite during in vivo ischemia-reperfusion of the heart and liver," *Journal of Clinical Investigation* 115(5):1232-1240, 2005.
Gladwin & Kim-Shapiro, "The functional nitrite reductase activity of the heme-globins," *Blood* 112(7):2636-2647, 2008.

(Continued)

*Primary Examiner* — Marsha Tsay
(74) *Attorney, Agent, or Firm* — Klarquist Sparkman, LLP

(57) ABSTRACT

This disclosure relates to methods of using nitrite to detoxify stroma-free hemoglobin based blood substitutes. In particular, methods are described for using a blood substitute comprised of about equimolar amounts of nitrite and hemoglobin (e.g., nitrite-metHb) to treat, prevent, or ameliorate diseases of the blood in a subject, or as a blood replacement in a subject.

19 Claims, 40 Drawing Sheets

(56) References Cited

OTHER PUBLICATIONS

Gladwin et al., "Role of circulating nitrite and S-nitrosohemoglobin in the regulation of regional blood flow in humans," *PNAS USA* 97:11482-11487, 2000.

Gladwin et al., "S-Nitrosohemoglobin is unstable in the reductive erythrocyte environment and lacks $O_2$/NO-linked allosteric function," *J. Biol. Chem.* 277:27818-27828, 2002.

Gladwin et al., "Pulmonary hypertension as a risk factor for death in patients with sickle cell disease," *N Engl J Med* 350(9):886-895, 2004.

Gladwin et al., "The emerging biology of the nitrite anion," *Nature Chemical Biology* 1(6):308-314, 2005.

Gladwin, "Evidence Mounts that Nitrite Contributes to Hypoxic Vasodilation in the Human Circulation," *Circulation* 117:594-597, 2008.

Gonzalez et al., "Nitrite Anion Provides Potent Cytoprotective and Antiapoptotic Effects as Adjunctive Therapy to Reperfusion for Acute Myocardial Infarction," *Circulation* 117:2986-2994, 2008.

Gow & Stamler, "Reactions between nitric oxide and haemoglobin under physiological conditions," *Nature* 391:169-173, 1998.

Gow et al., "The oxyhemoglobin reaction of nitric oxide," *PNAS* 96:9027-9032, 1999.

Herold & Rock, "Reaction so deoxy-, oxy-, and methemoglobin with nitrogen monoxide. Mechanistic studies of the S-nitrosothiol formation under different mixing conditions," *J. Biol. Chem.* 278:6623-6634, 2003.

Huang et al., "The reaction between nitrite and deoxyhemoglobin. Reassessment of reaction kinetics and stoichiometry," *J. Biol. Chem.* 280:31126-31131, 2005.

Huang, et al., "Enzymatic function of hemoglobin as a nitrite reductase that produces NO under allosteric control," *J. Clin. Invest.* 115(8):2099-2107, 2005.

Huang et al., "Lack of allosterically controlled intramolecular transfer of nitric oxide from the heme to cysteine in the beta subunit of hemoglobin," *Blood* 107(7):2602-2604, 2006.

Ignarro et al., "Endothelium-derived relaxing factor produced and released from artery and vein is nitric oxide," *Proc. Natl. Acad. Sci. U.S.A.* 84:9265-9269, 1987.

Isbell et al., "Hemoglobin oxygen fractional saturation regulates nitrite-dependent vasodilation of aortic ring bioassays," *Am. J. Physiol. Heart Circ. Physiol.* 293:H2565-H2572, 2007.

Kim-Shapiro et al., "Unraveling the Reactions of Nitric Oxide, Nitrite, and Hemoglobin in Physiology and Therapeutics," *Arterioscler. Thromb. Vasc. Biol.* 26:697-705, 2006.

Lauer et al., "Plasma nitrite rather than nitrate reflects regional endothelial nitric oxide synthase activity but lacks intrinsic vasodilator action," *Proc. Natl. Acad. Sci. USA* 98(22):12814-12819, 2001.

Luchsinger et al., "Routes to S-nitroso-hemoglobin formation with redox and preferential reactivity in the beta subunits," *Proc. Natl. Acad. Sci. USA* 100:461-466, 2003.

Luchsinger et al., "Assessments of the chemistry and vasodilatory activity of nitrite with hemoglobin under physiologically relevant conditions," *Journal of Inorganic Biochemistry* 99(4):912-921, 2005.

McMahon et al., "A nitric oxide processing defect of red blood cells created by hypoxia: Deficiency of S-nitrosohemoglobin in pulmonary hypertension," *PNAS* 102(41):14801-14806, 2005.

Minneci et al., "Nitrite reductase activity of hemoglobin as a systemic nitric oxide generator mechanism to detoxify plasma hemoglobin produced during hemolysis," *Am J Physiol Heart Circ Physiol* 295:H743-H754, 2008.

Rooney et al., "Hemodilution with oxyhemoglobin. Mechanism of oxygen delivery and its superaugmentation with a nitric oxide donor (sodium nitroprusside)." *Anesthesiology* 79(1):60-72, 1993.

Shiva et al., "Deoxymyoglobin is a nitrite reductase that generates nitric oxide and regulates mitochondrial respiration," *Circ. Res.* 100:654-661, 2007.

Winslow, "Red Cell Substitutes," *Seminars in Hematology* 44:51-59, 2007.

International Search Report from PCT/US2008/074856, dated Mar. 3, 2009.

Written Opinion of the international Searching Authority from PCT/US2008/074856, dated Mar. 3, 2009.

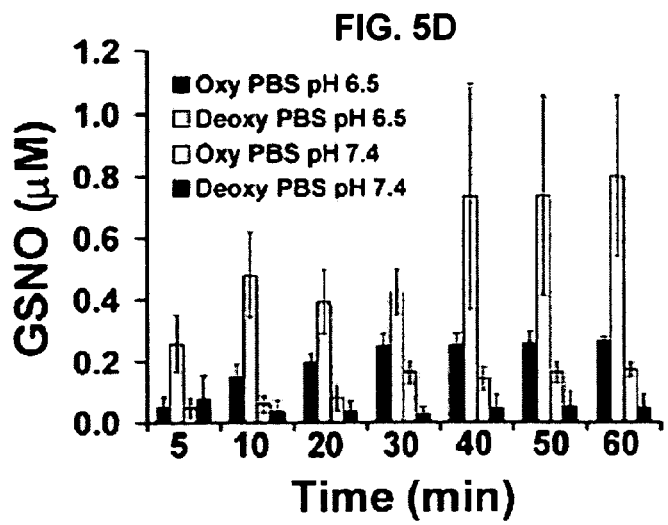
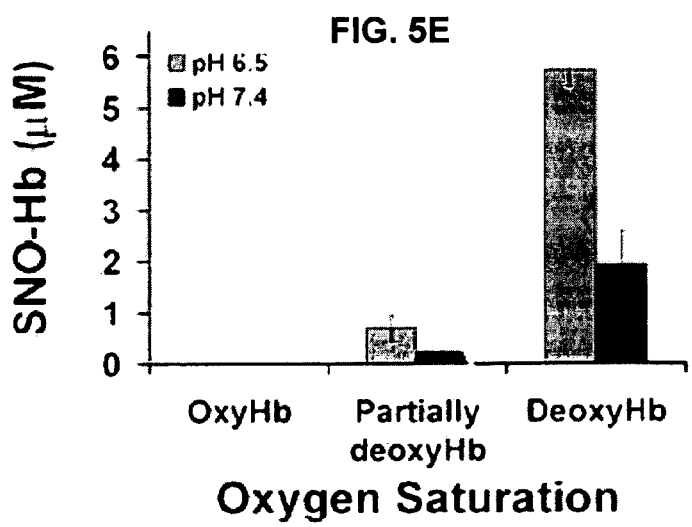
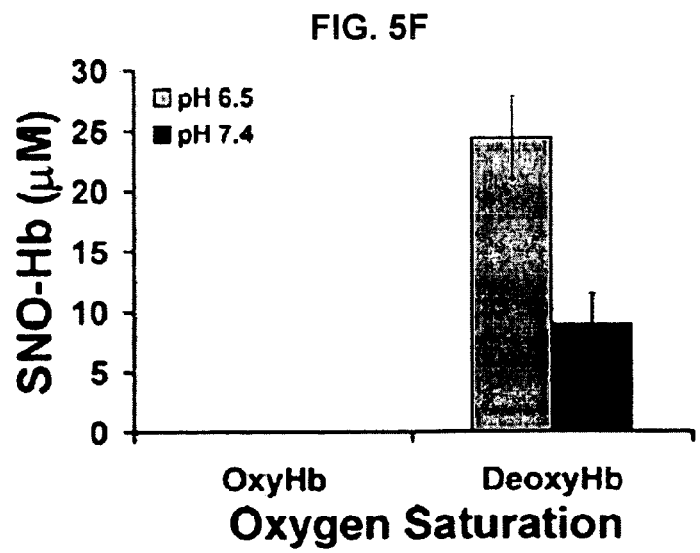

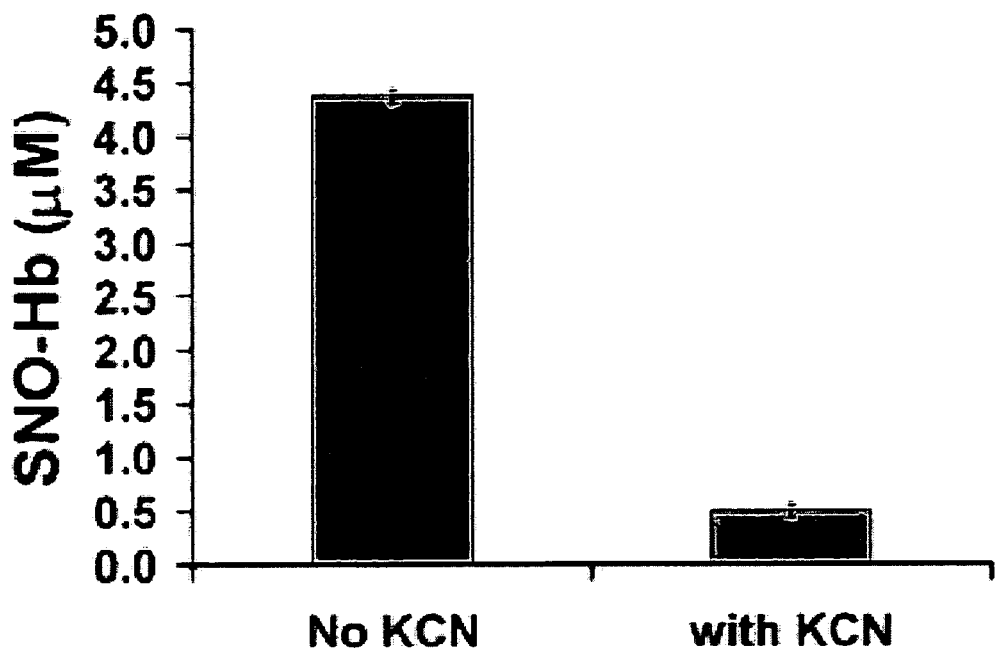
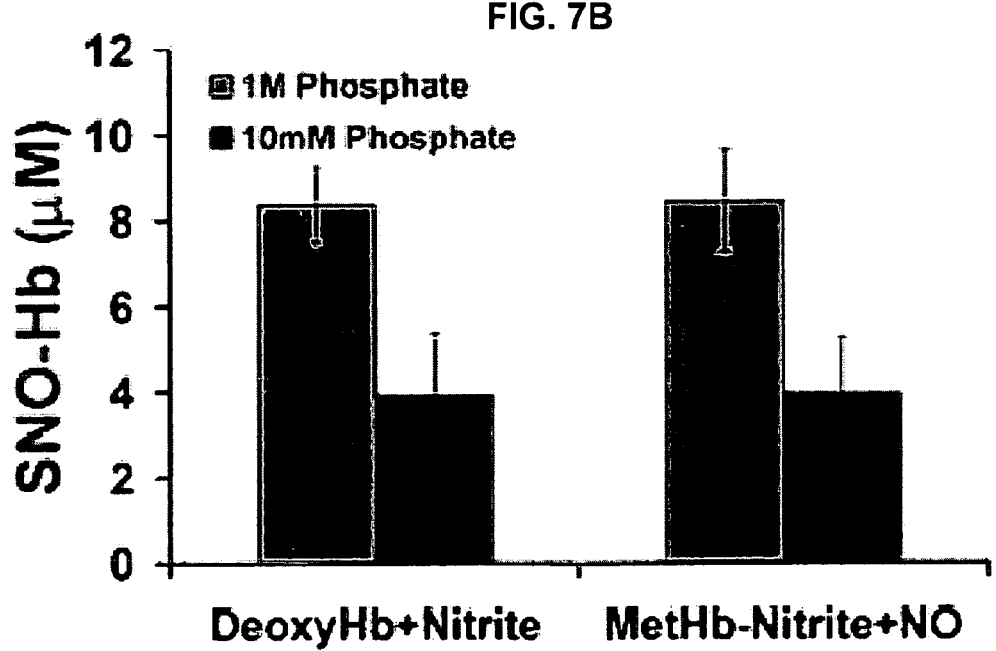

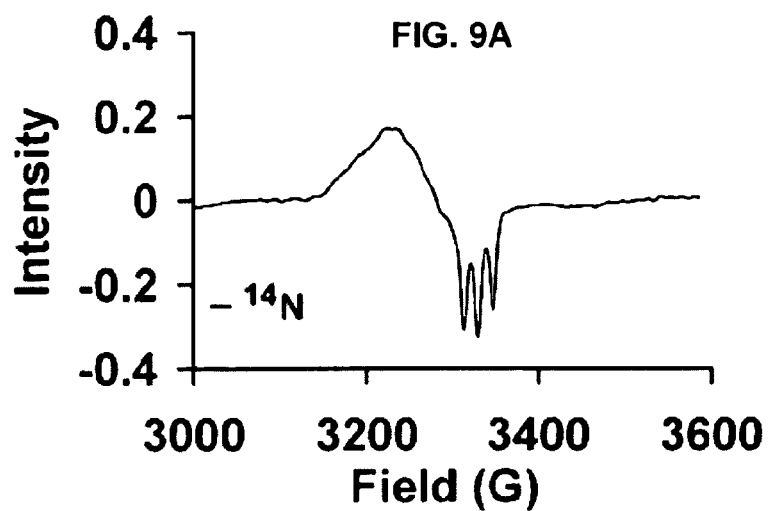
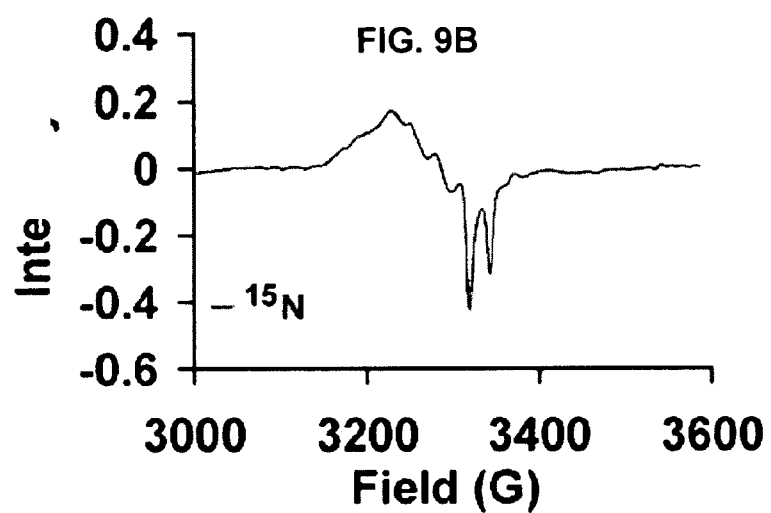
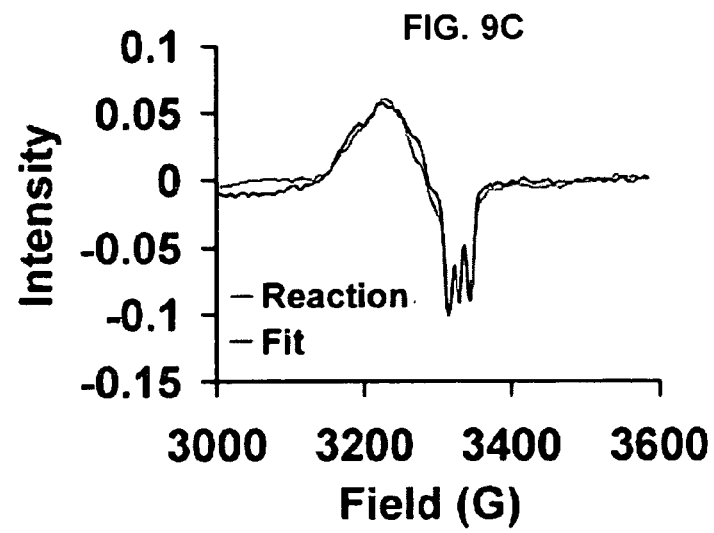

Mean arterial blood pressure during Trauma Hemorrhagic shock and & resuscitation

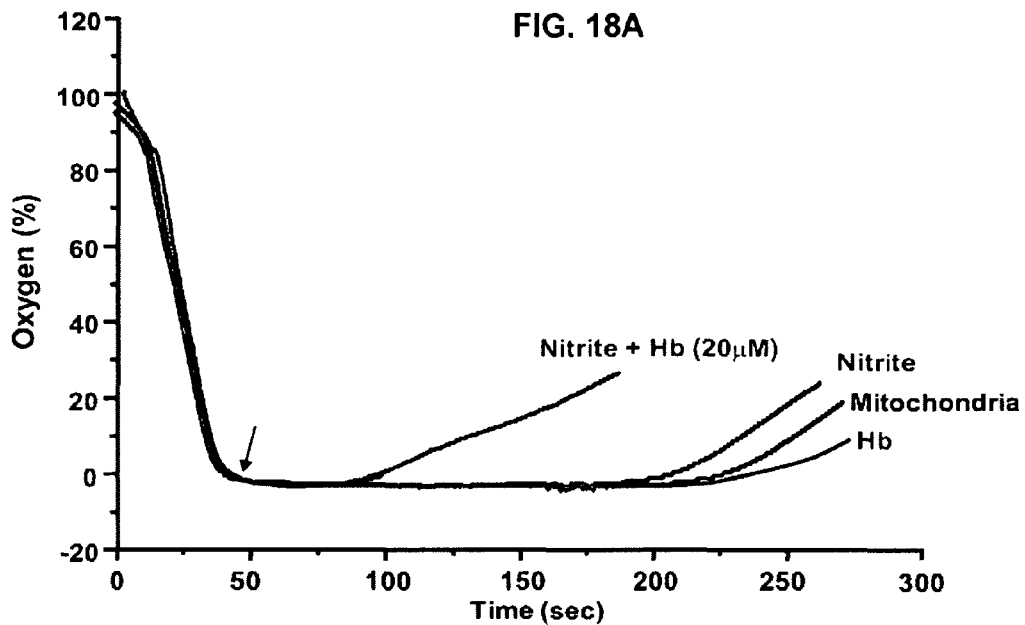
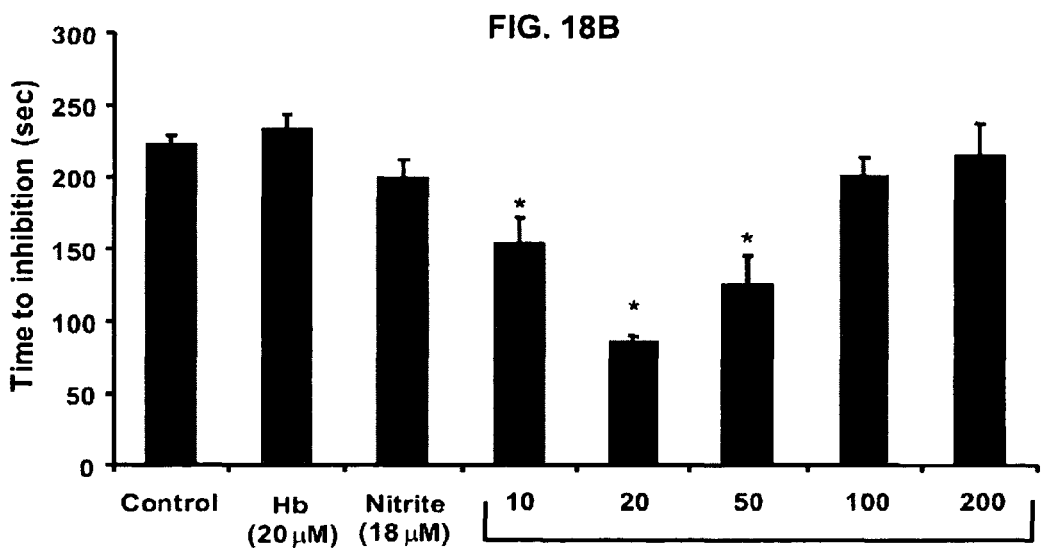

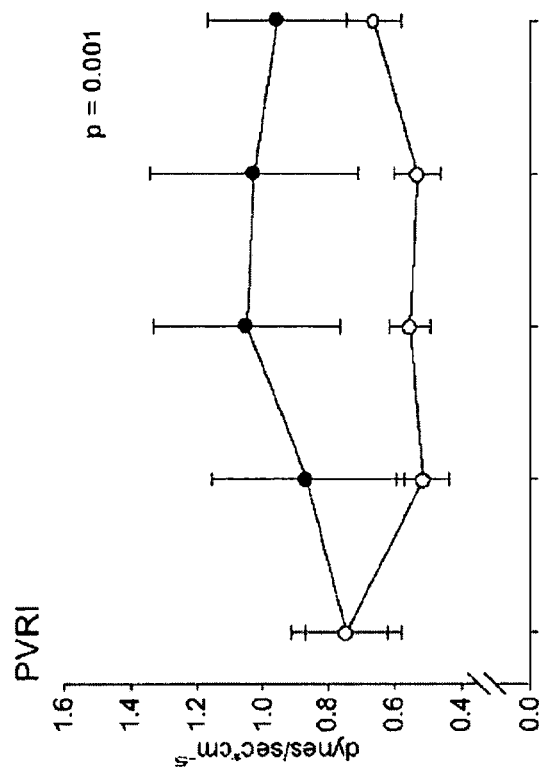
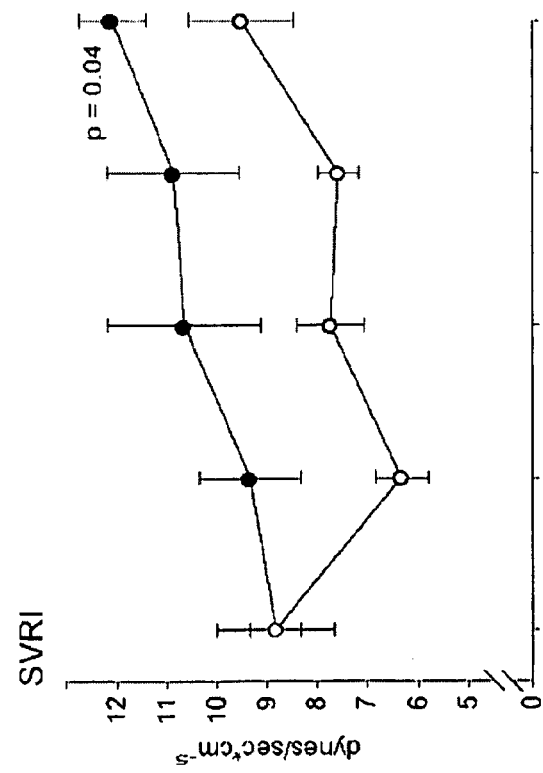
FIG. 19D
FIG. 19C

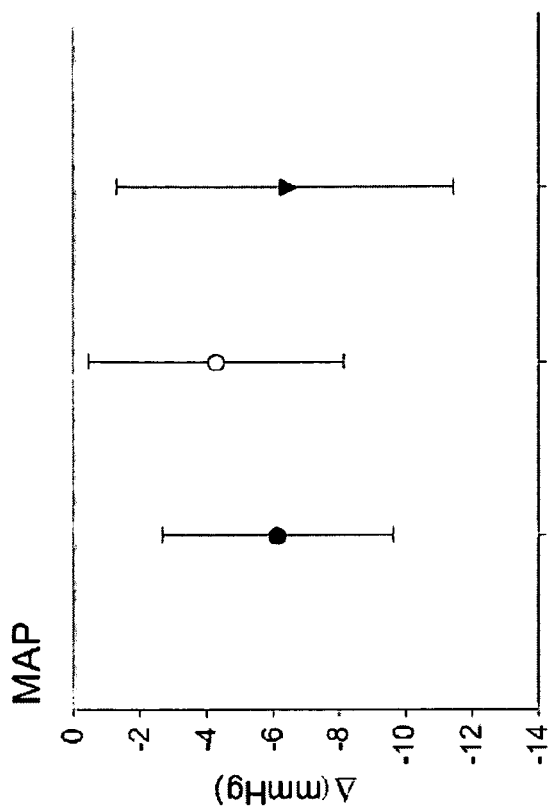
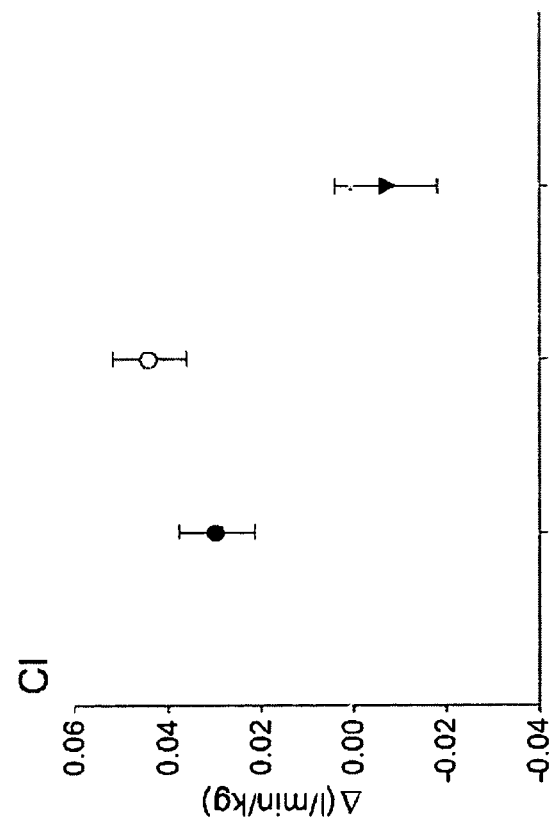

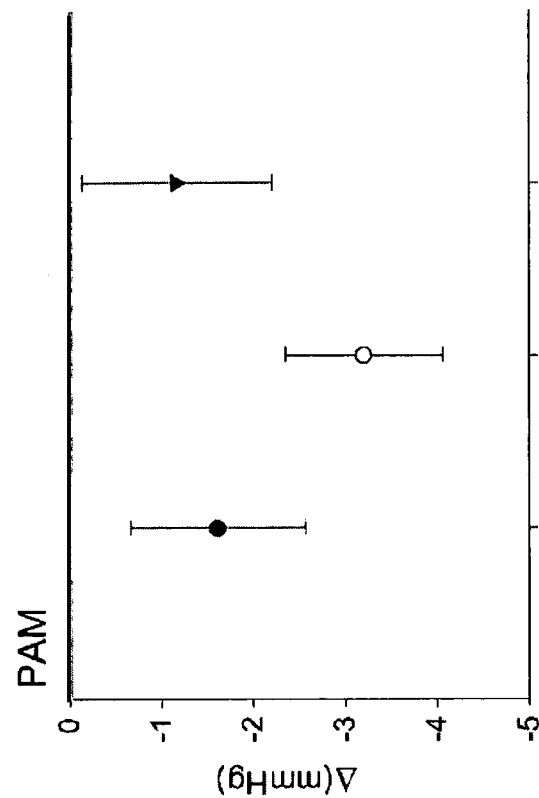
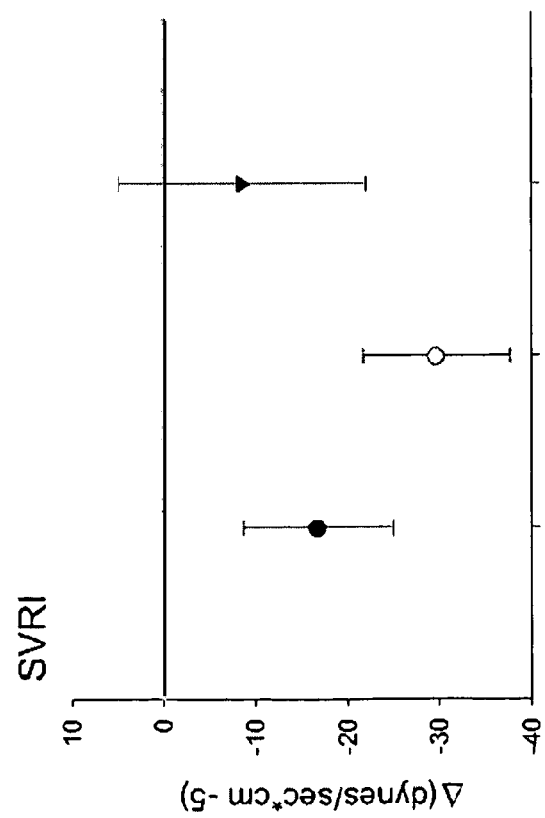

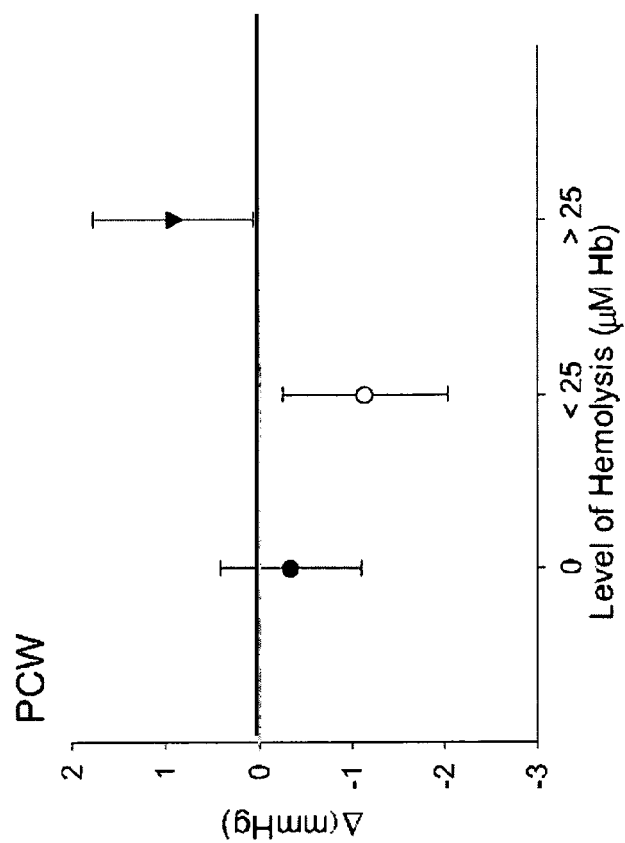
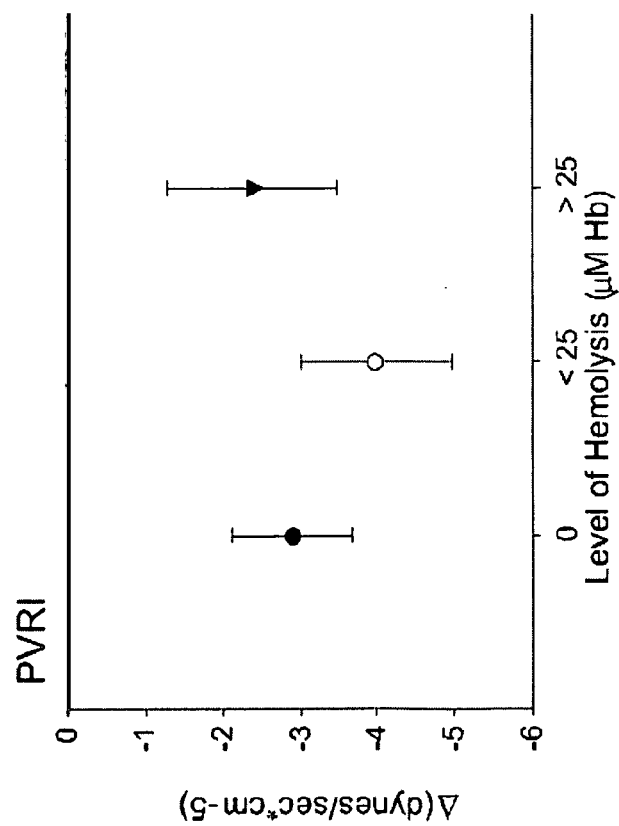
FIG. 21E
FIG. 21F

Cell-free plasma Hb < 25 µM + Nitrite

Cell-free plasma Hb > 25 µM + Nitrite

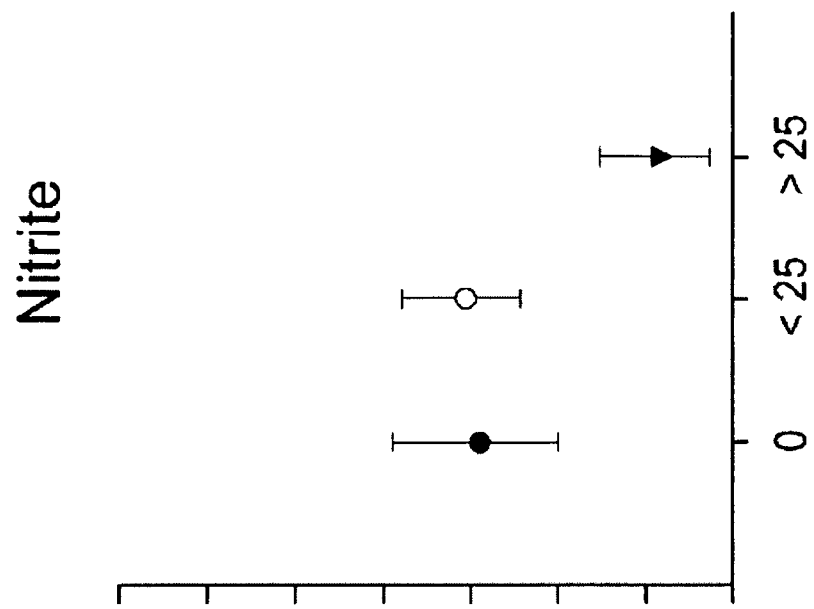
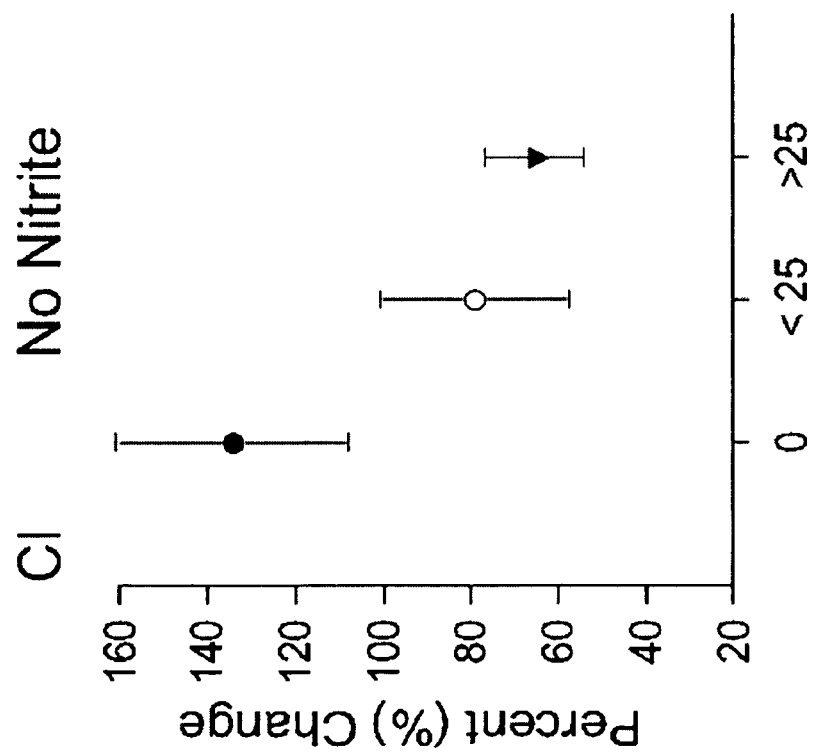

NITRITE AND NITRITE-METHEME THERAPY TO DETOXIFY STROMA-FREE HEMOGLOBIN BASED BLOOD SUBSTITUTES

CROSS REFERENCE TO RELATED APPLICATION

This application is the U.S. National Stage of International Application No. PCT/US2008/074856, filed Aug. 29, 2008, which was published in English under PCT Article 21(2), which claims the benefit of U.S. Provisional Application No. 60/969,530, filed Aug. 31, 2007, which is herein incorporated by reference in its entirety.

STATEMENT OF GOVERNMENT SUPPORT

This invention was made with government support under Contract No. HL058091 awarded by the National Institutes of Health. The United States government has certain rights in the invention.

FIELD

This disclosure relates to methods of producing non-toxic stroma-free hemoglobin-based blood substitutes for use in a subject. In particular, the disclosure relates to methods of delivering nitrite with hemoglobin as, for instance, a nitrite-methemoglobin intermediate, with other components of a stroma-free hemoglobin based blood substitute in order to reduce or eliminate vasoconstrictive properties inherent in hemoglobin based blood substitutes.

BACKGROUND

There has long been an urgent need in the medical community for a non-toxic blood substitute suitable for transfusion into a patient. In addition to trauma victims and surgical patients, patients suffering from diseases such as hemophilia and sickle-cell anemia are in need of frequent transfusions. One in twenty Americans will need a blood transfusion at some point in their lives, and each year approximately eight million volunteer donors make approximately 14 million blood donations. Several shortcomings of donated blood have contributed to the urgent demand for a cell-free blood substitute, including: the need to match blood types; concerns regarding disease transmission; morally- or religiously-based objections to blood transfusion; requirement for freezing of blood units; and limited storage lifetime. There are currently no clinically utilized oxygen-carrying blood substitutes for humans.

Hemoglobin is the molecule found within red blood cells that chelates molecular oxygen in the lungs and transports it throughout the body. The idea of using hemoglobin-containing solutions as a cell-free blood substitute has always been appealing. However, clinical studies consistently revealed that cell-free hemoglobin was associated with vasoconstriction leading to bradycardia, hypertension and renal failure. Infusion of these products increases the risk of myocardial infarction and death in human clinical trials. Many of these toxicities have now been attributed to the reaction with and scavenging of endogenous nitric oxide (NO), an important blood vessel dilator elaborated by the lining cells (endothelium) of the blood vessels. A major focus of recent research has been to attempt to modify hemoglobin in such a way that mitigates its NO scavenging and toxicity. For example, hemoglobin has been polymerized, intra-molecularly cross-linked, and conjugated to polyethyleneglycol (PEG). This work has resulted in some improvements in cell-free hemoglobin that increase circulating half lives, modulate oxygen affinities and ameliorate renal toxicity. However, vascular toxicity associated with cell-free hemoglobin remains a concern and is thought to be largely mediated by scavenging of nitric oxide and development of hypertension, inflammation and platelet aggregation. Of great clinical benefit would be the ability to resuscitate trauma or surgical patients with a cell-free hemoglobin solution that improves oxygen delivery without causing hypertension.

Recent studies reveal that the ubiquitous circulating anion nitrite ($NO_2^-$) is a vasodilator and intrinsic signaling molecule (Gladwin et al., *Proc. Natl. Acad. Sci. USA* 97:11482-11487, 2000; Cosby et al., *Nat. Med.* 9:1498-1505, 2003; Gladwin et al., *Nature Chemical Biology* 1:308-314, 2005; Bryan et al., *Nature Chemical Biology* 1:290-297, 2005; Modin et al., *Acta Physiologica Scandinavica* 171:9-16, 2001). The vasodilator activity of nitrite is associated with an allosterically controlled heme-based reduction of nitrite to nitric oxide (NO) by deoxygenated hemoglobin (deoxyHb) (Huang et al., *J. Biol. Chem.* 280:31126-31131, 2005; Huang, et al., *J. Clin. Invest.* 115:2099-2107, 2005). Nitrite infusions into the human circulation increase blood flow at near-physiological concentrations (Cosby et al., *Nat. Med.* 9:1498-1505, 2003). This vasodilation is temporally associated with increases in red cell heme iron-nitrosylated hemoglobin ($HbFe^{II}$—NO, designated as $\{FeNO\}^7$ using the Enemark-Feltham notation; Enemark & Feltham, *Coordination Chemistry Reviews* 13:339-406, 1974) and to a lesser extent S-nitrosated hemoglobin (SNO-Hb, hemoglobin nitrosated at the β-93 cysteine; Cosby et al., *Nat. Med.* 9:1498-1505, 2003).

SUMMARY

It unexpectedly has been found that co-administration of inorganic nitrite and cell-free hemoglobin in about equimolar concentrations (or lower concentrations of nitrite relative to hemoglobin) constitutes an oxygen carrying plasma expander, without vasoconstrictive properties in vivo. Thus, described herein is co-administration of cell-free hemoglobins with nitrite (free or as nitrite-methemoglobin complex) as a cell-free hemoglobin solution that improves oxygen delivery without causing hypertension. Moreover, regimes are provided that allow administration of therapeutics by first responders at the site of injury (e.g., in the case of trauma patients at the site of accidents by ambulance crews, or with soldiers on the battle field), which will be of great clinical benefit for maintaining organ perfusion in patients. Both cell-free hemoglobins and nitrite solutions would fulfill this function since sterile solutions of each can be prepared, stored and transported, and administered either intravenously or intraperitoneally.

Also described is a method of producing a cell-free blood substitute. The method includes contacting a ferric heme-containing molecule, such as methemoglobin ($Fe^{III}$-nitrite), with nitrite, wherein the molar ratio of hemoglobin to nitrite is about 1:1 or less, and thus forming nitrite-bound methemoglobin, wherein the nitrite-containing molecules produces an intermediate with nitrogen dioxide like electronic properties. NO in the vasculature or produced from the reduction of additional nitrite by deoxyhemoglobin can then react with this intermediate to form dinitrogen trioxide ($N_2O_3$), which is a potent vasodilator that ameliorates the toxicity of the stroma free hemoglobin. This reaction converts the nitrite-methemoglobin back into ferrous hemoglobin (deoxyhemoglobin), which can rebind oxygen in the lung. Thus this novel chemistry will both deliver oxygen, deliver $N_2O_3$ and NO, and redox cycle to rebind oxygen. In this embodiment, the nitrite-methemoglobin is co-infused with oxyhemoglobin in molar ratios of less than 1:1 to ensure both oxygen delivery and NO delivery. In another embodiment, a composition comprising nitrite and hemoglobin in a molar ratio of less than 1:2 is administered as a cell-free blood substitute to a subject. By way of example, the subject may be afflicted with anemia, bleeding disorders, burns, coagulopathy, ectopic pregnancy, favism, gastrointestinal bleeding, hemolytic uremic syndrome, hemophilia, microcytosis, ulcer, hemorrhage, rhabdomyolysis, hemorrhagic shock, sickle cell anemia, spherocytosis, thalassemia, yellow fever, or another disease or condition that would benefit from blood or plasma supplementation.

In another embodiment, the nitrite is bound to another ferric heme protein such as nitrite bound to a ferric derivative of a hemoglobin based blood substitute, or another hemoprotein (e.g., myoglobin, cytoglobin, neuroglobin) or a porphyrin compound.

The reaction of nitrite with deoxygenated hemoglobin generates vasodilatory NO and thus has the potential to replete the NO that is scavenged by the stroma-free hemoglobin-based blood substitutes. In addition, the newly discovered properties of nitrite-methemoglobin provide a new chemical pathway to NO generation that can be used to limit and reverse the toxicity of stroma-free hemoglobin based blood substitutes.

The foregoing and other features and advantages of the disclosure will become more apparent from the following detailed description of several embodiments which proceeds with reference to the accompanying figures.

BRIEF DESCRIPTION OF THE FIGURES

FIG. 7 is two graphs showing the evidence for $N_2O_3$ mediated nitrosation via nitrite bound MetHb. (A) DeoxyHb (300 µM) was reacted with nitrite (1 mM) for 30 minutes at pH 6.5 in the presence or absence of KCN (5 mM). SNO-Hb was subsequently measured using the modified 2C assay. Error bars represent one standard deviation from the mean (n=3). When this experiment was repeated with 2.5 mM KCN, SNO-Hb was measured to be 1.6±0.5 µM, compared to 4.3±1.4 µM when the reaction was repeated in parallel without KCN. (B) DeoxyHb (300 µM) was reacted with nitrite (1 mM) for 30 minutes at pH 6.5 in either PBS or 1 M phosphate buffer and SNO-Hb was measured by the modified 2C assay. MetHb (300 µM) was also reacted with nitrite (5 mM), generating MetHb-$NO_2^-$, with subsequent addition of ProliNO (1 mM) in either PBS or 1 M phosphate buffer. After 5 minutes the SNO-Hb was measured by the modified 2C assay. Error bars represent one standard deviation from the mean (n=3). When the MetHb-$NO_2^-$/ProliNO experiment was repeated in Tris buffer (no phosphate) slightly less SNO-Hb (2.2±0.9 µM) was made than when this was done in PBS. No SNO-Hb was measured when the MetHb (300 µM) was incubated with nitrite (1 mM) in pH 6.5 PBS buffer (no NO added) during a thirty minute anaerobic incubation.

FIG. 9 is a series of graphs showing the lack of an oxygen transfer mechanism. (A) EPR spectrum of pure Hb$^{14}$NO demonstrating triplet hyperfine splitting resulting from a mixture of 3 mM deoxyHb (treated with 15 mM dithionite) and 5 mM $^{14}$Nitrite. After 6 minutes, this was followed by treatment with 10 mM Sodium dodecyl sulphate to bring out hyperfine structure and frozen for EPR. (B) EPR spectrum of pure Hb$^{15}$NO demonstrating doublet hyperfine splitting resulting from a mixture of 3 mM deoxyHb (treated with 15 mM dithionite) and 5 mM $^{15}$Nitrite. After 6 minutes this was followed by treatment with 10 mM Sodium dodecyl sulphate and frozen for EPR. (C) A representative EPR spectrum (from n=3) of reaction of 5 mM $^{15}$nitrite and 50 µM $^{14}$NO added to 30 µM deoxygenated MetHb, for 5 min, followed by 10 mM Sodium dodecyl sulphate. The spectrum was fit to the basis spectra of Hb$^{14}$NO and Hb$^{15}$NO (fit). The β-nitrosyl component of the basis spectra were subtracted out for the fitting. The average percentage of Hb$^{14}$NO was found to be 69±5%. (The hyperfine splitting demonstrates mixture of $^{14}$N and $^{15}$N in the reaction product (HbFe$^{II}$—$^{14}$NO and HbFe$^{II}$—$^{15}$NO)).

FIG. 18 is two graphs showing that exact ratios of nitrite and hemoglobin will generate NO and inhibit mitochondrial respiration, thereby demonstrating the effect of nitrite and cell-free hemoglobin on NO generation. (A) Mitochondria (2 mg/ml) were stimulated to respire in the presence of no treatment, nitrite (18 µM), oxygenated hemoglobin (20 µM), or nitrite (18 µM) and hemoglobin (20 µM). Removal of the lid from the sealed chamber is denoted by the arrow. Time to inhibition was measured from removal of the lid to time the trace deviated from zero percent oxygen. In these experiments, the oxygen trace deviates from zero once the mitochondria stop respiring due to the exhaustion of substrate or inhibition by NO produced by reactions of hemoglobin with nitrite. (B) Quantification of several traces similar to those shown in (A) with different levels of hemoglobin. Inhibition of mitochondrial respiration (secondary to NO production) occurred most rapidly with nitrite and low levels of hemoglobin. The time to inhibition appears to be dependent on the rate of NO production from reactions of nitrite with deoxyhemoglobin and the rate of NO consumption by excess oxyhemoglobin. All data is mean±SEM of at least 3 independent experiments (*$p<0.01$ compared to nitrite alone).

DETAILED DESCRIPTION

I. Abbreviations

Figure 1B:
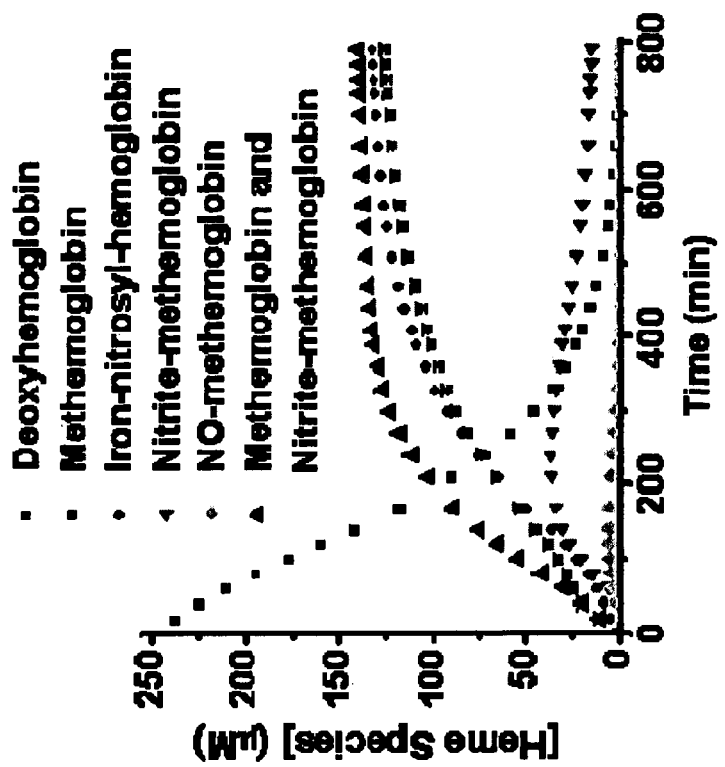
FIG. 1 is a series of graphs showing that nitrite-MetHb is the intermediate in the deoxyhemoglobin-nitrite reaction. (A) Disappearance of deoxyhemoglobin and formation of iron-nitrosyl-hemoglobin and total MetHb (sum of MetHb and nitrite-MetHb) over time in the reaction of 250 μM deoxyhemoglobin with 125 μM nitrite at pH 7.4 and 37° C. All Hb concentrations are reported on a heme basis, so 1 mM Hb reported here is 250 μM in Hb tetramers (ignoring Hb dimer formation). Reaction progress was monitored by absorption spectroscopy. (B) Concentrations of various heme species over time for the reaction shown in (A). Heme species include deoxyhemoglobin, MetHb, iron-nitrosyl-hemoglobin, nitrite-MetHb, and NO-MetHb. Total MetHb is also plotted labeled as Methemoglobin and nitrite-methemoglobin and is equal to the sum of these two species. (C) Comparison of chi squared values (sum squares of residual spectra obtained by spectral deconvolution) from the experiment in (A) fitted using four combination sets of standard spectra, which include deoxyhemoglobin, MetHb, iron-nitrosyl-hemoglobin, and additional standard spectra of either nitrite-MetHb alone, NO-MetHb alone, both species, or neither species. (D) The disappearance of deoxyhemoglobin and formation of iron-nitrosyl-hemoglobin and total MetHb (sum of MetHb and nitrite-MetHb) over time in the reaction of 450 μM deoxyhemoglobin with 5 mM nitrite at pH 7.4 and 37° C. (E) Concentrations of various heme species over time for the reaction shown in (D). Note that the plot of "Methemoglobin and Nitrite-methemoglobin" is equal to the sum of these two species that are also plotted separately. (F) Comparison of chi square values from the experiment in (D) fitted using four combination sets of standard spectra, which include deoxyhemoglobin, MetHb, iron-nitrosyl-hemoglobin, and additional standard spectra of either nitrite-MetHb alone, NO-MetHb alone, both species, or neither species.

| ABG | arterial blood gas |
| --- | --- |
| Aquo-metHb | water-Methemoglobin |
| cGMP | cyclic guanosine monophosphate |
| CI | cardiac index |
| CO | cardiac output |
| CVP | central venous pressure |
| D5W | 5% dextrose |
| DeoxyHb | deoxygenated hemoglobin |
| DFT | Density Functional Theory |
| DTPA | diethylenetriamine-pentaacetic acid |
| EPR | electron paramagnetic resonance spectroscopy |
| GSH | glutathione |
| GSNO | S-nitrosoglutathione |
| Hb | hemoglobin |
| HbFe$^{II}$—NO | ferrous iron-nitrosylated hemoglobin |
| HbFe$^{III}$—NO | ferric-iron-nitrosyl hemoglobin |
| Hb-NO | nitrosyl hemoglobin |
| HbS-NO | thio-nitrosyl hemoglobin |
| Hct | hematocrit |
| HR | heartrate |
| HUS | hemolytic uremic syndrome |

-continued

| i.v. | intravenous |
| --- | --- |
| KCN | potassium cyanide |
| MAP | mean arterial pressure |
| MetHb | methemoglobin |
| MetHbNO | ferric hemoglobin |
| MetHb-NO$_2^-$ | nitrite-bound methemoglobin |
| NEM | N-ethylmaleimide |
| Nitrite-MetHb | nitrite-bound methemoglobin |
| NOA | nitric oxide analyzer |
| NO-metHb | nitroxyl methemoglobin |
| NO$_x$ | molecular species of nitrogen and oxygen |
| OLYP | Handy/Cohen local exchange functional |
| OxyHb | oxygenated hemoglobin |
| PAM | pulmonary arterial pressure |
| PAOP | pulmonary artery occlusion pressure |
| PBS | phosphate-buffered saline |
| PCWP | pulmonary capillary wedge pressure |
| PEG | polyethylene glycol |
| PVRI | pulmonary vascular resistance index |
| RBC | red blood cell |
| SNO-Hb | s-nitrosated hemoglobin |
| STO-TZP | density functional theory calculations |
| SVRI | systemic vascular resistance index |
| TTP | thrombotic thrombocytopenic purpura |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Anemia: a deficiency of red blood cells (RBCs) and/or hemoglobin. Anemia is the most common disorder of the blood, and it results in a reduced ability of blood to transfer oxygen to the tissues. Since all human cells depend on oxygen for survival, varying degrees of anemia can have a wide range of clinical consequences. The three main classes of anemia include excessive blood loss (acutely such as a hemorrhage or chronically through low-volume loss), excessive blood cell destruction (hemolysis) or deficient red blood cell production (ineffective hematopoiesis).

The term "anemia" refers to all types of clinical anemia, including but not limited to: microcytic anemia, iron deficiency anemia, hemoglobinopathies, heme synthesis defect, globin synthesis defect, sideroblastic defect, normocytic anemia, anemia of chronic disease, aplastic anemia, hemolytic anemia, macrocytic anemia, megaloblastic anemia, pernicious anemia, dimorphic anemia, anemia of prematurity, Fanconi anemia, hereditary spherocytosis, sickle-cell anemia, warm autoimmune hemolytic anemia, cold agglutinin hemolytic anemia.

In severe cases of anemia, or with ongoing blood loss, a blood transfusion may be necessary. Doctors may use any of a number of clinically accepted criteria to determine that a blood transfusion is necessary to treat a subject with anemia. For instance, the currently accepted Rivers protocol for early goal-directed therapy for sepsis requires keeping the hematocrit above 30.

Anoxia: a pathological condition in which the body as a whole or region of the body is completely deprived of oxygen supply.

Bleeding disorders: a general term for a wide range of medical problems that lead to poor blood clotting and continuous bleeding. Doctors also refer to bleeding disorders by terms such as, for example, coagulopathy, abnormal bleeding and clotting disorders.

Burns: any extremity experienced by the skin caused by heat, cold, electricity, chemicals, friction or radiation.

Cell-free or Stroma-free blood substitute: a composition lacking erythrocytes and other whole cell components of blood used to replace whole blood in a subject. An excellent "blood substitute" is one which mimics the oxygen-carrying capacity of hemoglobin, which requires no cross-matching or compatibility testing, with a long shelf life, which exhibits a long intravascular half life (over days and weeks), and is free of side effects and pathogens. Three main types of blood substitutes are in development: hemoglobin-based oxygen carriers, perfluorocarbon emulsions, and encapsulated hemoglobin in lipid vesicles.

The general task of blood within the frame of classic transfusion medicine is to supply oxygen to tissue (oxygen transport from lung to tissue, oxygen release and picking up carbon dioxide). All of this is accomplished by hemoglobin (Hb), the oxygen carrier protein contained within red cells. Early attempts to develop blood substitutes were focused on simple cell-free solutions of hemoglobin. Early studies conducted in experimental animals showed that infusion of free hemoglobin caused a substantial increase in oncotic pressure because of its hyperosmolarity, coagulopathy, and hypertensive properties.

One significant problem and source of free hemoglobin's hypertensive properties was the affinity of Hb for nitric oxide (NO). NO produced by endothelial cells affects smooth muscle cells of the vessel wall and modulates the vascular tone toward vasodilatation. Cell-free Hb scavenges NO and shifts vasomotor tone toward vasoconstriction. Cell-free hemoglobin-induced vasoconstriction leads to serious side effects during transfusion of a subject manifested as an increase in systemic and pulmonary artery pressure without normalizing cardiac output or restoring intravascular volume. Decreases in the cardiac index impair optimum oxygen delivery and outweigh the advantage of an oxygen-carrying solution. Severe vasoconstriction complications caused the termination of clinical trials of unmodified cell-free hemoglobin as a blood substitute.

Modified Hb molecules have been produced in an attempt to overcome other limitations of hemoglobin for use in a blood substitute, for example the penetration of Hb molecules into the interstitial space of the subendothelial layers of blood vessel walls and the sensitization of peripheral α-adrenergic receptors. Successful modifications include purification, cross-linkage, and polymerization. Administration of these modified hemoglobins leads to vasoconstrictive effects that may increase systemic and pulmonary vascular resistance with resultant decreases in cardiac index. Clinical trials with these modified hemoglobins in healthy volunteers showed dose-dependent moderate or severe abdominal pain and increases in mean arterial pressure. The current state of the art is that there are no cell-free blood substitutes approved for clinical use in the United States.

Coagulopathy: a medical term for a defect in the body's mechanism for blood clotting.

Ectopic pregnancy: a complication of pregnancy in which the fertilized ovum is implanted in any tissue other than the uterine wall.

Favism: the common name of glucose-6-phosphate dehydrogenase (G6PD) deficiency; an X-linked recessive hereditary disease featuring non-immune hemolytic anemia in response to a number of causes.

Gastrointestinal bleeding: every form of hemorrhage (loss of blood) in the gastrointestinal tract, from the pharynx to the rectum.

Heme-containing molecule: any molecule comprising a heme prosthetic group. The heme prosthetic group that of an iron atom contained in the center of a large heterocyclic organic ring called a porphyrin. Some, but not all, porphyrins contain iron. By way of example, heme-containing molecules include (but are not limited to) cytoglobin, neuroglobin, hemoglobin, Hemoglobin S, F, A2 zeta and other hemoglobins, porphyrin compounds, and mutant globins, such as hemoglobins, with modified oxygen affinity, size, viscosity, redox potential, and/or heme pocket geometry.

Hemoglobin: the iron-containing oxygen-transport metalloprotein in the red blood cells of the blood in vertebrates and other animals. In humans, the hemoglobin molecule is an assembly of four globular protein subunits. Each subunit is composed of a protein chain tightly associated with a non-protein heme group. Each protein chain arranges into a set of alpha-helix structural segments connected together in a globin fold arrangement, so called because this arrangement is the same folding motif used in other heme/globin proteins such as myoglobin. This folding pattern contains a pocket which strongly binds the heme group.

The heme group consists of an iron (Fe) ion (charged atom) held in a heterocyclic ring, known as a porphyrin. The iron ion, which is the site of oxygen binding, bonds with the four nitrogens in the center of the ring, which all lie in one plane. The iron is also bound strongly to the globular protein via the imidazole ring of a histidine residue below the porphyrin ring. A sixth position can reversibly bind oxygen, completing the octahedral group of six ligands. Oxygen binds in an "end-on bent" geometry where one oxygen atom binds Fe and the other protrudes at an angle. When oxygen is not bound, a very weakly bonded water molecule fills the site, forming a distorted octahedron. The iron ion may either be in the $Fe^{II}$ or $Fe^{II}$ state, but ferrihemoglobin (methemoglobin) ($Fe^{III}$) cannot bind oxygen. In binding, oxygen temporarily oxidizes Fe to ($Fe^{III}$), so iron must exist in the +2 oxidation state in order to bind oxygen. The body reactivates hemoglobin found in the inactive ($Fe^{III}$) state by reducing the iron center.

In adult humans, the most common hemoglobin type is a tetramer (which contains 4 subunit proteins) called hemoglobin A, consisting of two α and two β subunits non-covalently bound, each made of 141 and 146 amino acid residues, respectively. This is denoted as α2β2. The subunits are structurally similar and about the same size. Each subunit has a molecular weight of about 17,000 daltons, for a total molecular weight of the tetramer of about 68,000 daltons. The four polypeptide chains are bound to each other by salt bridges, hydrogen bonds, and hydrophobic interactions.

Oxyhemoglobin is formed during respiration when oxygen binds to the heme component of the protein hemoglobin in red blood cells. This process occurs in the pulmonary capillaries adjacent to the alveoli of the lungs. The oxygen then travels through the blood stream to be delivered to cells where it is utilized in aerobic glycolysis and in the production of ATP by the process of oxidative phosphorylation.

Deoxyhemoglobin is the form of hemoglobin without bound oxygen. The absorption spectra of oxyhemoglobin and deoxyhemoglobin differ. The oxyhemoglobin has significantly lower absorption of the 660 nm wavelength than deoxyhemoglobin, while at 940 nm its absorption is slightly higher.

Hemolysis: the breaking open of red blood cells and the release of hemoglobin into the surrounding fluid.

Hemolytic uremic syndrome (HUS): a disease characterized by microangiopathic hemolytic anemia, acute renal failure and a low platelet count (thrombocytopenia). The classic childhood case of hemolytic uremic syndrome occurs after bloody diarrhea caused by *E. coli* O157:H7, a strain of *E. coli* that expresses verotoxin (also called Shiga toxin). The toxin enters the bloodstream, attaches to renal endothelium and initiates an inflammatory reaction leading to acute renal failure and disseminated intravascular coagulation. The fibrin mesh destroys red blood cells and captures thrombocytes, leading to a decrease of both in full blood count. Adult HUS has similar symptoms and pathology but is an uncommon outcome of the following: HIV; antiphospholipid syndrome (associated with Lupus erythematosus and generalized hypercoagulability); post partum renal failure; malignant hypertension; scleroderma; and cancer chemotherapy (mitomycin, cyclosporine, cisplatin and bleomycin). A third category is referred to as Familial hemolytic uremic syndrome. It represents 5-10% of hemolytic uremic syndrome cases and is due to an inherited deficiency leading to uncontrolled complement system activation.

Hemophilia: the name of several hereditary genetic illnesses that impair the body's ability to control coagulation.

Hemorrhage: the loss of blood from the circulatory system. Bleeding can occur internally, where blood leaks from blood vessels inside the body, or externally, either through a natural opening such as vagina, mouth or rectum, or through a break in the skin.

The average human has around 7 to 8% of their body weight made up of blood. This equates to an average of around 5 liters of blood (5.3 quarts) in a 70 kg (154 lbs.) man. The circulating blood volume is approximately 70 ml/kg of ideal body weight. Thus the average 70 kg male has approximately 5000 ml (5.3 quarts) of circulating blood. Loss of 10-15% of total blood volume can be endured without clinical sequelae in a healthy person, and blood donation typically takes 8-10% of the donor's blood volume. The technique of blood transfusion is used to replace severe quantities of lost blood.

Hemorrhage generally becomes dangerous, or even fatal, when it causes hypovolemia (low blood volume) or hypotension (low blood pressure). In these scenarios various mechanisms come into play to maintain the body's homeostasis. These include the "retro-stress-relaxation" mechanism of cardiac muscle, the baroreceptor reflex and renal and endocrine responses such as the renin-angiotensin-aldosterone system.

Hemorrhage is broken down into four classes by the American College of Surgeons' Advanced Trauma Life Support:

Class I Hemorrhage involves up to 15% of blood volume. There is typically no change in vital signs and fluid resuscitation is not usually necessary.

Class II Hemorrhage involves 15-30% of total blood volume. A patient is often tachycardic (rapid heart beat) with a narrowing of the difference between the systolic and diastolic blood pressures. The body attempts to compensate with peripheral vasoconstriction. Volume resuscitation with crystaloids (Saline solution or Lactated Ringer's solution) is all that is typically required. Atypically, blood transfusion may be required.

Class III Hemorrhage involves loss of 30-40% of circulating blood volume. The patient's blood pressure drops, the heart rate increases, peripheral perfusion, such as capillary refill worsens, and the mental status worsens. Fluid resuscitation with crystaloid and blood transfusion are usually necessary.

Class IV Hemorrhage involves loss of >40% of circulating blood volume. The limit of the body's compensation is reached and aggressive resuscitation is required to prevent death.

Hemorrhagic shock: a condition of reduced tissue perfusion, resulting in the inadequate delivery of oxygen and nutrients that are necessary for cellular function. Hypovolemic shock, the most common type, results from a loss of circulating blood volume from clinical etiologies, such as penetrating and blunt trauma, gastrointestinal bleeding, and obstetrical bleeding.

Hypoxaemia: an abnormal deficiency in the concentration of oxygen in arterial blood.

Hypoxia: a pathological condition in which the body as a whole (generalized hypoxia) or region of the body (tissue hypoxia) is deprived of adequate oxygen supply.

Ischemia: A vascular phenomenon in which a decrease in the blood supply to a bodily organ, tissue, or part is caused, for instance, by constriction or obstruction of one or more blood vessels. Ischemia sometimes results from vasoconstriction or thrombosis or embolism. Ischemia can lead to direct ischemic injury, tissue damage due to cell death caused by reduced oxygen supply.

Ischemia/reperfusion injury: In addition to the immediate injury that occurs during deprivation of blood flow, ischemic/reperfusion injury involves tissue injury that occurs after blood flow is restored. Current understanding is that much of this injury is caused by chemical products and free radicals released into the ischemic tissues.

When a tissue is subjected to ischemia, a sequence of chemical events is initiated that may ultimately lead to cellular dysfunction and necrosis. If ischemia is ended by the restoration of blood flow, a second series of injurious events ensue, producing additional injury. Thus, whenever there is a transient decrease or interruption of blood flow in a subject, the resultant injury involves two components—the direct injury occurring during the ischemic interval and the indirect or reperfusion injury that follows. When there is a long duration of ischemia, the direct ischemic damage, resulting from hypoxia, is predominant. For relatively short duration ischemia, the indirect or reperfusion mediated damage becomes increasingly important. In some instances, the injury produced by reperfusion can be more severe than the injury induced by ischemia per se. This pattern of relative contribution of injury from direct and indirect mechanisms has been shown to occur in all organs.

Methemoglobin: The oxidized form of hemoglobin in which the iron in the heme component has been oxidized from the ferrous (+2) to the ferric (+3) state. This renders the hemoglobin molecule incapable of effectively transporting and releasing oxygen to the tissues. Normally, there is about 1% of total hemoglobin in the methemoglobin form.

Microcytosis: a blood disorder characterized by the presence of microcytes (abnormally small red blood cells) in the blood.

Nitrite: The inorganic anion $^-NO_2$ or a salt of nitrous acid ($NO_2^-$). Nitrites are often highly soluble, and can be oxidized to form nitrates or reduced to form nitric oxide or ammonia. Nitrite may form salts with alkali metals, such as sodium ($NaNO_2$, also known as nitrous acid sodium salt), potassium and lithium, with alkali earth metals, such as calcium, magnesium and barium, with organic bases, such as amine bases, for example, dicyclohexylamine, pyridine, arginine, lysine and the like. Other nitrite salts may be formed from a variety of organic and inorganic bases. In particular embodiments, the nitrite is a salt of an anionic nitrite delivered with a cation, which cation is selected from sodium, potassium, and arginine. Many nitrite salts are commercially available, and/or readily produced using conventional techniques.

Nitrosation: a process of converting organic compounds into nitroso compounds.

Parenteral: Administered outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable carrier: The pharmaceutically acceptable carriers useful in this disclosure are conventional. Parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease. "Treatment" refers to a therapeutic intervention that ameliorates a sign or symptom of a disease or pathological condition after it has begun to develop.

Rhabdomyolysis: The rapid breakdown of skeletal muscle tissue due to traumatic injury, including mechanical, physical or chemical. The principal result is a large release of the creatine phosphokinase enzymes and other cell byproducts into the blood system and acute renal failure due to accumulation of muscle breakdown products, several of which are injurious to the kidney.

Sickle cell anemia: A group of genetic disorders caused by sickle hemoglobin. In many forms of the disease, the red blood cells change shape upon deoxygenation because of polymerization of the abnormal sickle hemoglobin. This process damages the red blood cell membrane, and can cause the cells to become stuck in blood vessels. This deprives the downstream tissues of oxygen and causes ischemia and infarction, which may cause organ damage, such as stroke.

Spherocytosis: An auto-hemolytic anemia characterized by the production of red blood cells (or erythrocytes) that are sphere-shaped, rather than donut-shaped.

Subject: Living multi-cellular organisms, including vertebrate organisms, a category that includes both human and non-human mammals.

Thalassemia: An inherited autosomal recessive blood disease. In thalassemia, the genetic defect results in reduced rate of synthesis of one of the globin chains that make up hemoglobin. Reduced synthesis of one of the globin chains causes the formation of abnormal hemoglobin molecules, and this in turn causes the anemia which is the characteristic presenting symptom of the thalassemias.

Therapeutically effective amount: A quantity of compound or composition, for instance, cell-free hemoglobin based blood substitute detoxified by treatment with nitrite, sufficient to achieve a desired effect in a subject being treated. For instance, this can be the amount necessary to inhibit or to measurably reduce anemia or other symptom associated with a blood disorder. It can also be the amount necessary to restore normal vascular tone and oxygenation to a subject suffering from hemorrhage.

Ulcer: An open sore of the skin, eyes or mucous membrane, often caused, but not exclusively, by an initial abrasion and generally maintained by an inflammation, an infection, and/or medical conditions which impede healing.

Vasoconstriction: The diminution of the caliber or cross-sectional area of a blood vessel, for instance constriction of arterioles leading to decreased blood flow to a body part. This can be caused by a specific vasoconstrictor, an agent (for instance a chemical or biochemical compound) that causes, directly or indirectly, constriction of blood vessels. Such an agent can also be referred to as a vasohypertonic agent, and is said to have vasoconstrictive activity. A representative category of vasoconstrictors is the vasopressor (from the term pressor, tending to increase blood pressure), which term is generally used to refer to an agent that stimulates contraction of the muscular tissue of the capillaries and arteries.

Vasoconstriction also can be due to vasospasm, inadequate vasodilatation, thickening of the vessel wall, or the accumulation of flow-restricting materials on the internal wall surfaces or within the wall itself. Vasoconstriction is a major presumptive or proven factor in aging and in various clinical conditions including progressive generalized atherogenesis, myocardial infarction, stroke, hypertension, glaucoma, macular degeneration, migraine, hypertension and diabetes mellitus, among others.

Vasodilation: A state of increased caliber of the blood vessels, or the act of dilation of a blood vessel, for instance dilation of arterioles leading to increased blood flow to a body part. This can be caused by a specific vasodilator, an agent (for instance, a chemical or biochemical compound) that causes, directly or indirectly, dilation of blood vessels. Such an agent can also be referred to as a vasohypotonic agent, and is said to have vasodilative activity.

Yellow fever: An acute viral disease that is a cause of hemorrhagic illness, particularly in many African and South American countries.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein in one embodiment is a pharmaceutical composition, comprising a ferric ($Fe^{III}$) heme-containing molecule and nitrite. In examples of this composition, the molar ratio of nitrite to the heme-containing molecule is defined, for instance the molar ratio is less than 1:1, more than 1:1, or about 1.1. Example heme-containing molecules include (but are not limited to) hemoglobin, methemoglobin, cross-linked hemoglobin, cross-linked methemoglobin, a protein (or protein fragment, such as a protein domain) that binds oxygen, or a combination or mixture of two or more thereof.

Other example compositions further comprise a pharmaceutically acceptable carrier, an adjuvant, or two or a combination of two or more thereof.

Also provided is a method of producing a cell-free blood substitute, which method comprises contacting a heme-containing molecule with nitrite, wherein the molar ratio of heme-containing molecule and nitrite in the composition is between about 1:2 and about 2:1, is above 1:1, is below 1:1, or is about 1:1; and forming nitrite-bound heme-containing molecules, wherein the nitrite-containing molecules produce dinitrogen trioxide.

Other embodiments provide methods of treating a subject having or predisposed to hypoxia, hypoxaemia, ischemia or anoxia, which methods comprise administering to the subject a therapeutically effective amount of a ferric ($Fe^{III}$) heme-containing molecule and nitrite composition as described herein, thereby treating the subject.

Yet other embodiments are methods of replacing blood in a subject, which methods comprise administering to the subject a therapeutically effective amount of a ferric ($Fe^{III}$) heme-containing molecule and nitrite composition as described herein, thereby replacing blood in the subject.

By way of example, the subject to which a composition or preparation described herein is to be administered includes a subject that has or is predisposed to anemia, bleeding disorder, trauma, injury, burn, coagulopathy, ectopic pregnancy, favism, gastrointestinal bleeding, hemolytic uremic syndrome, hemophilia, microcytosis, ulcer, bleeding in surgery, bleeding in pregnancy, hemorrhage, rhabdomyolysis, hemorrhagic shock, sickle cell anemia, hemoglobinopathy spherocytosis, thalassemia, and/or yellow fever. Alternatively, the subject has lost blood during a surgical procedure. In some examples, the subject is a human; in others, the subject is a non-human animal.

Yet additional embodiments and examples are provided herein.

IV. Detailed Description of Particular Embodiments

A. Production of Molecular Dinitrogen Trioxide ($N_2O_3$) via Reaction of NO and a Nitrite-Bound Methemoglobin Intermediate Recent studies reveal that the ubiquitous circulating anion nitrite ($NO_2^-$) is a vasodilator and intrinsic signaling molecule (Gladwin et al., *Proc. Natl. Acad. Sci. USA* 97:11482-11487, 2000; Cosby et al., *Nat. Med.* 9:1498-1505, 2003; Gladwin et al., *Nature Chemical Biology* 1:308-314, 2005; Bryan et al., *Nature Chemical Biology* 1:290-297, 2005; Modin et al., *Acta Physiologica Scandinavica* 171:9-16, 2001). The vasodilator activity of nitrite is associated with an allosterically controlled heme-based reduction of nitrite to nitric oxide (NO) by deoxygenated hemoglobin (deoxyHb) (Huang et al., *J. Biol. Chem.* 280:31126-31131, 2005; Huang et al., *J. Clin. Invest.* 115:2099-2107, 2005). Nitrite infusions into the human circulation increase blood flow at near physiological concentrations. (Cosby et al., *Nat. Med.* 9:1498-14505, 2003). This vasodilation is temporally associated with increases in red cell heme iron-nitrosylated hemoglobin ($HbFe^{II}$—NO designated as $\{FeNO\}^7$ using the Enemark-Feltham notation; Enemark & Feltham (1974) *Coordination Chemistry Reviews* 13:339-406) and to a lesser extent S-nitrosated hemoglobin (SNO-Hb, hemoglobin nitrosated at the β-93 cysteine; Cosby et al., *Nat. Med.* 9:1498-1505, 2003).

While the in vitro incubation of nitrite with deoxygenated red cells and hemoglobin solutions produces vasodilation, tissue NO-dependent cGMP accumulation, gas phase NO generation, and NO-dependent inhibition of mitochondrial oxygen consumption, the mechanism of NO escape from the red cell following nitrite reduction by hemoglobin remains elusive (Cosby et al., *Nat. Med.* 9:1498-1505, 2003; Crawford et al., *Blood* 107:566-574, 2006; Hunter et al., *Nat. Med.* 10:1122-1127, 2004). Indeed, a major challenge to the nitrite reductase hypothesis and other erythrocyte-NO export theories is explaining how the NO can escape heme autocapture (Gladwin et al., *Proc. Natl. Acad. Sci. USA* 97:11482-11487, 2000). Nitric oxide reacts with both deoxy- and oxyhemoglobin extremely rapidly with bimolecular rate constants between $10^7$-$10^8$ $M^{-1}s^{-1}$ (Gladwin et al., *Proc. Natl. Acad. Sci. USA* 97:11482-11487, 2000; Doyle & Hoekstra, *J. Inorg. Biochem.* 14:351-358, 1981; Eich et al., *Biochemistry-US* 35:6976-6983, 1996; Herold et al., *Biochemistry-US* 40:3385-3395, 2001; Cassoly & Gibson, *J. Mol. Biol.* 91:301-313, 1975; Morris & Gibson, *J. Biol. Chem.* 255:8050-8053, 1980; Huang et al., *Biophys. J.* 85:2374-2383, 2003; Kim-Shapiro, *Free Radic. Biol. Med.* 36:402-412, 2004). Modeling calculations have shown that only 0.1 pM NO would be produced outside a red blood cell at steady state, even at supra-physiological nitrite levels, unless additional mechanisms exist to limit the scavenging reactions of NO with hemoglobin (Jeffers et al., *Comp. Biochem. Physiol. A-Mol. Integr. Physiol.* 142:130-135, 2005). A similar paradox could be seen in the cardiomyocyte where nitrite inhibits cellular respiration during hypoxia via a nitrite reductase activity of deoxymyoglobin, despite the fact that the high concentrations of myoglobin in the cardiomyocyte could be expected to inhibit NO-dependent signaling (Shiva et al., *Circ. Res.* 100: 654-661, 2007). The possibility was therefore considered that the nitrite-hemoglobin reactions are either compartmentalized at the red cell membrane to limit cytoplasmic scavenging or generate gaseous $NO_x$ species such as $N_2O_3$ which can concentrate in the membrane or in hydrophobic membrane channels, and thereby diffuse out of the red blood cell (Huang et al., *J. Clin. Invest.* 115:2099-2107, 2005; Robinson & Lancaster, *Am. J. Respir. Cell Mol. Biol.* 32:257-261, 2005). $N_2O_3$ is a logical candidate for such an intermediate as 1) it is a primary nitrosating species capable of generating red cell S-nitrosothiols (Robinson & Lancaster, *Am. J. Respir. Cell Mol. Biol.* 32:257-261, 2005; Williams (Elsevier, Amersterdam, 2004) *Nitrosation Reactions and the Chemistry of Nitric Oxide*; Wink et al., *Chem. Res. Toxicol.* 6:23-27, 1993; Dabora et al., *Iarc Scientific Publications* 311-316, 1984), which clearly form as a side product of the nitrite-hemoglobin reaction (Cosby et al., *Nat. Med.* 9:1498-1505, 2003), 2) it is small and uncharged, facilitating diffusion through the red cell membrane, and 3) it can homolyze to NO and $NO_2^-$, allowing for export of NO (Jeffers et al., *Comp. Biochem. Physiol. A-Mol. Integr. Physiol.* 142:130-135, 2005; Robinson & Lancaster, *Am. J. Respir. Cell Mol. Biol.* 32:257-261, 2005).

If $N_2O_3$ is formed in the reaction of nitrite and deoxyhemoglobin, then nitrosated products should be detectable. During nitrite infusions in humans, in addition to the expected products of methemoglobin (MetHb) and $HbFe^{II}$—NO, SNO-Hb is also formed (Cosby et al., *Nat. Med.* 9:1498-1505, 2003). The reaction of deoxyHb and nitrite also forms S-nitrosothiols, including SNO-Hb (Stepuro et al., *Polish Journal of Pharmacology* 46:601-607, 1994; Stepuro et al., *Biochem.-Moscow* 62:960-966, 1997; Luchsinger et al., *Proc. Natl. Acad. Sci. USA* 100:461-466, 2003; Fernandez & Ford, *J Am Chem Soc* 125:10510-10511, 2003; Nagababu et al., *Nitric*

Oxide 15:20-29, 2006). It has also been suggested that the formation of SNO-Hb from nitrite involves the formation of ferrous-iron-nitrosyl-hemoglobin (HbFe$^{II}$—NO) followed by the transfer of the NO group to cysteine 93 during the R-to-T allosteric transition or via the formation of a stable ferric-iron-nitrosyl hemoglobin (MetHb-NO or HbFe$^{III}$—NO/HbFe$^{II}$—NO$^+$, designated as {FeNO}$^6$ using the Enemark-Feltham notation; Enemark & Feltham, *Coordination Chemistry Reviews* 13:339-406, 1974). (Nagababu et al., *Nitric Oxide* 15:20-29, 2006; Angelo et al., *Proc. Natl. Acad. Sci. USA* 103:8366-8371, 2006). When written as the HbFe$^{II}$—NO$^+$ resonance form, the nitrosonium is emphasized, highlighting potential subsequent transfer to nitrosate cysteine β-93.

In the current study, S-nitrosation was observed, but the putative HbFe$^{III}$—NO intermediate was undetectable. The nitrosation that was observed cannot be explained by allosteric intra-molecular transfer of heme bound NO to the cysteine. In contrast, the nitrite anion was found to directly bind to MetHb, and surprisingly, this results in an electronic configuration that is silent when observed by electron paramagnetic resonance spectroscopy. Based on density functional theory (DFT) calculations, it is proposed that the nitrite bound MetHb exhibits ferrous heme nitrogen dioxide (Fe$^{II}$—NO$_2$·) character that reacts rapidly with NO to form N$_2$O$_3$. In this reaction, deoxyhemoglobin redox cycles and catalyzes the conversion of two nitrite ions into N$_2$O$_3$. These results could solve the mystery of NO escape from the erythrocyte and explain many unusual phenomena observed in the NO-hemoglobin field, such as the nitrosating effects of low NO concentrations (Gow & Stamler, *Nature* 391:169-173, 1998), the link between heme oxidation and SNO-Hb formation (Gow & Stamler, *Nature* 391:169-173, 1998), the identity of a mysterious EPR silent intermediate that can be measured by gasphase reductive chemiluminescence (Nagababu et al., *J. Biol. Chem.* 278:46349-46356, 2003), and the mechanism of nitrite-dependent nitrosation (Nagababu et al., *Nitric Oxide* 15:20-29, 2006; Angelo et al., *Proc. Natl. Acad. Sci. USA* 103:8366-8371, 2006). These experiments therefore reveal a fundamental novel metal and nitrite catalyzed chemical reaction pathway to N$_2$O$_3$ and S-nitrosothiol, which could constitute the basis of in vivo nitrite-dependent nitrosylation. It should be noted that this represents a novel mechanism for both anaerobic and metal catalyzed N$_2$O$_3$ formation and S-nitrosation, and likely represents a major pathway for NO-dependent signaling in a heme rich environment.

The details of this pathway are becoming clear. Nitrite reacts with deoxyhemoglobin to generate MetHb and NO (Equation 1).

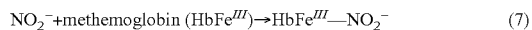

Nitrite (NO$_2^-$)+deoxyhemoglobin (Fe$^{II}$)+H$^+$→NO+ methemoglobin (Fe$^{III}$)+OH$^-$     (1)

Nitrite also binds to MetHb to form MetHb-NO$_2^-$ with a dissociation constant of about 1 mM at neutral pH (Rodkey, *Clin. Chem.* 22:1986-1990, 1976), which in fact was found in this work to be much lower at limiting nitrite concentrations and/or lower pH (Kd=7 μM at pH 6.5).

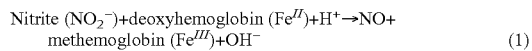

NO$_2^-$+methemoglobin (HbFe$^{III}$)→HbFe$^{III}$—NO$_2^-$     (7)

It has been previously shown that MetHb-NO$_2^-$ is formed in the nitrite-deoxyhemoglobin reaction and herein it is shown that this species is the major intermediate in this reaction. (Huang et al., *J. Biol. Chem.* 280:31126-31131, 2005). Experimental precedence (Nasri et al., *Inorg Chem* 43:2932-2942, 2004; Lim et al., *J Am Chem Soc* 124:9737-9743, 2002; Copeland et al., *J Inorg Biochem* 100:1413-1425, 2006) as well as the DFT calculations indicate that the HbFe$^{III}$—NO$_2^-$ may have either an N-bound or O-bound nitrite. Both forms have high electron affinities and should avidly react with NO via radical-radical like pathway that generates N$_2$O$_3$ and is potentially kinetically competitive with NO reactions with deoxyhemoglobin or oxyhemoglobin.

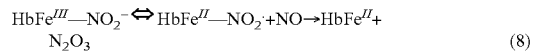

HbFe$^{III}$—NO$_2^-$ ⇔ HbFe$^{II}$—NO$_2$·+NO→HbFe$^{II}$+ N$_2$O$_3$     (8)

Note that, according to the final stoichiometry of this reaction pathway (Equation 9), hemoglobin is catalytic, functioning as an allosterically regulated enzyme that converts two nitrite ions into a molecule of N$_2$O$_3$:

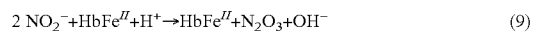

2 NO$_2^-$+HbFe$^{II}$+H$^+$→HbFe$^{II}$+N$_2$O$_3$+OH$^-$     (9)

Although the disappearance of the g=6 paramagnetism is consistent with an altered electronic configuration, the extent of the N-bound nitrite vs. O-bound nitrite and the radical character of HbFe$^{III}$—NO$_2^-$ remains to be completely determined. It is known that MetHb itself is characterized by minor spectral changes as a function of pH, which has been attributed to protein ionizations, likely at the imino N of the proximal histidine (George & Hanania, *Biochem. J.* 52:517-523, 1952; George & Hanania, *Biochem. J.* 55:236-243, 1953). A conjugate acid (+HN) of this imino N is purported to have a pK of 5.1 so that 1 in 25 would be protonated at pH 6.5 and 1 in 200 at pH 7.4. A protonated histidine would pull the electron towards the heme, thus enhancing the HbFe$^{II}$—NO$_2$. character of the O-bound form. The presence of anions has been suggested to reduce the effects of the presence of the +HN (George & Hanania, *Biochem. J.* 52:517-523, 1952; George & Hanania, *Biochem. J.* 55:236-243, 1953), which might explain why the dissociation constant of nitrite-MetHb increased with increasing nitrite concentrations. Further work is required to firmly establish the mechanism of the nitrite concentration-dependent dissociation constant. Even with this +HN configuration, the electron may be mostly on the nitrite. However, the degree to which HbFe$^{III}$—NO$_2^-$ undergoes O-bonding and exhibits HbFe$^{II}$—NO$_2$. character is likely responsible for the observed rapid reactions with NO. Molecular orbital calculations support the idea that there is more than one form of HbFe$^{III}$—NO$_2^-$, and it is likely that these will react with NO at different rates.

Nitrite mediated SNO formation has been observed in vivo (Cosby et al., *Nat. Med.* 9:1498-1505, 2003; Gladwin et al., *Nature Chemical Biology* 1:308-314, 2005; Bryan et al., *Nature Chemical Biology* 1:290-297, 2005). Here (FIGS. 11 and 5F), it is shown that substantial SNO-Hb is formed even when heme is excess to nitrite. One could consider four pathways to SNO formation in the red blood cell with associated export of vasodilatory activity: (1) The nitrite-MetHb+NO mechanism forming N$_2$O$_3$ discussed here (Equations 3 and 8), (2) The nitrite+NO-MetHb mechanism forming N$_2$O$_3$ (Equation 4), (3) the nitrosonium transfer mechanism (Equation 5), and (4) the oxygen transfer mechanism (Equation 6). Data examining oxygen transfer suggest that Nitrite-MetHb does not efficiently transfer oxygen so that this mechanism is unlikely to play a role. Generally, the nitrosonium transfer mechanism is unappealing on theoretical grounds as it seems unlikely that NO$^+$ would nitrosate a specific protein thiol in the presence of 55 M water, and a directed transfer of charged NO$^+$ through water-free protein channel needs to be postulated. FIGS. 1 and 8 show that there is no stable HbFe$^{III}$—NO intermediate, thus limiting the potential for the nitrite+NO-MetHb and nitrosonium transfer mechanisms. However, it is likely that HbFe$^{III}$—NO is formed transiently (lasting only a few seconds) when nitrite reacts with deoxyhemoglobin to form MetHb and NO, as is seen in the case of bacterial nitrite reductases (Gladwin et al., *Nature Chemical Biology* 1:308-314, 2005; Averill & Tiedje, *FEBS Lett.* 138:8-12, 1982; Marti et al., *J Phys Chem B* 108:18073-18080, 2004). One might propose that $N_2O_3$ and the subsequent nitrosation is actually due to the reaction of this transient $HbFe^{III}$—NO with another nitrite anion that may also be present in the heme pocket. However, data showing reduced nitrosation in the presence of KCN (FIG. 7A) argues against this alternative mechanism as the KCN is not likely to have a large effect on the transiently formed $HbFe^{III}$—NO. In addition, data on the rate of reductive nitrosylation (FIG. 4) supports the importance of a $HbFe^{III}$—$NO_2^-$ species. The biggest challenge to the favored Nitrite-MetHb+NO mechanism is that this reaction must compete with the reaction of NO and ferrous hemes in the red blood cell. Molecular orbital calculations suggest that it may only be one electronic configuration such as the O-bound nitrite-MetHb that has radical character that can react quickly enough to be a viable mechanism of $N_2O_3$ formation in a red blood cell. Although the data strongly support the Nitrite-MetHb+NO mechanism, they do not completely rule out the possibility that, under physiological conditions in a red blood cell, other mechanisms (particularly that of involving a transient NO-MetHb reacting with nitrite) may be involved.

B. Molecular Dinitrogen Trioxide ($N_2O_3$) and Nitric Oxide (NO) Bioactivity

The production of $N_2O_3$ by nitrite-heme reactions facilitates export of NO bioactivity from the erythrocyte via multiple pathways. First, $N_2O_3$ is the primary nitrosating species capable of forming red cell S-nitrosothiols, which form as a side product of the nitrite-hemoglobin reaction and may be exportable. It is a small and uncharged molecule, which promotes its concentration and diffusion through the red cell membrane. Finally $N_2O_3$ can homolyze to NO and $NO_2^·$, allowing for NO export (Jeffers et al., *Comp. Biochem. Physiol. A-Mol. Integr. Physiol.* 142:130-135, 2005).

Figure 10:
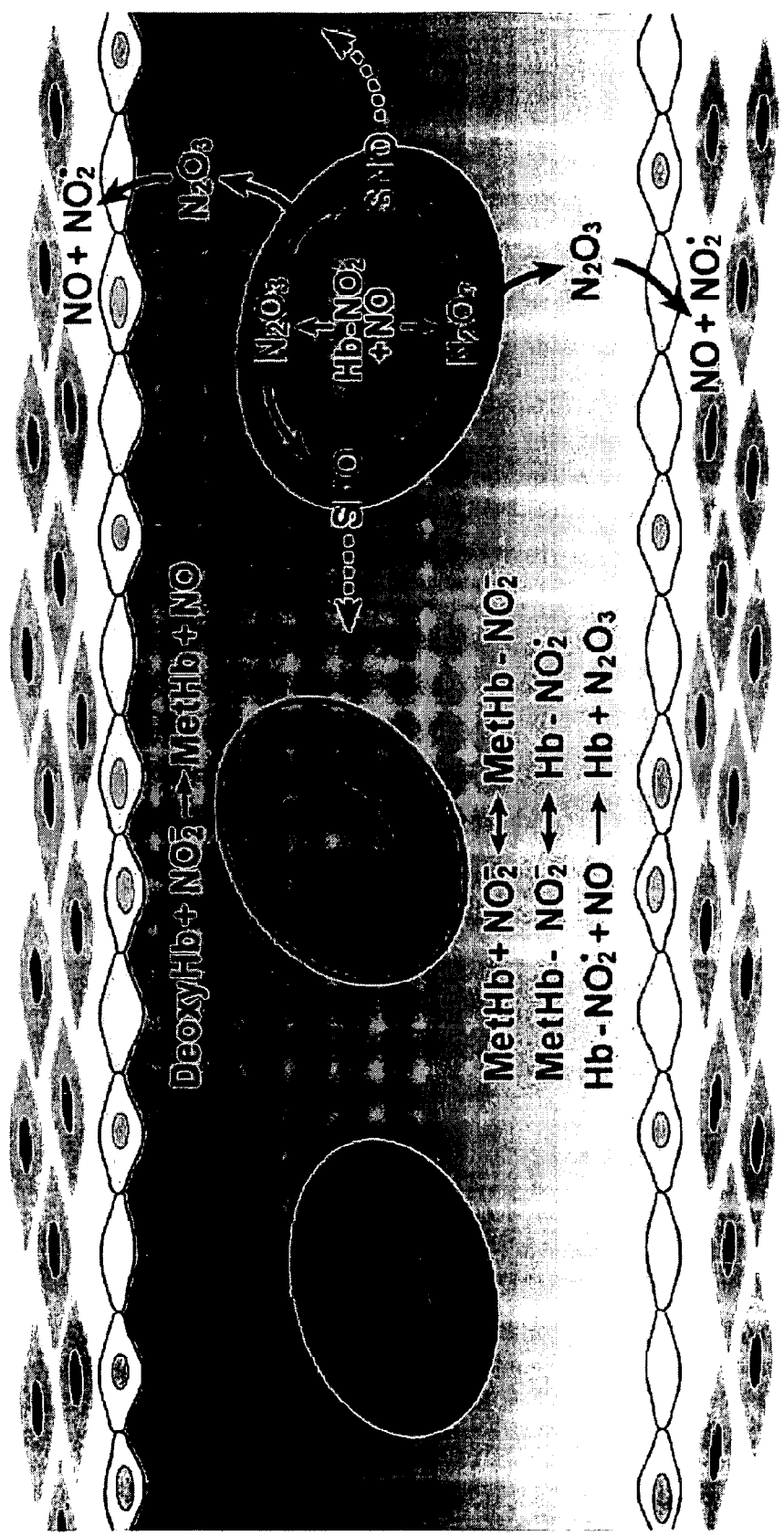
FIG. 10 is a schematic showing a model of nitrite/Hb mediated $N_2O_3$ export and nitrosation. Hemoglobin deoxygenation occurs preferentially at the sub-membrane of the red blood cell as it traverses the arteriole. Nitrite reacts with deoxygenated Hb (deoxyHb) to make MetHb and NO. Much of this NO binds to hemes of deoxyHb or undergoes dioxygenation forming nitrate and MetHb from oxygenated Hb (OxyHb). MetHb binds nitrite to form an adduct with some Fe(II)-$NO_2$ character (Hb-$NO_2^-$). This species reacts quickly with NO, forming $N_2O_3$ which can diffuse out of the red cell, later forming NO and effecting vasodilation and/or forming nitrosothiols (SNO). Low molecular weight nitrosothiols may contribute to exportable vasodilatory activity. The figure is not drawn to scale. Not all reactions (such as hydrolysis of $N_2O_3$) are shown.

These concerted pathways leading from nitrite-heme chemistry to export of NO or other related, potentially vasodilatory species out of the red cell are illustrated in FIG. 10. The lifetime of $N_2O_3$ (1 millisecond) and its diffusion coefficient, D (1000 $\mu m^2/s$), leads to the conclusion that the distance it can diffuse (=$\sqrt{Dt}$) is about 1 $\mu m$. For a RBC that is 2 $\mu m$ high, that means some will get out. In addition, it is quite possible that different isomers of $N_2O_3$ have different and perhaps longer lifetimes further facilitating potential export (Espey et al., *J. Biol. Chem.* 276:30085-30091, 2001; Challis & Kyrtopoulos, *Journal of the Chemical Society-Perkin Transactions* 2 1296-1302, 1978). As hemoglobin deoxygenates from artery to vein the rate of nitrite reduction by deoxygenating hemoglobin increases, producing more NO, which can then react rapidly with MetHb-bound nitrite to form $N_2O_3$. The primary nitrite reductase reaction that generates NO is allosterically regulated and the rate is maximal as hemoglobin desaturates to 50% (at the hemoglobin $P_{50}$), resulting in maximal rates of nitrite reduction to NO as oxygen and pH decrease (Huang et al. *J. Clin. Invest.* 115:2099-2107, 2005). Remarkably, the formation of $N_2O_3$ is also promoted as pH decreases. This may be due to the fact that as proton concentration increases, the affinity of nitrite binding to MetHb is enhanced, the stability of generated $N_2O_3$ increases, and/or the initial reaction of deoxyHb is accelerated due to its requirement of a proton. Once $N_2O_3$ has formed, it may be exported from the red blood cell and homolyze to form NO, thus explaining nitrite mediated vasodilation (Cosby et al., *Nat. Med.* 9:1498-1505, 2003; Crawford et al., *Blood* 107:566-574, 2006).

The efficiency of nitrite reduction and NO release would also be significantly increased if the effective concentrations of the reactants, i.e. nitrite and hemoglobin, are increased at the erythrocyte sub-membrane. A putative nitrite reductase metabolon located within the red cell lipid raft composed of deoxy- and MetHb, an anion exchange protein (for nitrite import into the cell), carbonic anhydrase, aquaporin, and Rh channels (Gladwin et al., *Free Radic Biol Med* 36:707-717, 2004) would effectively concentrate the NO-generating deoxyhemoglobin-nitrite reaction, MetHb bound to band 3, and the necessary reactants (nitrite, protons) near highly hydrophobic channels at the membrane. Because NO and $N_2O_3$ are both lipophilic they could rapidly diffuse out of the cell and thus limit further autocapture. FIG. 10 illustrates the enhancement of this chemistry and concentration of $N_2O_3$ at the red cell membrane.

This mechanism helps explain and unify many of the paradoxical observations in the NO hemoglobin field such as (1) the vasodilatory activity of deoxygenating red cells and hemoglobin solutions in the presence of nitrite (Cosby et al., *Nat. Med.* 9:1498-1505, 2003; Crawford et al., *Blood* 107:566-574, 2006), (2) the nitrosating effects of low concentrations of NO (Gow & Stamler, *Nature* 391:169-173, 1998; Gow et al., *Proc. Natl. Acad. Sci. USA* 96:9027-9032, 1999; Herold & Rock, *J. Biol. Chem.* 278:6623-6634, 2003), (3) the link between heme oxidation and SNO-Hb formation (i.e. effect of ferricyanide on increasing SNO-Hb formation in the presence of nitrite) (Luchsinger et al., *Proc. Natl. Acad. Sci. USA* 100:461-466, 2003; Bryan et al., *Nitric Oxide-Biol Ch* 10:221-228, 2004; Gladwin et al., *J. Biol. Chem.* 277:27818-27828, 2002), (4) the identity of a mysterious EPR silent intermediate that is measurable by gas-phase reductive chemiluminescence (Nagababu et al., *J. Biol. Chem.* 278:46349-46356, 2003), (5) the mechanism of nitrite-dependent nitrosation (Nagababu et al., *Nitric Oxide* 15:20-29, 2006; Nagababu et al., *J. Biol. Chem.* 278:46349-46356, 2003), and (6) the faster than predicted rate of reductive nitrosylation observed by many investigators after addition of NO solutions to hemoglobin (Han et al., *Proc. Natl. Acad. Sci. USA* 99:7763-7768, 2002). This latter effect is related to the suggestion that enhanced formation of $HbFe^{II}$—NO compared to MetHb upon adding NO as a bolus to mixtures of oxygenated and deoxygenated Hb is due to secondary reductive nitrosylation of MetHb formed from NO and oxyhemoglobin (Han et al., *Proc. Natl. Acad. Sci. USA* 99:7763-7768, 2002). As nitrite is commonly present in NO solutions, the reaction of NO with MetHb-$NO_2^-$ would convert MetHb to $HbFe^{II}$—NO.

This nitrite-hemoglobin reaction also provides a novel and kinetically appealing mechanism for S-nitrosothiol formation. If $N_2O_3$ is formed in the nitrite hemoglobin reaction, then in addition to NO and iron-nitrosyl-hemoglobin ($HbFe^{II}$—NO), S-nitrosated products should be detected. During nitrite infusions in humans, both iron-nitrosyl hemoglobin ($HbFe^{II}$—NO) and SNO-Hb form in blood (Cosby et al., *Nat. Med.* 9:1498-1505, 2003). It has also been shown that the reaction of deoxyHb and nitrite forms S-nitrosothiols, including SNO-Hb (Stepuro et al., *Polish Journal of Pharmacology* 46:601-607, 1994; Stepuro et al., *Biochem.-Moscow* 62:960-966, 1997; Luchsinger et al., *Proc. Natl. Acad. Sci. USA* 100:461-466, 2003; Fernandez & Ford, *J Am Chem Soc* 125:10510-10511, 2003; Nagababu et al., *Nitric Oxide* 15:20-29, 2006). The proposed mechanism for SNO-Hb formation is similar to nitrite-catalyzed reductive nitrosylation, in which nitrite reacts with $HbFe^{III}$—NO to form $N_2O_3$ (Fernandez & Ford, *J Am Chem Soc* 125:10510-10511, 2003). However, rather than requiring $HbFe^{III}$—NO to be present at steady state, the reaction depends on HbFe$^{III}$—NO$_2^-$. The existence of this intermediate was obscured in prior studies due to the high NO concentrations used in those studies, which effectively competed with nitrite for binding to MetHb and thus precluded the more rapid nitritecatalyzed reductive nitrosylation (Fernandez & Ford, *J Am Chem Soc* 125:10510-15011, 2003).

These reactions form a general route for NO and S-nitrosative signaling under physiological hypoxia, with a number of heme-globins subserving this function at different oxygen tensions. Hemoglobin would function as a nitrite reductase at oxygen tensions of 60-20 mm Hg, near the hemoglobin P$_{50}$, while myoglobin, neuroglobin and cytoglobin would deoxygenate at oxygen partial pressures below 5-10 mm Hg (Huang et al., *J. Clin. Invest.* 115:2099-2107, 2005). The formation of N$_2$O$_3$ is kinetically appealing as it may compete with NO-heme reactions that otherwise limit nitrosation chemistry. According to this paradigm, nitrite is the major stable NO reservoir in blood and tissues and forms from NO synthase during normoxia (Lauer et al., *Proc. Natl. Acad. Sci. USA* 98:12814-12819, 2001; Shiva et al., *Nature Chemical Biology* 2:486-493, 2006). Nitrite can then be reduced to NO and N$_2$O$_3$ along the physiological oxygen and pH gradient by the heme globins. In this context, the heme globins are allosterically regulated enzymes, which are responsive to tissue metabolism (oxygen and proton levels), and which catalyze the conversion of two nitrite anions into a molecule of N$_2$O$_3$.

These experiments therefore reveal fundamental novel metal and nitrite catalyzed chemical reaction pathways that generate free NO, N$_2$O$_3$ and nitrosothiol. These reactions constitute the basis of in vivo nitrite-dependent hypoxic signal transduction and more globally, a mechanism for NO signaling in a heme-rich environment.

By way of example, in one embodiment two containers of cell free hemoglobin would be prepared: one container (for instance, an I.V. bag) would contain nitrite and ferric methemoglobin (Fe$^{III}$) (at a ratio of less than 1:1); a second container (e.g., I.V. bag) would contain oxyhemoglobin (Fe$^{II}$—O$_2$). The two solutions would be coinfused into a subject at ratios less than 1 part methemoglobin-nitrite to 1 part oxyhemoglobin. After and during the infusion, the oxyhemoglobin would deliver oxygen to the tissue as the oxygen delivery vehicle to form deoxyhemoglobin (Fe$^{II}$). Some of this would react with excess nitrite from the first container to form NO. The methemoglobin-nitrite from that same container would form an intermediate (Fe$^{II}$—NO$_2$ radical); this would react with NO to form N$_2$O$_3$ and Fe$^{II}$(deoxyhemoglobin). The N$_2$O$_3$ would vasodilate and restore NO homeostasis, and the deoxyhemoglobin would now be able to bind oxygen again in the lung. This system thus delivers oxygen, generates N$_2$O$_3$ and NO, and redox cycles to rebind oxygen in the lung.

The composition comprising nitrite and ferric methemoglobin (or other ferric heme protein) would be prepared by addition of sodium nitrite to oxidized heme protein. The oxidation could occur, for instance, by simple autooxidation or by reaction with an oxidant like excess nitrite or ferricyanide. The ratios of nitrite to ferric methemoglobin (or other hemoprotein) would be balanced to form the most nitrite-methemoglobin complex. As this complex is stabilized at decreasing pH, the pH value may be adjusted to a less than physiological level (<pH 7.4) to maximize the formation of intermediate. The two bags would be prepared separately and are expected to be stable as frozen or refrigerated solutions.

The final nitrite-methemoglobin solution is infused at the same time an oxygenated ferrous hemoglobin based blood substitute is infused into the subject. The amount of nitrite-methemoglobin would be delivered to reach a blood concentration of at least 5-10 μM but may be as high as 2 mM. The stroma free hemoglobin based blood substitute would be infused to reach a concentration 1-2 mM (thus the ratio of nitrite-methemoglobin to ferrous oxyhemoglobin would be 1:1 or less).

C. Nitrite Reductase Activity of Hemoglobin as a Systemic Nitric Oxide Generator Mechanism to Detoxify Plasma Hemoglobin Produced During Hemolysis Under physiologic conditions, the experiments described in the Examples below demonstrate that low dose sodium nitrite is a potent arterial vasodilator that increases cardiac performance by direct afterload reduction with mild chronotropic effects. During hemolysis, a consistent U-shaped relationship between the effects of nitrite and cell-free plasma hemoglobin levels was detected across three experimental settings, suggesting an interaction between nitrite and the level of intravascular hemoglobin.

Nitrite reacts with oxy- and deoxy-hemoglobin to form methemoglobin and methemoglobin+nitric oxide respectively (Brooks, *Proc R Soc Med* 123:368-382, 1937; Crawford et al., *Blood* 107:566-574, 2006; Doyle & Hoekstra, *J Inorg Biochem* 14:351-358, 1981; Huang et al., *J Biol Chem* 280:31126-31131, 2005; Huang et al., *J Clin Invest* 115:2099-2107, 2005). During low level hemolysis, these reactions will minimize the amount of oxyhemoglobin available in the plasma that can consume NO (via the dioxygenation reaction) and generate NO by the reaction of nitrite with deoxyhemoglobin. The net result is accentuated vasodilation compared to no hemolysis. At higher levels of intravascular hemolysis, the large amounts of cell-free plasma hemoglobin overwhelms the nitrite reductase reaction of hemoglobin and consumes both the NO formed by nitrite reduction with hemoglobin and endothelial derived NO. The net result is vasoconstriction compared to low level hemolysis and no hemolysis. During a sodium nitroprusside infusion with low level hemolysis and nitrite, the nitrite-oxyhemoglobin reaction minimizes oxyhemoglobin concentration and allows the donated NO from nitroprusside to cause vasodilation. This vasodilation is further accentuated by the production of additional NO from reactions of nitrite with deoxyhemoglobin. At higher level hemolysis, the vasodilatory effects of sodium nitroprusside are attenuated by the high levels of oxyhemoglobin which consume both the NO donated from nitroprusside and the NO generated from the reaction of nitrite with deoxyhemoglobin. During mitochondrial experiments, maximal NO production and accumulation occurred with nitrite and low levels of hemoglobin because the excess heme-groups at higher levels of hemoglobin consumed the NO generated by the nitrite-deoxyhemoglobin reaction leading to decreased NO accumulation.

Traditional NO donors, such as sodium nitroprusside, produce dose-dependent vasodilation that is inhibited by cell-free plasma hemoglobin (Minneci et al., *J Clin Invest* 115: 3409-3417, 2005). In contrast, nitrite led to accentuated vasodilation during low level hemolysis despite the presence of oxyhemoglobin levels sufficient to scavenge any NO that might be formed if nitrite acted as pure NO donor. The vasodilatory effect of nitrite clearly differs from traditional NO donors in the presence of hemoglobin and can in part be explained by the nitrite reductase activity of hemoglobin (Crawford et al., *Blood* 107:566-574, 2006; Huang et al., *J Biol Chem* 280:31126-31131, 2005; Huang et al., *J Clin Invest* 115:2099-2107, 2005). Generation of NO from nitrite and hemoglobin requires both hypoxia and an acidic environment which are present in hypoxic tissues. This allows for maximal NO generation by the deoxyheme-nitrite allosteric reaction as hemoglobin deoxygenates within the circulation.

The studies disclosed herein provide in vivo evidence that hemoglobin possesses a functional nitrite reductase activity. The notable interaction between nitrite and hemoglobin in these studies was markedly different from the behavior of a traditional NO donor, sodium nitroprusside. While the latter was inhibited in a dose dependent manner, the former was potentiated by hemoglobin at concentrations that produced NO in the in vitro mitochondrial NO sensor experiments (see Example 4). Prior studies have examined how NO could be generated from the nitrite reductase activity of hemoglobin and then be able to escape heme autocapture (via equation 1 or an analogously fast reaction with deoxyhemoglobin) (Basu et al., *Nat Chem Biol* 3:785-794, 2007). It was found that nitrite can also bind to methemoglobin to form a nitrite-methemoglobin intermediate that possesses nitrogendioxide-ferrous hemoglobin character. NO that forms from nitrite reduction can react rapidly in a radical-radical reaction with the nitrogen dioxide to form $N_2O_3$ (Basu et al., *Nat Chem Biol* 3:785-794, 2007). $N_2O_3$ is an uncharged, highly lipophilic and diffusible molecule that is more stable than authentic NO. $N_2O_3$ can nitrosate thiols to form vasodilatory S-nitrosothiols, can homolyze back into NO, or can regenerate nitrite. The apparent inhibition of the nitrite effect at higher hemoglobin concentrations in these studies indicate that at least part of the mechanism must involve the regeneration of NO, which can be in part scavenged by excess hemoglobin.

The levels of cell-free plasma hemoglobin in the low hemolysis group of the studies described herein are consistent with the levels observed during sickle cell vaso-occlusive crisis (Kaul & Hebbel, *J Clin Invest* 106:411-420, 2000; Naumann et al., *Am J Clin Pathol* 56:137-147, 1971; Reiter et al., *Nat Med* 8:1383-1389, 2002) and during other clinically relevant human hemolytic conditions such as cardiopulmonary bypass, malarial infection, HUS/TTP, paroxysmal nocturnal hemoglobinuria, allo-immune hemolytic anemia and rhabdomyolysis (myoglobin) (Davis et al., *J Am Soc Nephrol* 10:2396-2402, 1999; Kaul & Hebbel, *J Clin Invest* 106:411-420, 2000; Murakami et al., *Artif Organs* 21:803-807, 1997; Naumann et al., *Am J Clin Pathol* 56:137-147, 1971; Pepper et al., *Free Radic Res* 21:53-58, 1994; Reiter et al., *Nat Med* 8:1383-1389, 2002; Shimono et al., *Asaio J* 43:M735-739, 1997). All of these conditions have now been associated with progressive vasculopathy and pulmonary hypertension and are associated with systemic NO scavenging by plasma hemoglobin (Gladwin et al., *N Engl J Med* 350:886-895, 2004; Minneci et al., *J Clin Invest* 115:3409-3417, 2005; Rother et al., *JAMA* 293:1653-1662, 2005). Furthermore, hemolysis is associated with platelet activation and inhibition of NO-cGMP signaling in platelets (Villagra et al., *Blood* 110:2166-2172, 2007).

These represent processes in which the allosteric nitrite reductase activity of hemoglobin may make nitrite an ideal therapeutic agent to attenuate the effects of accelerated NO scavenging by cell-free hemoglobin released during intravascular hemolysis (Aessopos et al., *Chest* 107:50-53, 1995; Du et al., *Am Heart J* 134:532-537, 1997; Eberhardt et al., *Am J Hematol* 74:104-111, 2003; Kaul et al., *J Clin Invest* 114:1136-1145, 2004; Minneci et al., *J Clin Invest* 115:3409-3417, 2005; Nolan et al., *Blood,* 2005; Reiter et al., *Nat Med* 8:1383-1389, 2002). In these clinical scenarios, the administration of low dose nitrite will have minimal physiologic effects in normal tissues. However, in tissues that have become hypoxic secondary to vasoconstriction from accelerated NO scavenging by cell-free hemoglobin, low dose nitrite may cause vasodilation by: 1) reacting with oxyhemoglobin to form methemoglobin, thereby preventing NO scavenging, and 2) reacting with deoxyhemoglobin to generate NO and methemoglobin. The net effect would be hypoxic vasodilation in local tissues which have become ischemic from the vasoconstrictive effects of accumulating cell-free plasma hemoglobin from ongoing low level intravascular hemolysis.

In addition to low level intravascular hemolysis, the studies described herein indicate that nitrite has a therapeutic role in minimizing the vascular toxicities of more severe episodes of intravascular hemolysis (for example, cell-free plasma hemoglobin levels >50 µM) and the administration of several types of cell-free hemoglobin based blood substitutes (for example, cell-free plasma hemoglobin levels >600 µM) (Doherty et al., *Nat Biotechnol* 16:672-676, 1998; Dou et al., *Biophys Chem* 98:127-148, 2002; Hess et al., *J Appl Physiol* 74:1769-1778, 1993; Hess et al., *Artif Cells Blood Substit Immobil Biotechnol* 22:361-372, 1994; Winslow, *Vox Sang* 79:1-20, 2000). In these clinical scenarios, the ability of nitrite to attenuate the physiologic effects of cell-free plasma hemoglobin will be overwhelmed by the accelerated NO consumption caused by the large amounts of plasma hemoglobin. However, in these scenarios, the affected tissues and organs will subsequently develop areas of hypoxia and acidosis. Within these areas, there will be accelerated reduction of nitrite by deoxygenated cell-free plasma hemoglobin leading to local NO generation and vasodilation. Therapeutic strategies to deliver hemoglobin-based blood substitutes will either require increasing the molar ratio of nitrite:hemoglobin or will require modulating the reaction kinetics by increasing the concentration of nitrite bound to methemoglobin (to facilitate formation of $N_2O_3$) (Basu et al., *Nat Chem Biol* 3:785-794, 2007), decreasing the hemoglobin oxygen affinity (so that there is more deoxyheme to reduce nitrite) or by decreasing the redox potential of the heme-based blood substitute (to increase the reactivity with nitrite).

Therefore, the studies disclosed herein indicate that nitrite will be able to limit organ damage and dysfunction during severe hemolytic episodes and during the administration of hemoglobin based blood substitutes.

The following examples are provided to illustrate certain particular features and/or embodiments. These examples should not be construed to limit the invention to the particular features or embodiments described.

EXAMPLES

Example 1

Materials and Methods

This example describes materials and methods used to carry out Examples 2-4. Although particular examples of materials and methods are described, one will understand that other materials and methods also can be used.

Reagents

All buffers were made with water that had been run through a Milli-RO system followed by a four-cartridge Mill-Q system (Millipore) so that the resistivity of the water was greater than 18 MΩ-cm. All reagents were purchased from Sigma-Aldrich (St. Louis, Mo.) unless otherwise indicated. Red blood cells were obtained by repeated sedimentation/washing in PBS of freshly drawn blood from healthy volunteers. Hemoglobin was prepared from red cells by lysing in excess distilled water and sedimentation followed by freezing in liquid nitrogen for storage as previously described (Geraci et al., *Biol. Chem.* 17:4664-4667, 1969; Huang et al., *Biochim. Biophys. Acta* 1568:252-260, 2001). MetHb was prepared by incubation with a two-fold molar excess of potassium ferricyanide followed by dialysis or sephadex G-25 column filtration. SNO-Hb was prepared as described previously (Gladwin et al., *J. Biol. Chem.* 277:27818-27828, 2002). HbFe$^{II}$—NO was prepared by the addition of NO saturated buffer to deoxyHb as described previously (Huang et al., *Biochim. Biophys. Acta* 1568:252-260, 2001) or by addition of PROLI NONOate (Alexis Biochemicals).

Chemiluminescence Assay Used to Measure S-Nitroso Species

Several assays were considered in performing this study: the tri-iodide (3I) assay, the Cu-cysteine-CO assay (3C), the ascorbic assay/cupric chloride assay and the modified 2C assay. The 3I assay was performed as described previously (Gladwin et al., *J. Biol. Chem.* 277:27818-27828, 2002) using SNO-Hb stabilization solution (containing NEM, ferricyanide—but no cyanide, and DTPA) as previously described (Yang et al., *Free Radic. Res.* 37:1-10, 2003). In all experiments using SNO-stabilization solution, the final concentration of these reagents were the same. The 3C assay was performed as described (Doctor et al., *Proc. Natl. Acad. Sci. USA* 102:5709-5714, 2005), carefully monitoring escape of CO into the laboratory and limiting heating of the nitric oxide analyzer NOA (Sievers; Boulder, Colo.) hopcolite filter. The ascorbic acid/cupric chloride chemiluminescence assay was performed as described previously (Nagababu et al., *Nitric Oxide* 15:20-29, 2006). Absorption spectroscopy, either in the visible or near infra-red (for concentrated samples), was used to determine Hb oxygen saturation or presence of other Hb species by fitting to basis spectra as described previously (Huang et al., *J. Biol. Chem.* 280:31126-31131, 2005).

Figure 13A:
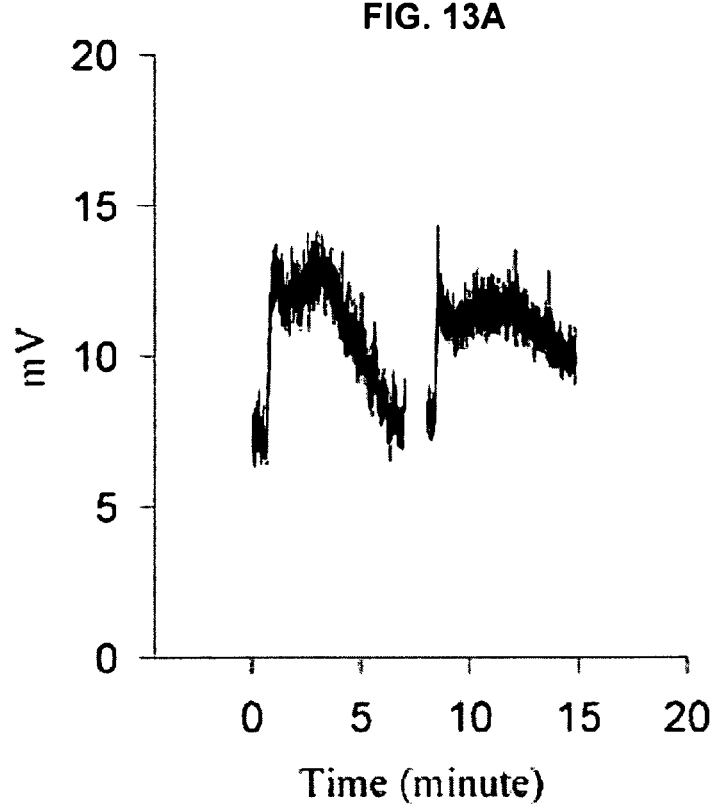
FIG. 13 is a series of graphs showing the detection of HbFe$^{II}$—NO by the 3C assay. (A) 3C assay detects HbFe$^{II}$—NO in the reaction of deoxyHb with sodium nitrite. 5.71 mM deoxyHb (78.3% deoxy) was reacted with 0.985 mM GSH and 0.592 mM sodium nitrite for 30 minute at room temperature and injected into a purge vessel in line with the NOA, and HbFe$^{II}$—NO was measured using the 3C assay with and without treatment with 5 mM HgCl$_2$. The peaks are HgCl$_2$ stable. (B) 3C assay detects pure HbFe$^{II}$—NO. Partially nitrosylated Hb (120 µM Hb with 52% of hemes nitrosylated by excess NO buffer) was injected into the NOA purge vessel with and without prior treatment with HgCl$_2$.
Figure 13B:
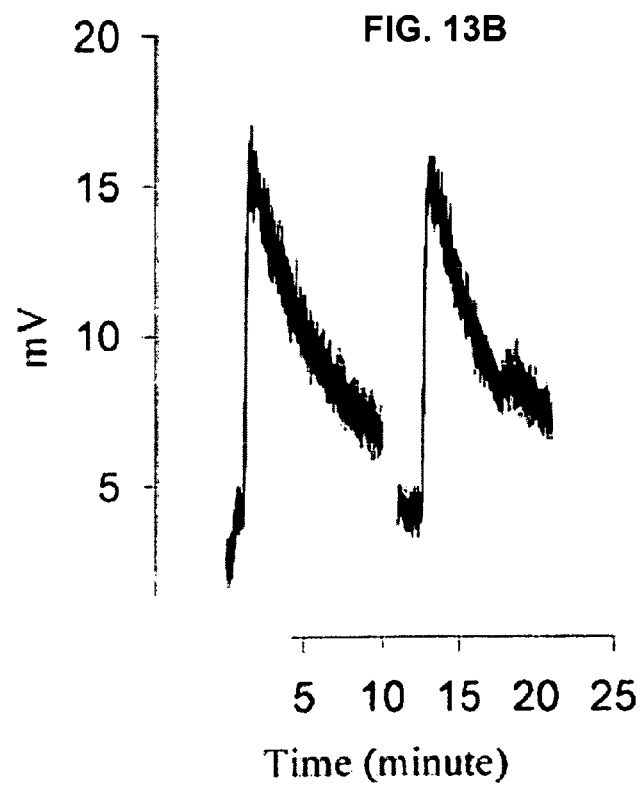

Previously, the inventors have published results from a comparison of the 3C and 3I assays on matched serial dilutions of standard SNO-Hb samples (Huang et al., *Blood* 107:2602-2604, 2006). The two assays were very consistent with each other, with a correlation coefficient of r=0.999258, p<0.001. The 3C assay has the advantage that no chemical treatment or Sephadex G25 column separation is required to remove nitrite. When the 3C assay was applied to the study of SNO-Hb formation in the Hb/nitrite reaction, very large signals were observed. However, control experiments using HbFe$^{II}$—NO (FIG. 13) demonstrated that these large signals were actually due to iron nitrosyl species, not SNO-Hb. Thus, contrary to the conclusion of a previous study (Doctor et al., *Proc. Natl. Acad. Sci. USA* 102:5709-5714, 2005), the 3C assay has some sensitivity to HbFe$^{II}$—NO$^{§§}$. However, as previously noted (Doctor et al., *Proc. Natl. Acad. Sci. USA* 102:5709-5714, 2005), the presence of nitrosothiols can be verified by subtracting the difference between signals from samples incubated with Hg from those that are not exposed to Hg. Although the 3C appeared to be a workable method, the fact that it was necessary to look for a small (possibly null) signal in the background of a relatively large one (due to the HbFe$^{II}$—NO) was less than optimal. Thus, a modified 2C assay was developed and employed that does not detect HbFe$^{II}$—NO.

Figure 14A:
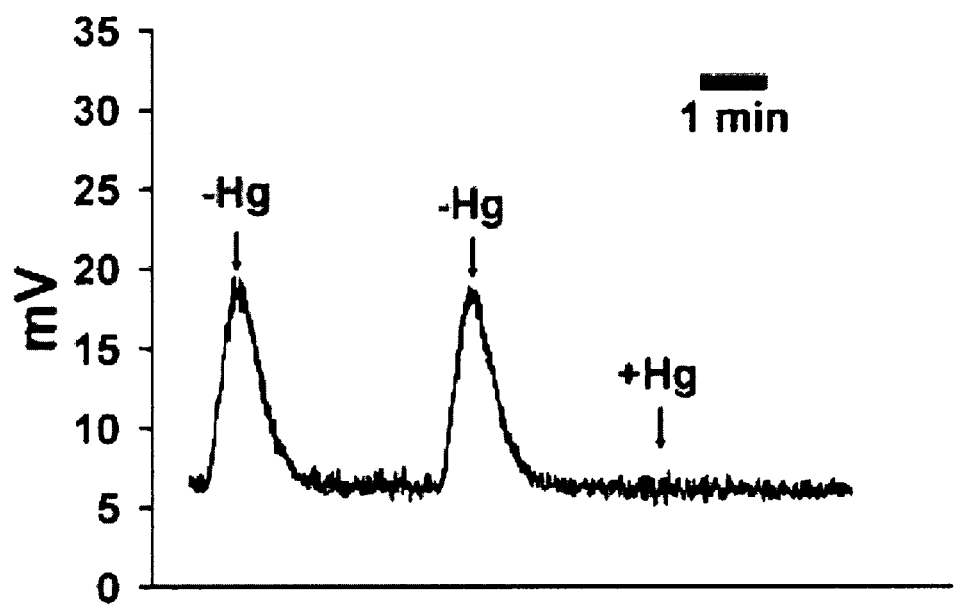
FIG. 14 is two graphs showing the modified 2C assay. (A) GSNO standard. GSNO (3 µM) measured by direct injection into 2C assay, with (+Hg) or without (−Hg) treatment with 5 mM HgCl$_2$. (B) SNO-Hb standard. The SNO-Hb standard was diluted into excess Hb to a final concentration of 5 mM heme and 15 µM SNO, treated with SNO-stabilization solution, passed through two consecutive G-25 columns, and finally analyzed by the 2C assay.
Figure 14B:
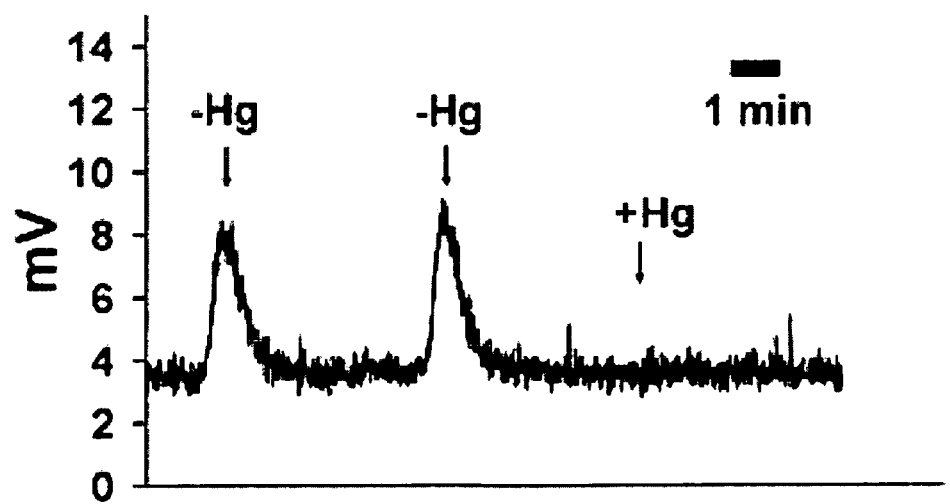

In order to avoid detection of HbFe$^{II}$—NO in the 2C assay, samples were pretreated with potassium ferricyanide (as part of the SNO stabilization solution—see above) oxidizing the Hb to MetHb, which both eliminates HbFe$^{II}$—NO and also makes the use of CO unnecessary as MetHb does not capture NO effectively. The modified 2C assay used here to measure SNO is a variation of the 2C assay previously described (Fang et al., *Biochem. Biophys. Res. Commun.* 252:535-540, 1998). The modification involves treatment with SNO stabilization solution (10 mM NEM, 4 mM ferricyanide, 100 μM DTPA, final concentrations; Yang et al., *Free Radic. Res.* 37:1-10, 2003) for 0.5 to 1 hour. The ferricyanide oxidizes both HbFe$^{II}$ and HbFe$^{II}$—NO to MetHb to prevent autocapture of NO released from SNO-Hb and eliminates the iron-nitrosyl-hemoglobin signal; the NEM blocks free thiols to prevent artifactual SNO-Hb formation. After incubation with SNO stabilization solution, the sample was run through two G-25 Sephadex columns to remove excess ferricyanide. Validation of the modified 2C assay included verification that the assay does not give a signal for HbFe$^{II}$—NO or NEM blocked Hb. Similar tests were performed for the 3C and 3I assays and in all cases HbFe$^{II}$—NO was made by adding NO saturated buffer to excess Hb so that the Hb becomes partially nitrosylated (with no free NO). NEM treatment was performed on oxygenated samples and verified using the Ellman's reagent for free thiols (Ellman et al., *Biochem. Pharmacol.* 7:88-95, 1961). In order to ensure that no false positive SNO-Hb signal is given from HbFe$^{II}$—NO, the modified 2C assay was performed on HbFe$^{II}$—NO prepared by adding NO buffer to excess deoxyHb. HbFe$^{II}$—NO did not produce a significant signal whether the samples were pre-treated with NEM before deoxygenation or not. It was also observed that EPR signals from HbFe$^{II}$—NO completely disappear after incubation with SNO stabilization solution. FIG. 14 shows typical signals obtained from standard samples using the modified 2C assay.

Nitrosation of small molecular weight molecules incubated together with nitrite and Hb or RBCs (such as GSH) was assayed by filtering out the protein using a Sentricon filter (Millipore, Billerica, Mass.). The filtrate was then injected directly into the NOA using the 2C assay.

Absorption Spectroscopy

Figure 15A:
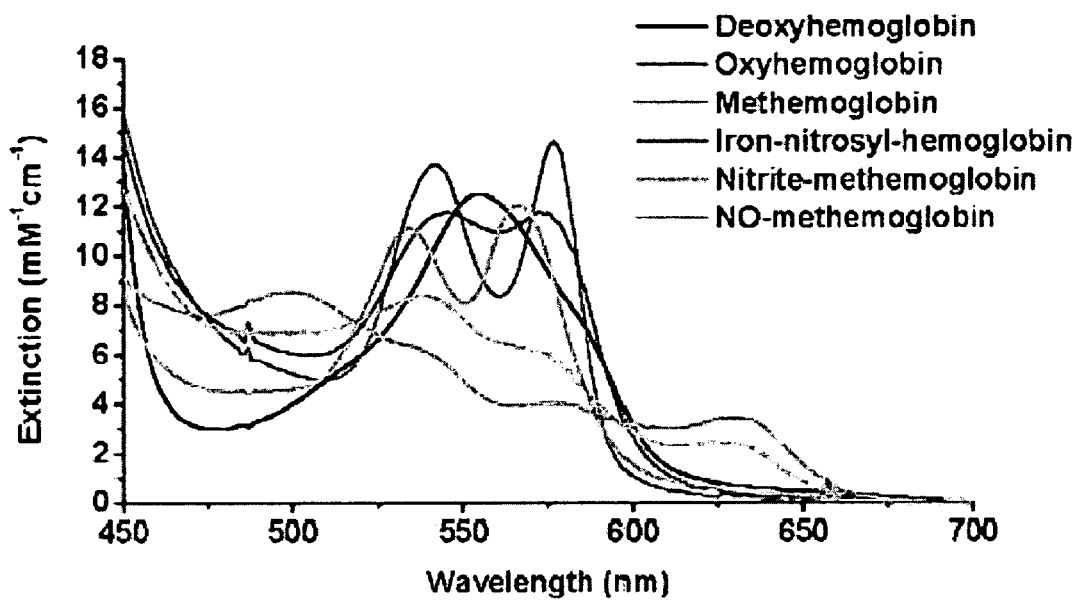
FIG. 15 is a series of graphs showing the human hemoglobin absorption spectroscopy standard spectra. (A) Standard reference spectra used as a basis for deconvoluting and fitting data obtained by absorption spectroscopy measurements of hemoglobin reaction kinetics. (B) Selected absorbance spectra of the reaction depicted in FIGS. 1A-C (250 µM deoxyHb and 125 µM nitrite) taken at the indicated time points during the reaction. Raw spectra were corrected for scatter by subtracting the absorbance at 700 nm. Times are shown in minutes. (C) Comparison of raw spectroscopic data obtained by UV-V is spectroscopy during the reaction shown in FIGS. 1A-C to theoretical spectra calculated based on the concentrations of heme species derived by least-squares deconvolution and the standard spectra of these species (shown in FIG. 1A). The only assumption made in these deconvolutions is that no colored species have been left out that are likely to be present in the reaction. In some ways, this method is equivalent to determining (for example) the concentration of MetHb in a mixture of MetHb and OxyHb by using the known extinction coefficients of the two species and the absorbance of the mixture at two wavelengths. This two wavelength procedure results in two linear equations (one at each wavelength) and two unknowns (the concentration of MetHb and OxyHb). In the method described herein, a similar linear equation is applied at each wavelength and solved for the concentration of each species. The system of linear equations is over-determined, so a least squares fit is performed to obtain the best value for the concentration of each species at each time point.
Figure 15B:
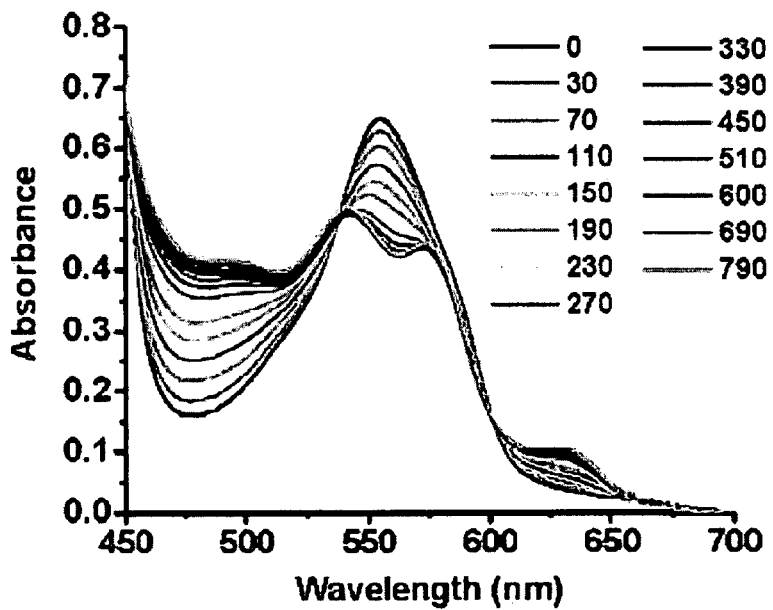
Figure 15C:
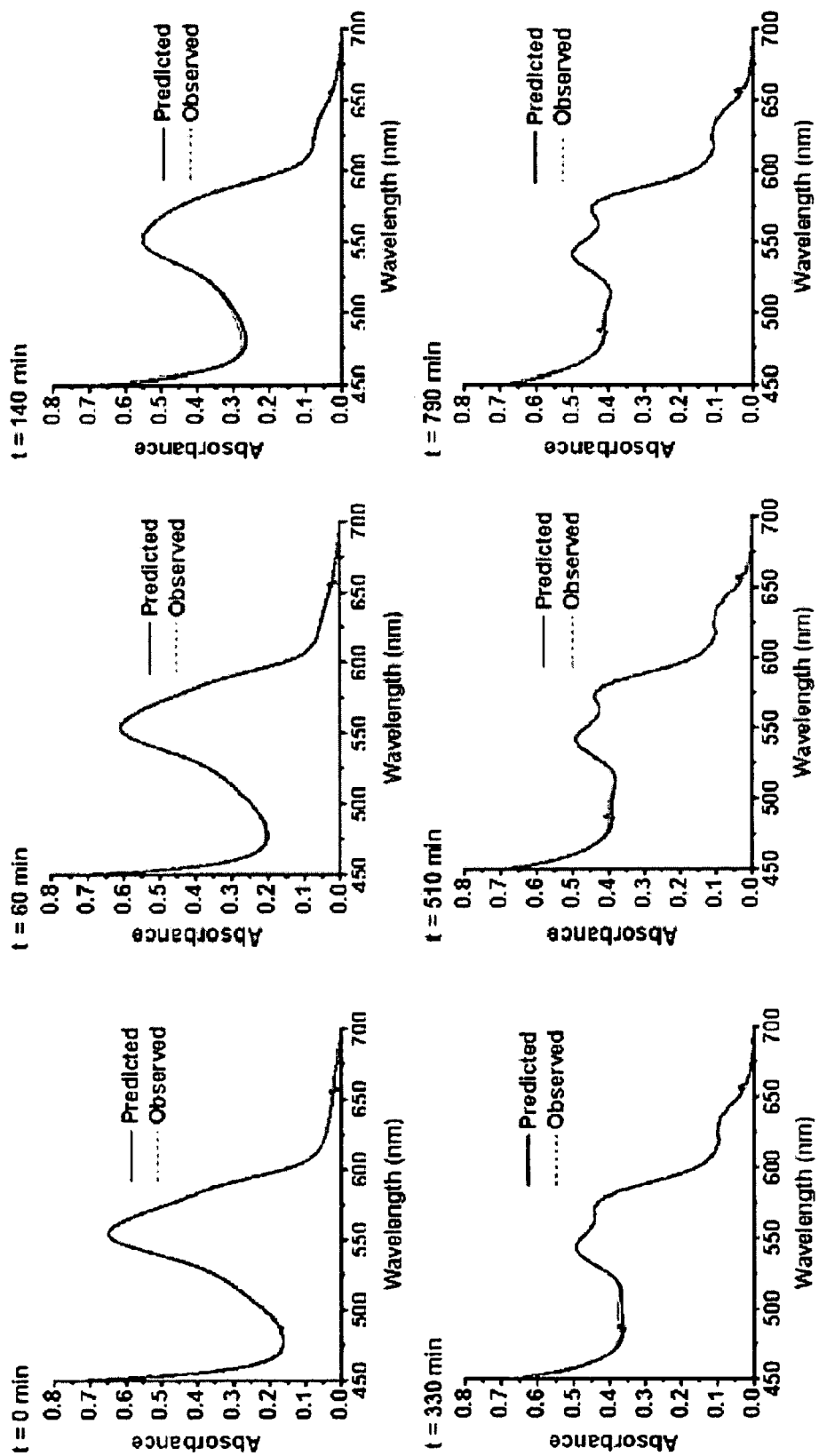

Spectra were taken on either Cary 50 spectrometers or a Hewlett Packard 8453 UV-Vis spectrophotometer. Oxygen leakage into the system was prevented by application of positive helium, argon or nitrogen pressure without a channel for gas escape. Spectral deconvolution was performed by a least squares fit using basis spectra as described previously (Huang et al., *J. Biol. Chem.* 280:31126-31131, 2005). At each time point, the measured absorption spectrum is fit to a linear combination of normalized pure species, the basis spectra. Basis spectra used are presented in FIG. 15. No kinetic models are invoked in this procedure. Stopped-flow absorption was carried out using an OLIS RSM 1000 spectrometer coupled to a Molecular Kinetics three syringe mixer. Kinetics from stopped-flow were analyzed by singular value decomposition and global analysis fitting to a single exponential process.

Electron Paramagnetic Resonance Spectroscopy

EPR spectroscopy was performed as described previously (Azarov et al., *J. Biol. Chem.* 280:39024-39032, 2005). HbFe$^{II}$—NO was measured by EPR using a Bruker EMX 10/12 spectrometer operating at 9.4 GHz, 5-G modulation, 10.1-milliwatt power, 655.36-ms time constant, and 167.77-s scan or 327.68-ms time constant and 83.89-s scan over 600 G at 110 K. MetHb was measured by EPR (at low field using 15-G modulation, 10.1-milliwatt power, 81.92-ms time constant, and 41.94-s scan over 700 G) at 4 K using liquid helium. The concentrations of Hb species measured by EPR were determined by performing the double integral calculation and comparing to standard samples.

EPR spectroscopy was used to determine the dissociation constant of nitrite bound MetHb at various concentrations of nitrite. The dissociation constant is given by $K_d$=[MetHb][nitrite]/[MetHb-nitrite]. Known amounts of MetHb ([MetHb]$_i$—also confirmed by EPR) were mixed with known amounts of nitrite ([nitrite]$_i$). EPR spectra were used to determine [MetHb] after nitrite addition (this concentration is the unliganded MetHb present in the expression for $K_d$). Nitrite bound MetHb was assumed to be completely EPR silent so [MetHb-nitrite] was determined from the difference of [MetHb]$_i$–[MetHb].

Generation and Detection of Gas-Phase $N_2O_3$ by Reductive Nitrosylation

All reactions were carried out anaerobically and in the dark at 25° C., inside a purge vessel in line with the NO gas analyzer (NOA; Sievers NO analyzer; GE Analytical Instruments). 0.001% anti-foam B emulsion in 0.1 M phosphate buffer, pH 7.4, was purged with helium gas for a minimum of 30 minutes before the addition of 75 µM MetHb. 1 mM nitrite was added 4 minutes after MetHb and allowed to equilibrate with the MetHb for another 4 minutes prior to injection of 5 µM Proli NONOate (Alexis Biochemicals; a 5 mM Proli NONOate stock solution in 0.01 M NaOH was used; equivalent to 10 µM NO). Parallel control reactions were carried out that excluded either nitrite or Proli NONOate. The reaction was stopped 20 minutes after injection of the last reagent. All reagents were thoroughly deoxygenated prior to injection. The trap vessel contained 10 mL of 5 mM reduced L-glutathione and 100 µM diethylenetriamine-pentaacetic acid (DTPA) in 0.01 phosphate buffered saline (PBS), pH 7.4. When the reaction was terminated, the trap solution was divided into 1 mL aliquots and immediately frozen at –80° C. for subsequent analysis. One aliquot of the trap solution was analyzed by absorbance spectroscopy to ensure absence of trap solution contamination by MetHb from the purge vessel. The reaction solution from the purge vessel was collected and passed through a Sephadex G-25 column (Amersham Biosciences) to remove excess nitrite, the hemoglobin quantified by absorbance spectroscopy, aliquoted into 1 mL fractions, and frozen at –80° C. for subsequent analysis. All aliquots were stored in dark (foil-wrapped) Eppendorf tubes until analyzed in triplicate for their nitrosothiol and iron-nitrosyl-heme content using ozone-based chemiluminescence assay as previously described. Sample analysis was subsequently performed using reductive chemiluminescence (Gladwin et al., *J. Biol. Chem.* 277:27818-27828, 2002). 1 mL aliquots of each sample were reacted with either 100 µL PBS (2 minutes) followed by 100 µL 5% acidified sulfanilamide in 1 N HCl (5 minutes) or with 100 µL 50 mM mercuric chloride in PBS (2 min) followed by 100 µL 5% acidified sulfanilamide in 1 N hydrochloric acid (5 min) prior to injection into a purge vessel containing 6 mL tri-iodide solution (2 g potassium iodide and 1.3 g iodine dissolved in 40 mL water and 140 mL acetic acid) in line with the NOA.

Statistical Analysis

Data from all gas-phase $N_2O_3$ generation experiments was analyzed using GraphPad Prism 4.0 (GraphPad Software Inc., San Diego, Calif.) and is reported as mean±S.E.M. Wilcoxon matched pairs test was used to compare average values of GSNO, SNOHb, and iron nitrosyl Hb with and without nitrite addition for nine sets of experiments. Results were considered statistically significant with $p<0.05$.

DFT Calculations

DFT calculations were carried out with the OLYP (Handy & Cohen, *Molecular Physics* 99:403-412, 2001; Lee et al., *Physical Review B* 37:785-789, 1988) generalized gradient approximation (GGA), triple-ζ plus polarization Slater-type orbital basis sets, and a fine mesh for numerical integration of the matrix elements. The results were checked against a number of other functionals and found not to vary to any significant extent. The ADF 2006 (Scientific Computing and Modeling, Amsterdam) program system was used for all calculations.

Animal Studies

Thirty-two purpose-bred beagles (12-28 months, 9-12 kg) were studied. All procedures were performed after inducing anesthesia with halothane (1-4%), and initiating mechanical ventilation. Upon completion, the halogenated gas was terminated and 100% oxygen administered until the dog emerged from anesthesia and was extubated. Subsequently, the animal was breathing room air spontaneously and was sedated throughout the duration of the experiments. Continuous infusions of medetomidine (sedation; 2-5 mcg/kg/h) and fentanyl (analgesia; 2.5-20 mcg/kg/h) were initiated post-extubation and maintained for the study duration. Animals were monitored continuously and signs of pain and distress were evaluated immediately and the infusions adjusted appropriately.

Nitrite Infusion

Using pilot experiments to characterize beagle-specific pharmacokinetics of sodium nitrite, an infusion of 165 mg of sodium nitrite over 6 hours (27.5 mg/h) was chosen to be administered during the study to reach a targeted plasma nitrite concentration between 15 and 20 µM. Animals randomized to groups not receiving sodium nitrite received an equivalent rate and total volume infusion of 0.9% NaCl (normal saline) to serve as a placebo control.

Water-Infusion Intravascular Hemolysis Model

A previously developed and validated canine model of water-infusion induced intravascular hemolysis was used in this study (Minneci et al., *J. Clin. Invest.* 115:3409-3417, 2005). Water-induced hemolysis produces direct intravascular hemolysis thereby maintaining the same intravascular concentration of total hemoglobin during hemolysis, while altering the distribution of hemoglobin between the red cell and plasma compartment. In this model, a six-hour infusion of water (rate: 16 ml/kg/h) produces clinically relevant levels of cell-free plasma hemoglobin (20-300 µM heme), simulating an acute hemolytic episode. The extent of hemolysis increases over time, allowing for a graded physiological assessment of vasomotor dysfunction as plasma hemoglobin levels rise. The final levels of plasma hemoglobin would be analogous to those achieved following coronary bypass surgery or a hemolytic crisis induced by paroxysmal nocturnal hemoglobinuria or acute immune mediated hemolysis.

Control animals received an equivalent rate and total volume infusion of 5% Dextrose (D5W) to account for any potential hypotonic and volume effects of the water infusion on hemodynamics. A full-factorial study design was used with four groups of animals receiving D5W, D5W+intravenous sodium nitrite, Water, or Water+intravenous sodium nitrite. This design allows for determining the physiologic effects of a sodium nitrite infusion, the physiologic effects of intravascular hemolysis (water) and to assess for an interaction between nitrite and hemolysis. Specifically, the interaction statistic tests if the effects of nitrite and hemoglobin are influenced by the nitrite reductase activity of cell-free plasma hemoglobin. Paired experiments were performed in twenty animals (5 per group). In the first week, all animals underwent a baseline study and received a D5W infusion (16 ml/kg/h) through a central venous catheter to determine the physiologic effects of the volume load in each animal. The D5W infusion does not cause hemolysis; it allows each animal to serve as its own control for the effects of a hypotonic volume load in the model. One week later, the animals underwent an intervention study and were randomized to receive a 6-hour infusion through a central venous catheter of either D5W (16 ml/kg/h), D5W (16 ml/kg/h)+nitrite (27.5 mg/h), Water (16 ml/kg/h) or Water (16 ml/kg/h)+nitrite (27.5 mg/h).

This paired experimental design allows for minimization of animal-to-animal variability by calculating the change for each measurement performed in each animal during the baseline and intervention studies. Subsequent analyses calculate the differences across treatment groups by subtracting the previously calculated differences within animals (from baseline to intervention study) in one treatment group from another treatment group (i.e. comparison of the differences of the differences). This design allows for analysis of the effects of hemolysis, the effects of sodium nitrite, and detection of any interaction between the two.

Preliminary analysis demonstrated a wider range of hemolysis than previously described secondary to the addition of salt-based therapies (sodium nitrite or sodium chloride) that affected the rate of hypotonic erythrocyte lysis. In these experiments, the 6-hour water infusions produced low rate hemolysis in 50% of the animals and rapid rate hemolysis in 50% of the animals. This created two equal sized groups of animals with either low or high levels of cell-free plasma hemoglobin respectively. Both groups had peak cell-free plasma hemoglobin levels that continued to be within a clinically relevant range (20-200 µM heme). Preliminary data analyses also suggested a possible interaction between sodium nitrite and hemolysis that was dependent on the amount of hemolysis (heme concentration <25 µM vs. >25 µM). Subsequently, the variation in hemolytic rate and this potential interaction was accounted for by calculating the number of animals needed to determine if there was an interaction between nitrite and hemolysis level (assuming a 1:1 ratio of low:high rate hemolysis in animals receiving a water infusion) and included the level of hemolysis in the final data analysis. The necessary additional paired experiments were then performed using the same treatment regimens with a weighted randomization scheme to the following groups: D5W+nitrite (n=2), water (n=5) or water+nitrite (n=5). Overall, these studies utilized thirty-two animals.

Sodium Nitroprusside Challenge

In order to determine the vascular responsiveness to exogenous NO in the presence and absence of hemolysis and sodium nitrite, all animals received a 20 minute infusion of escalating doses of sodium nitroprusside, a direct NO donor, (1, 3. 9 and 27 mcg/kg/min) at 5 minute intervals prior to concluding the study. These experiments allowed for comparison of a "traditional" NO donor with nitrite to determine if the observed nitrite effects (i.e. hemoglobin-based nitrite reduction) were distinct from a pure NO vasodilatory effect.

Data Collection

Femoral arterial (20-gauge) and external jugular venous (8 French) catheters (Maxxim Medical, Athens, TX) were placed percutaneously under anesthesia using sterile technique. Mean arterial pressure (MAP) and heart rate (HR) were obtained from the femoral artery catheter tracing. Additionally, a pulmonary artery thermodilution catheter (7 French, Abbott Critical Care, Chicago, Ill.) was introduced through the external jugular vein catheter in order to measure cardiac output (CO), pulmonary artery pressure (PAM), pulmonary artery occlusion pressure (PAOP), and central venous pressure (CVP). At the end of the first week's fluid control experiments, all catheters were removed and the animals recovered. At the end of the second week's intervention experiments, all animals were euthanized.

Hemodynamic measurements (MAP, CVP, PAP, CO, and PCWP) and laboratory studies (hematocrit (Hct), hemoglobin (Hb), serum chemistries, arterial blood gas analysis (ABG), spectrophotometric-based quantification of cell-free hemoglobin concentration and chemiluminescence-based assays of nitric oxide consumption and nitrite levels) were obtained at 0, 1.5, 3.0, 4.5, and 6.0 hour time points. Hemodynamic measurements were also obtained at the end of each dose of sodium nitroprusside.

Plasma Nitrite and Hemoglobin Assays

Plasma nitrite levels were measured by I3-based chemiluminescent assay as previously described using the NO analyzer (Seivers, Model 280i NO analyzer, Boulder, Colo.) (Yang et al., *Free Radic. Res.* 37:1-10, 2003). Total plasma hemoglobin concentration (expressed in terms of heme groups; division by four gives hemoglobin concentration) was measured by visible absorbance spectrophotometry (HP8453 UV-Vis Diode Array Spectrophotometer, Hewlett Packard). The concentration of oxyhemoglobin and methemoglobin were analyzed by deconvoluting the spectrum into components from basis spectra of canine hemoglobin in PBS buffer using a least square method as previously described, with subtraction of background plasma scattering (Huang et al., *Biochim. Biophys. Acta.* 1568:252-260, 2001).

In-Vitro Mitochondrial Respiration Experiments

Male Sprague Dawley rats (175-250 g) were used in accordance with the ACUC of the National Heart Lung Blood Institute. Liver mitochondria were isolated by differential centrifugation in buffer consisting of Sucrose (250 mM), Tris (10 mM), and EGTA (1 mM), as previously described (Shiva et al., *Circ. Res.* 100:654-661, 2007). Mitochondrial respiration was measured by suspending isolated mitochondria (2 mg/ml) in respiration buffer (120 mM KCL, 25 mM Sucrose, 10 mM HEPES, 1 mM EGTA, 1 mM $KH_2PO_4$, 5 mM $MgCl_2$) in a stirred sealed chamber fit with a Clark-type oxygen electrode (Instech Corp.) connected to a data recording device (DATAQ systems). Mitochondria were supplemented with succinate (15 mM) and ADP (1 mM) to stimulate respiration.

In experiments testing the effects of nitrite and hemoglobin, sodium nitrite and human purified oxyhemoglobin (Ignarro et al., *Proc. Natl. Acad. Sci. U.S.A.* 84:9265-9269, 1987) were incubated with the mitochondria at the beginning of the experiment (Shiva et al., *Circ. Res.* 100:654-661, 2007). In this experimental system, the rate of oxygen generation from the added hemoglobin is less than the rate of oxygen consumption by the mitochondria so that the oxygen increase in the system after hemoglobin addition (20 µM) is not detected by the oxygen electrode and not observed in the raw trace unless high concentrations of hemoglobin are added, in which case a transient increase in the oxygen level may be detected. Note that in this system the chamber is opened to air and oxygen is diffusing into the system as well, but the rate of oxygen diffusion into the system is less than the rate of oxygen consumption by the mitochondria. Only after mitochondrial inhibition do the oxygen levels rise to detection by electrode.

Statistical Analysis for Animal Studies

Data were analyzed using an ANOVA, with main effects for study (baseline and intervention), hemolysis (0 µM (D5W), <25 µM Heme, >25 µM Heme), nitrite, time, and animal (Minneci et al., *J. Clin. Invest.* 115:3409-3417, 2005). Two- and three-way interactions were included in the model. Analysis of responses to sodium nitroprusside were performed using ANOVA on percent change in hemodynamic variables with increasing dose in the intervention study with main effects for hemolysis, nitrite, nitroprusside dose and animal. Two-way interactions were included in the model. All values are depicted in the figures as mean +/− SE and all hemoglobin concentrations are expressed in terms of heme groups.

Example 2

Catalytic Generation of $N_2O_3$ by a Concerted Nitrite Reductase/Anhydrase Activity of Hemoglobin This example describes the hemoglobin-catalyzed generation of $N_2O_3$, a gaseous nitric oxide (NO) precursor with the capacity to escape a heme-rich environment and subsequently deliver vasodilatory NO to tissues.

Identification of Nitrite-Bound Methemoglobin ($Fe^{III}$—$NO_2^-$) During the Reaction of Nitrite with deoxyHb The anaerobic reaction of deoxyhemoglobin with nitrite is an allosteric second order reaction with a bimolecular rate constant that ranges from $0.12\ M^{-1}s^{-1}$ at the beginning of the reaction (T-state) to a maximum of $6\ M^{-1}s^{-1}$ later in the reaction (R-state) at 25° C. and pH 7.4 (Huang et al., *J. Clin. Invest.* 115:2099-2107, 2005). As predicted by Equations 1 and 2, an equal ratio of MetHb to iron-nitrosyl-hemoglobin was measured at the end of the reaction.

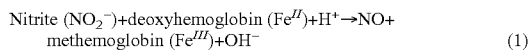
(1)

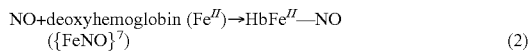
(2)

However, others have observed that more MetHb than iron-nitrosyl-hemoglobin is made in the course of this reaction, particularly at low nitrite to hemoglobin ratios, which they attributed to the formation of an NO-MetHb ($Fe^{III}$—NO) intermediate (Angelo et al., *Proc. Natl. Acad. Sci. USA* 103: 8366-8371, 2006; Nagababu et al., *J. Biol. Chem.* 278:46349-46356, 2003). This intermediate possesses nitrosonium ion character through the resonance form $NO^+$-ferrous hemoglobin ($Fe^{II}$—$NO^+$, designated as $\{FeNO\}^6$ using the Enemark-Feltham notation; Enemark & Feltham, *Coordination Chemistry Reviews* 13:339-406, 1974) that could potentially nitrosate thiols to make S-nitrosothiols (SNO). Consistent with this hypothesis, the nitrite reaction with deoxyhemoglobin forms S-nitroso-hemoglobin (SNO-Hb), although the yields and conditions necessary for this chemistry have been elusive (Cosby et al., *Nat. Med.* 9:1498-1505, 2003; Luchsinger et al., *Proc. Natl. Acad. Sci. USA* 100:461-466, 2003).

Figure 1A:
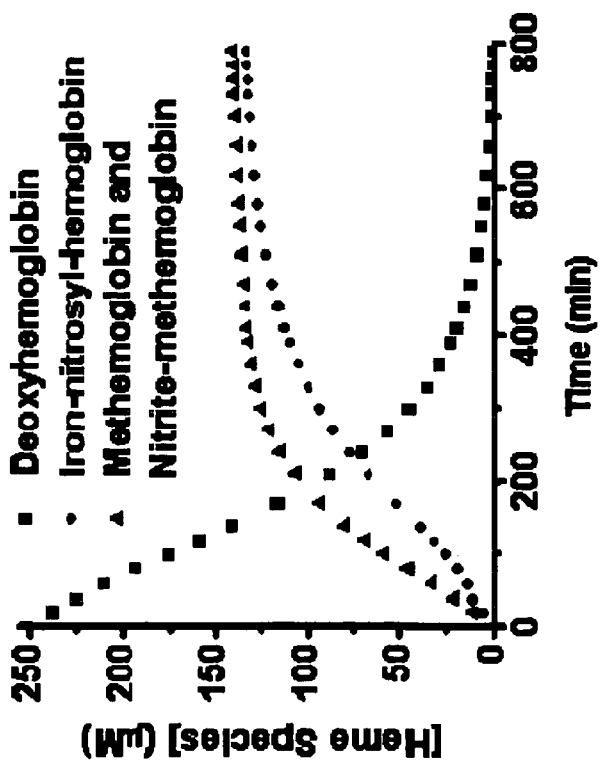
Figure 1D:
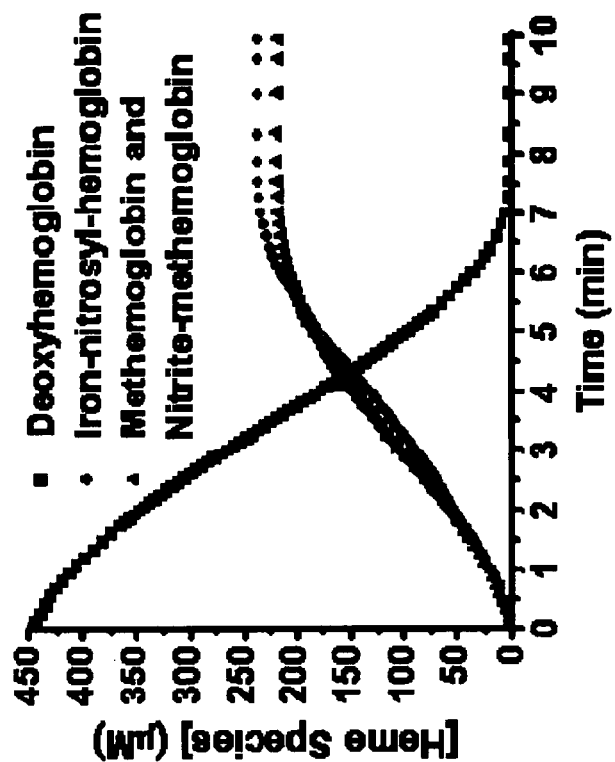

As NO-MetHb has a clearly distinguishable visible spectrum, it should be possible to determine if this species is formed as a significant intermediate using least-squares deconvolution of visible spectra take during the time course of the reaction between nitrite and deoxyHb. In FIGS. 1A (2-fold excess in deoxyhemoglobin) and 1D (11-fold excess in nitrite), using reference spectra with and without the NO-MetHb species in the reference standard, the derived yields and residuals were compared over time, assuming that the smallest residual was due to inclusion of all proper heme species in the deconvolution. Five basis spectra were used; they included deoxyhemoglobin, MetHb, and iron-nitrosyl-hemoglobin species, while nitrite-MetHb (formed when nitrite binds to MetHb: MetHb-$NO_2^-$ or HbFe$^{III}$—$NO_2^-$) and NO-MetHb (putative intermediate) were added in isolation and together to discern their respective contributions to the reaction constituents.

Figure 1C:
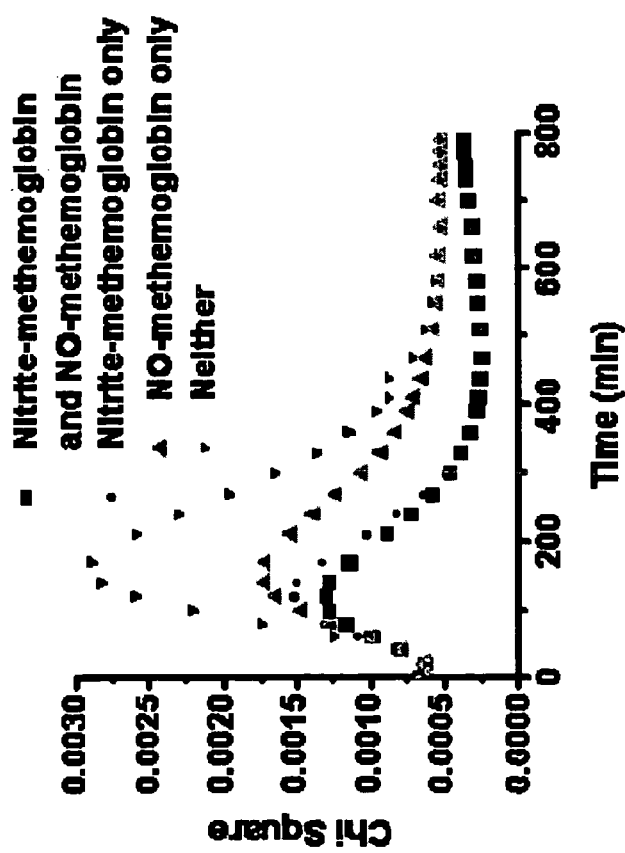
Figure 1E:
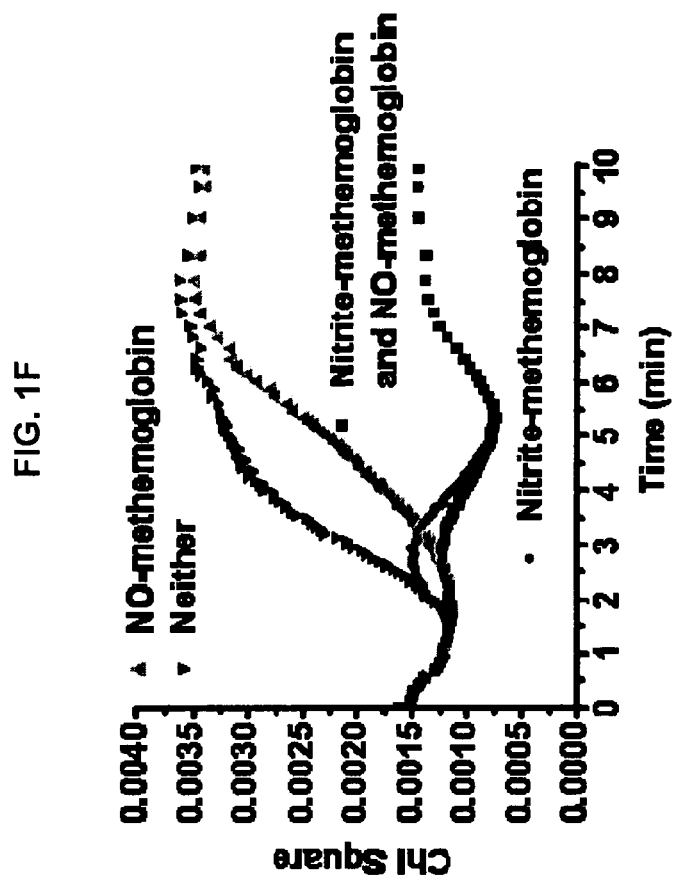
Figure 1F:
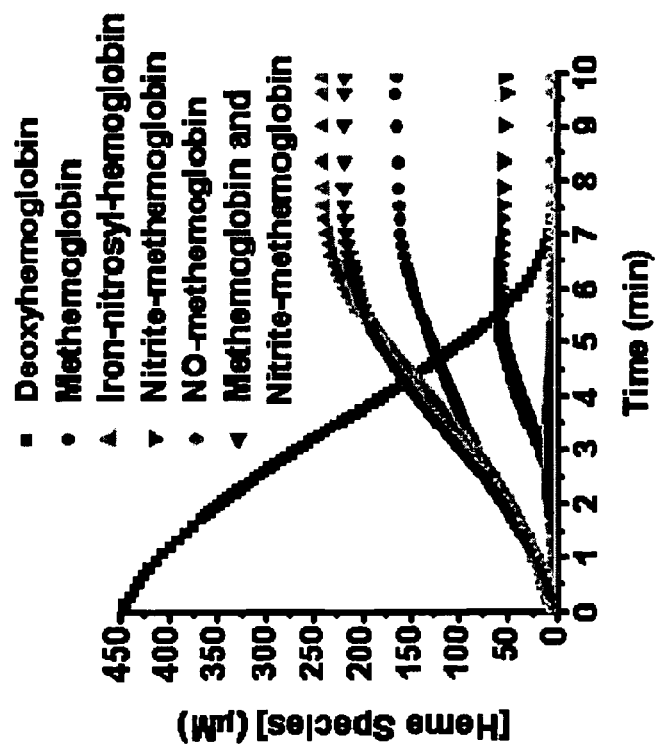

Approximately equal product yields of iron-nitrosyl-hemoglobin and total MetHb were observed at the low (FIGS. 1A and 1B), equimolar, and high nitrite:hemoglobin (FIGS. 1D and 1E) ratios, consistent with Equations 1 and 2 and previous studies. Interestingly, a significant amount of nitrite-MetHb but no NO-MetHb was observed when both species were included in the regression analysis (FIGS. 1B, 1E). To confirm the presence of nitrite-MetHb and the absence of NO-MetHb, chi-square values over time were compared for these reactions, fitted with and without each species in the standard reference spectra (FIGS. 1C, 1F). At all nitrite:hemoglobin ratios, significantly lower residuals were observed when nitrite-MetHb was included. Addition of NO-MetHb did not further lower the chi-square values. Notably, inclusion of NO-MetHb alone often resulted in residuals that were nearly as high as when neither species was included. Additional experiments were performed at room temperature and NO-MetHb was not observed when 1 mM deoxyHb was reacted with 250 μM nitrite for 180 minutes. In all these cases with four fold heme to nitrite (n=3), regression analysis reported no NO-MetHb at any of the time-points when all the basis spectra were used. These data suggest that nitrite-MetHb, and not quasi-stable NO-MetHb, is an intermediate of the deoxyhemoglobin-nitrite reaction. Similar results were observed in the deoxymyoglobin-nitrite reaction (Shiva et al., *Circ Res.* 100(5):654-661, 2007). Importantly, the absence of an NO-MetHb species in these reactions was confirmed using a novel chemiluminescence-based approach.

Analysis of Nitrite Bound Methemoglobin (HbFe$^{III}$—$NO_2$)

Figure 2A:
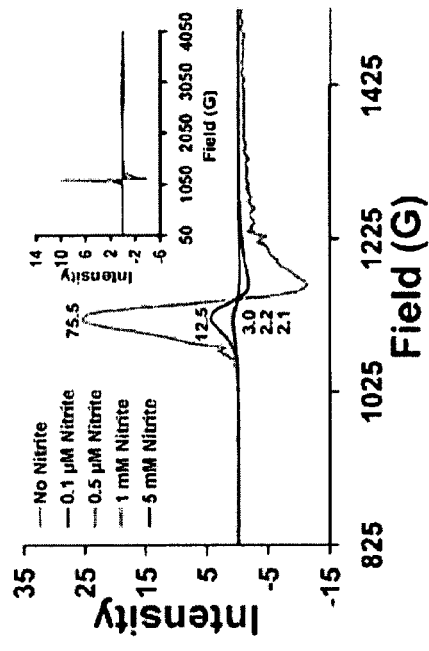
FIG. 2 is a series of graphs showing the EPR silence of MetHb-$NO_2^-$ and its paradoxical dissociation constant. (A) At pH 7.4, nitrite (0, 0.1, 0.5, 1, and 5 mM) was added to 84.8 μM MetHb and the low field EPR measured at 4 K. Samples were frozen for EPR five minutes after nitrite addition. The concentrations of remaining MetHb, measured by double integration of the MetHb signal, were 47.7, 27.4, 14.6, and 2.9 μM respectively (as indicated adjacent to each tracing). No low spin MetHb EPR signals at lower g values were detected (inset). The EPR silence of MetHb-$NO_2^-$ was confirmed in three separate MetHb preparations and in two different laboratories (Hogg and Kim-Shapiro labs). The average dissociation constants of MetHb-$NO_2^-$, calculated from the change in the g=6 MetHb EPR signals secondary to nitrite binding, were 75 μM, 271 μM, 284 μM, and 285 μM for 0.1, 0.5, 1, and 5 mM of added nitrite. (B) An analogous set of experiments performed at pH 6.5 demonstrated a more significant EPR silencing effect. The measured concentration of MetHb remaining after the addition of 0, 0.1, 0.5, 1, and 5 mM nitrite were 75.5 μM, 12.5 μM, 3 μM, 2.2 μM, and 2.1 μM (indicated on figure next to curves). The average dissociation constants of MetHb-$NO_2^-$ obtained by analysis of the change in g=6 MetHb EPR signal secondary to nitrite binding were 7 μM, 18 μM, 28 μM, and 145 μM for the 0.1, 0.5, 1, and 5 mM of added nitrite. (C) The kinetics of nitrite (4 mM) association with MetHb (50 μM) at pH 7.4 was measured by stopped-flow absorption spectroscopy. The observed rate of nitrite binding was 0.10 $s^{-1}$ for the reaction shown here and averaged 0.12±0.01 $s^{-1}$ between 6 trials. Inset depicts raw data. (D) The kinetics of nitrite (4 mM) association with MetHb (50 μM) at pH 6 was measured by stopped-flow absorption spectroscopy. The observed rate of nitrite binding was 0.87 $s^{-1}$ for the reaction shown here and averaged 0.76±0.11 $s^{-1}$ between 6 trials. Inset depicts raw data. (E) The kinetics of nitrite dissociation from MetHb was measured by stopped-flow absorption spectroscopy for the reaction of 2.5 mM nitrite-MetHb with 2.5 mM potassium cyanide at pH 7.4. The rate of nitrite dissociation was 0.051 $s^{-1}$ for the reaction shown here and averaged 0.053±0.002 $s^{-1}$ between 3 trials. Inset depicts raw data. (F) The kinetics of nitrite dissociation from MetHb was measured by stopped-flow absorption spectroscopy for the reaction of 2.5 mM nitrite-MetHb with 2.5 mM potassium cyanide at pH 6. The rate of nitrite dissociation was 0.15 $s^{-1}$ for the reaction shown here and averaged 0.153±0.001 $s^{-1}$ between 3 trials. Inset depicts raw data.
Figure 2B:
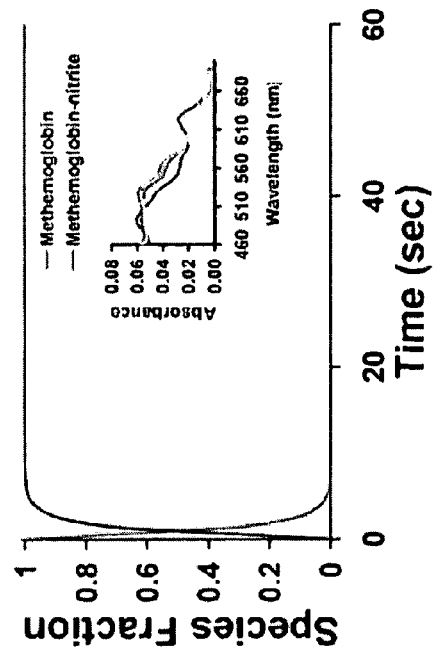
Figure 2C:
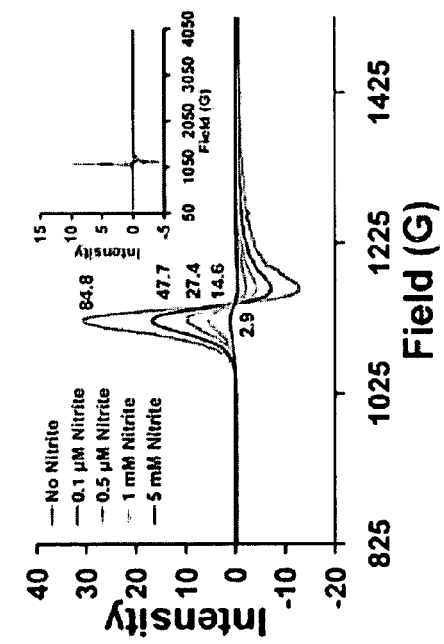
Figure 2D:
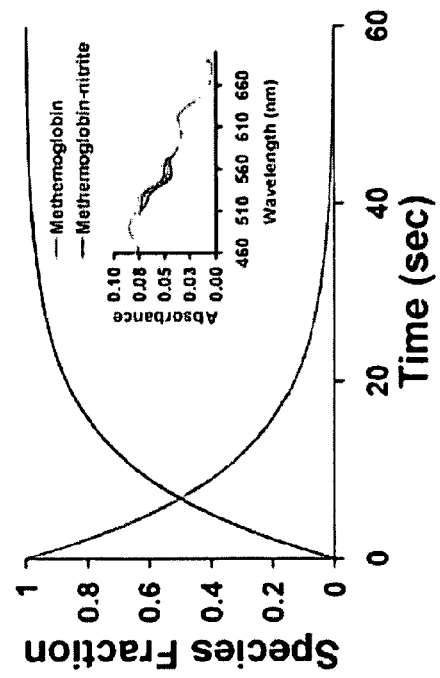
Figure 2E:
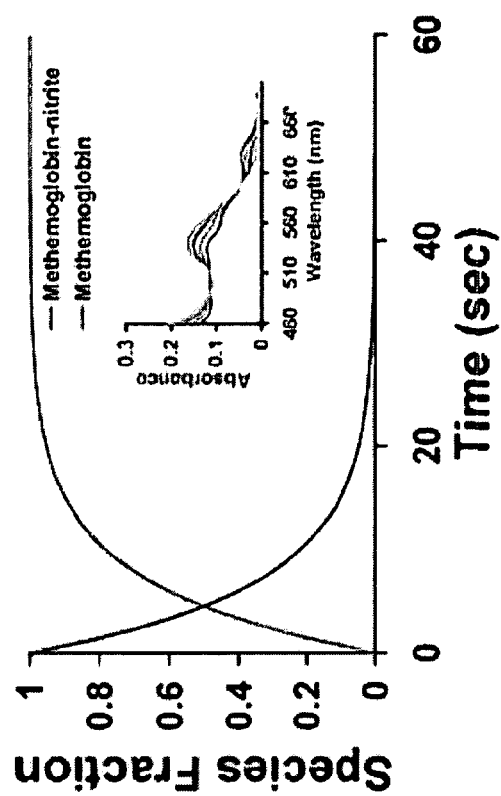
Figure 2F:
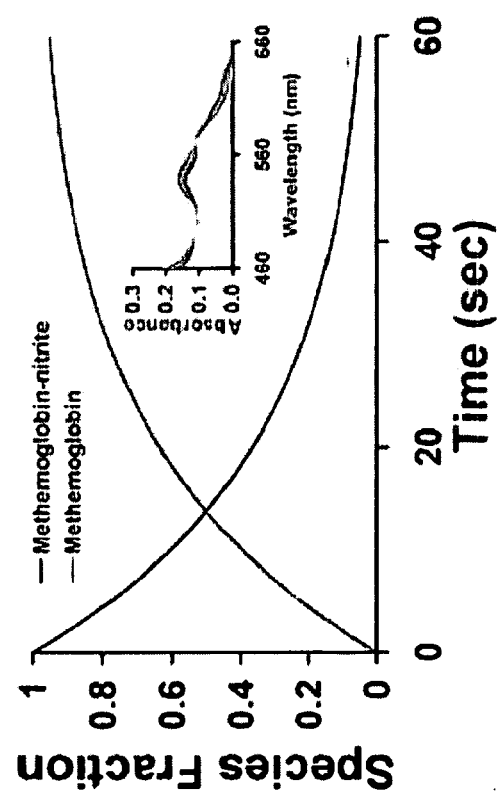

In order to confirm the stoichiometry of reactions described above, freeze-quench EPR measurements of products were performed during the course of the nitrite-deoxyhemoglobin reaction. Surprisingly, MetHb yields by EPR were consistently lower than those measured by UV-Vis absorption spectroscopy. To further probe this observation, increasing concentrations of nitrite were added to MetHb and it was found that, similar to nitrite bound to bacterial nitrite reductase and other ferric heme proteins (Day et al., *Biochemistry-US* 27: 2126-2132, 1988; Young & Siegel, *Biochemistry-US* 27:2790-2800, 1988), MetHb-$NO_2^-$ is effectively EPR silent (FIG. 2A). The large low field peak due to high spin MetHb around g=6 decreased as nitrite was added and no concomitant signal for the low spin MetHb was seen at higher magnetic fields (see FIG. 2A inset). Interestingly, the EPR silent species is more stable at lower pH as evidenced by the faster disappearance of the g=6 signal at equivalent nitrite concentrations at pH 6.5 (FIG. 2B). The tighter binding of nitrite to MetHb at lower pH was also confirmed using stopped-flow absorption measuring the association and dissociation rates of nitrite bound MetHb (FIGS. 2C-2F). Thus, both absorption and EPR spectroscopy show that nitrite binds MetHb tighter at lower pH. This effect is not likely to be solely due to the presence of hydroxyl vs. water as the transition between aquo-MetHb and hydroxyl MetHb has a $pk_a$ of 8. Thus, whether water is bound or not would not be expected to have a large differential effect between pH 7.4 and 6.5. Some contribution may be due to other ionizations such as at the proximal histidine (see discussion). Interestingly, the dissociation constant measured by examination of the g=6 EPR signal (as described in the methods section) is much lower than that calculated using absorption spectroscopy (reported to be around 1-5 mM; Rodkey, *Clin. Chem.* 22:1986-1990, 1976; Wanat et al., *J Biol Inorg Chem* 7:165-176, 2002). Moreover, more extensive EPR silencing was observed with lower nitrite concentrations, resulting in EPR-derived dissociation constants of nitrite-MetHb of 75 μM for 100 μM of added nitrite and 285 μM for 5 mM added nitrite at pH 7.4 and 7 μM for 100 μM added nitrite and 145 μM for 5 mM of added nitrite at pH 6.5. These data suggest that under physiological conditions in the erythrocyte, a substantial fraction of nitrite would be bound to MetHb rather than free in solution.

The EPR silence of MetHb-$NO_2^-$ could occur due to line broadening resulting from g-strain, as considered for other ferric heme proteins (Day et al., *Biochemistry-US* 27: 2126-

Figure 3:
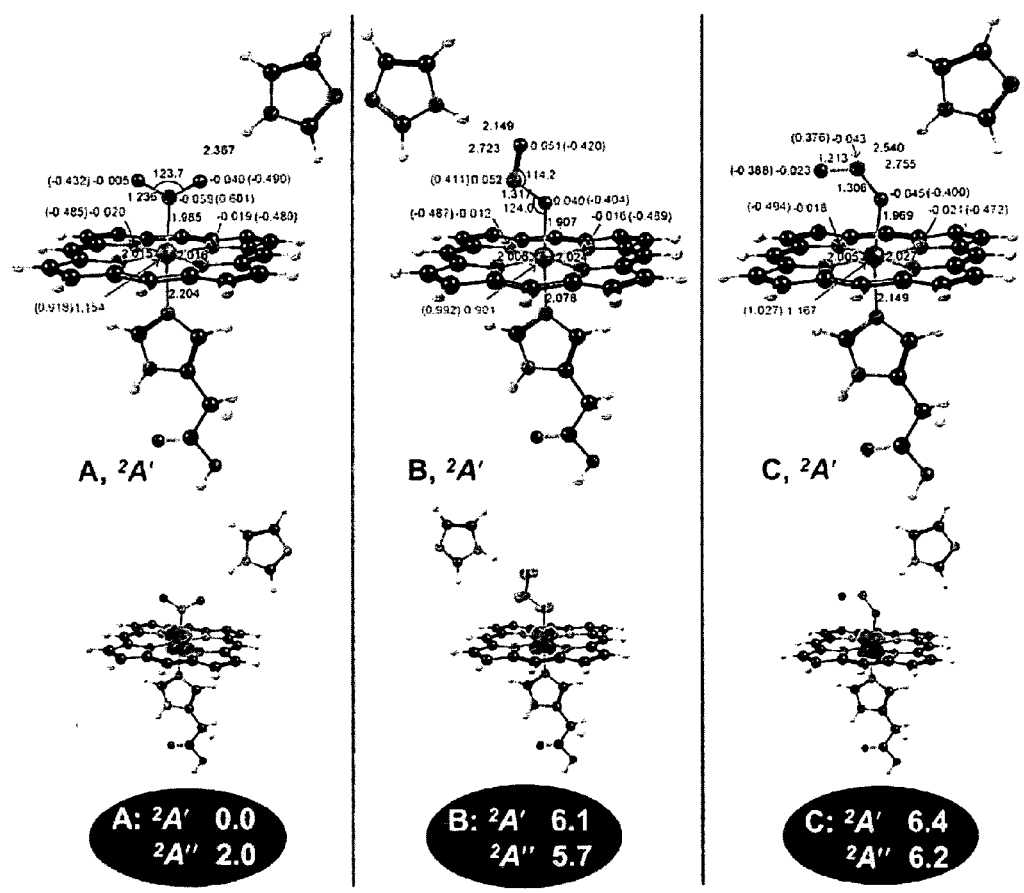
FIG. 3 shows molecular models of selected OLYP/STO-TZP results for an $Fe^{III}$-nitro (A) and two $Fe^{III}$-O-nitrito (B and C) models. Each of these models was restricted to $C_S$ symmetry, which allowed the separate optimization of both the $^2A'$ and $^2A''$ states, which correspond the unpaired electron occupying one or the other of the two $d_\pi$ ($d_{xz}$ or $d_{yz}$) orbitals. The three diagrams in the top rows present selected optimized bond distances (Å, in black), Mulliken spin populations (in magenta) and charges (in green in parentheses) for the $^2A'$ states of the three models. In the middle row are shown the corresponding spin density plots, where the excess spin density is shown in cyan. Shown against the oval insets at the bottom of the figure are the energies of the various states studied (in kcal/mol), relative to the $^2A'$ state of model A. Observe that although the O-nitrito forms B and C are higher in energy than the A form, the $^2A'$ and $^2A''$ states are very similar in energy for all three forms.

2132, 1988; Young & Siegel, *Biochemistry-US* 27:2790-2800, 1988). To explore this possibility and other aspects of the electronic configuration of MetHb-NO$_2^-$, density functional theory (OLYP/TZP) calculations were performed on various six-coordinate nitrite-bound ferric porphyrins. The proximal ligand in the majority of these calculations is imidazole with an acetic acid side-chain that hydrogen bonds to the NH group, while the N-bound ("nitro") or O-bound nitrite hydrogen bonds to another imidazole on the distal side (FIG. 3). For all the models, the nitro form was found to be more stable than the O-nitrito form by about 7 kcal/mol. However, the relative orientation of the nitrite and proximal imidazole planes (coplanar or perpendicular) made little difference (<1 kcal/mol) in the energy of these species, suggesting that states with either conformation would be equally populated. For every conformation of every species examined (whether nitro or O-nitrito), the two alternative d$^1_\pi$ states ($^2$A' and $^2$A" for C$_S$ point group symmetry) proved to be within 0.5 kcal/mol of each other; suggesting that rapid fluctuation between these states may provide an explanation for the lack of an EPR signal for nitrite-MetHb.

Unlike nitrate, nitrite may be a noninnocent ligand. A recent DFT analysis (Conradie & Ghosh, *Inorg Chem* 45:4902-4909, 2006) emphasizes the π-accepting character of N-bound nitrite and the high electron affinities (EAs) of ferric-nitro porphyrins. Here, it was found that both the six-coordinate ferric-nitro and O-nitrito models have similar EAs of about 2.0 eV, which is high for electroneutral ferric porphyrins but not so high as to preclude the existence of these species. As shown in FIG. 3, the O-nitrito ligand is noninnocent in certain conformations (FIG. 3), which may be viewed as a Fe$^{II}$—NO$_2$' character. Interestingly, the existence of a Fe$^{II}$—NO$_2$' nature of nitrite bound to an Fe$^{III}$ porphyrin has been considered previously in other contexts (Oshea, et al., *J Org Chem* 61:6388-6395, 1996; Castro & Oshea, *J Org Chem* 60:1922-1923, 1995). Generally, these results help explain recent reports of an EPR silent intermediate in the nitrite-deoxyhemoglobin reaction that is detectable by reductive chemiluminescence (Nagababu et al., *Nitric Oxide* 15:20-9, 206; Nagababu et al., *J. Biol. Chem.* 278:46349-46356, 2003).

The Reaction of NO with Nitrite-MetHb; Turning Reductive Nitrosylation Upside Down It was therefore hypothesized that a highly electron-hungry nitrite-metHb intermediate may undergo a radical-radical reaction of the coordinated nitrite with NO leading to the formation of N$_2$O$_3$. Synthetic ferric-nitro porphyrins, where the sixth ligand is more labile than the proximal histidine in hemoglobin, also exhibit a similar means of relieving their electron deficiency by reacting with NO, leading to the formation of highly stable {FeNO}$^6$ ferric-nitro-nitrosyl complexes. (Nasri et al., *Inorg Chem* 43:2932-42, 2004; Lim et al., *J Am Chem Soc* 124:9737-43, 2002). NO formed in the nitrite-deoxyhemoglobin reaction could react with the Fe$^{II}$-*i*NO$_2$' intermediate at very rapid reaction rates and potentially compete with the otherwise dominant and inactivating reactions of NO with ferrous heme groups. This general reaction scheme is shown in Equation 3.

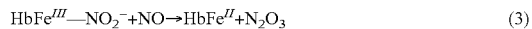

HbFe$^{III}$—NO$_2^-$+NO→HbFe$^{II}$+N$_2$O$_3$ (3)

Reductive nitrosylation is a classical reaction of two molecules of NO with MetHb in which the first NO molecule binds to MetHb (forming {FeNO}$^6$). The nitrosonium ion will react with water or another nucleophile and the second NO binds to the newly formed ferrous heme. While this reaction is very slow (on the order of 0.001 s$^{-1}$ when performed with high NO concentrations (1-2 mM NO); Fernandez & Ford, *J Am Chem Soc* 125:10510-10511, 2003), it has been reported to occur at much faster apparent rates (Nagababu et al., *Nitric Oxide* 15:20-29, 2006). Fernandez and Ford showed that nitrite, which is a ubiquitous and abundant contaminant of NO solutions, could catalyze the reductive nitrosylation reaction, increasing the observed rate by approximately 4-fold in the presence of 20 mM nitrite and 1-2 mM NO (Fernandez & Ford, *J Am Chem Soc* 125:10510-10511, 2003). They suggested that nitrite accelerated the reaction through a mechanism in which nitrite reacts with the ferrous-nitrosonium intermediate to yield deoxyhemoglobin and N$_2$O$_3$.

Fe$^{II}$—NO$^+$+NO$_2^-$→Fe$^{II}$+N$_2$O$_3$ (4)

However, while this mechanism could accelerate MetHb reduction by NO and lead to N$_2$O$_3$ formation, it is still too slow to compete with NO heme reactions and is difficult to reconcile with more rapid rates of reductive nitrosylation observed by others in the field (Nagababu et al., *Nitric Oxide* 15:20-9, 2006; Han et al., *Proc. Natl. Acad. Sci. USA* 99:7763-7768, 2002).

An alternative solution based on the EPR findings disclosed herein was therefore considered. Previous experiments, including those by Fernandez and Ford, were conducted at high NO concentrations, such that NO may have preferentially bound to the MetHb and thereby prevented or greatly diminished nitrite binding to MetHb (NO binds MetHb with approximately 25 times the affinity of nitrite; Rodkey, *Clin. Chem.* 22:1986-90, 1976; Cooper, *Biochim. Biophys. Acta-Bioenerg.* 1411:290-309, 1999). Such competitive binding of NO would inhibit generation of the nitrite-MetHb complex, which may be involved in catalytic reductive nitrosylation.

Figure 4A:
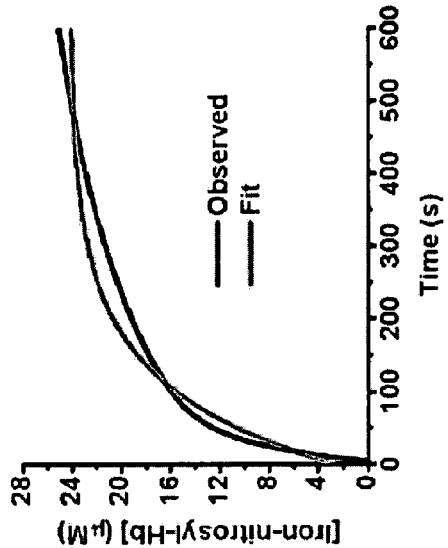
FIG. 4 is a series of graphs showing the reductive nitrosylation of nitrite-MetHb catalyzed by NO. Formation of iron-nitrosyl-hemoglobin by reductive nitrosylation of nitrite- MetHb (rapid) and NO-MetHb (slow) was monitored by absorption spectroscopy and spectral deconvolution. (A) 1 mM NO was added to a pre-equilibrated solution of 30 µM deoxygenated MetHb and 5 mM nitrite. (B) The observed change in iron-nitrosyl-hemoglobin concentration for the reaction shown in (A) was compared to the theoretical iron-nitrosyl-hemoglobin concentration as predicted by fitting the concentration of $HbFe^{II}$—NO to a single exponential that yielded an observed rate of 0.0086 $s^{-1}$. (C) 50 µM NO was added to a pre-equilibrated solution of 30 µM deoxygenated MetHb and 5 mM nitrite. (D) The observed change in iron-nitrosyl-hemoglobin concentration for the reaction shown in (c) was compared to the theoretical iron-nitrosyl-hemoglobin concentration as predicted by fitting the concentration of $HbFe^{II}$—NO to a single exponential, which yielded an observed rate of 0.018 $s^{-1}$. (E) The observed rates of iron-nitrosyl-hemoglobin formation as a function of variable nitrite concentrations. These reactions were carried out with 30 µM deoxygenated MetHb, 1 mM NO, and a range of nitrite concentrations at pH 7.4. The line shown is a fit to the data. The inset shows the same data re-plotted on a different scale so that nitrite catalysis is more apparent. The slope ($k_{nitrite}$) is 0.13 $M^{-1}s^{-1}$, similar to that reported previously. (Fernandez & Ford, *J Am Chem Soc* 125:10510-10511, 2003). The rate of reductive nitrosylation that was observed when no nitrite is added is higher than that reported previously (Fernandez & Ford, *J Am Chem Soc* 125:10510-10511, 2003) due, perhaps, to the fact that the experiments were performed at a higher temperature (25° C. vs. 37° C.) and less NO (1.8 mM vs. 1 mM (from 500 µM ProliNO)) was used. (F) The observed rates of iron-nitrosyl-hemoglobin formation as a function of variable NO concentrations. These reactions were carried out with 30 µM deoxygenated MetHb, 5 mM nitrite, and a range of NO concentrations at pH 7.4. The line shown is a fit to the data.
Figure 4C:
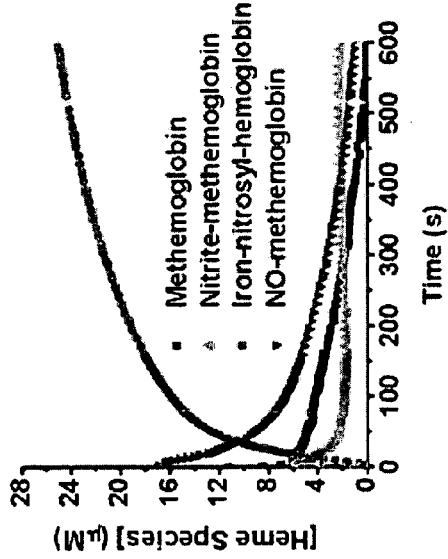
Figure 4B:
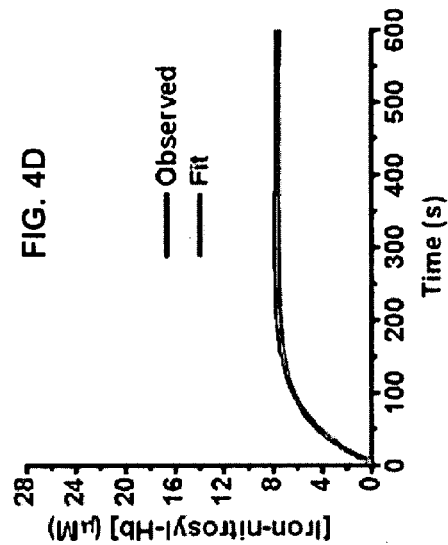
Figure 4D:
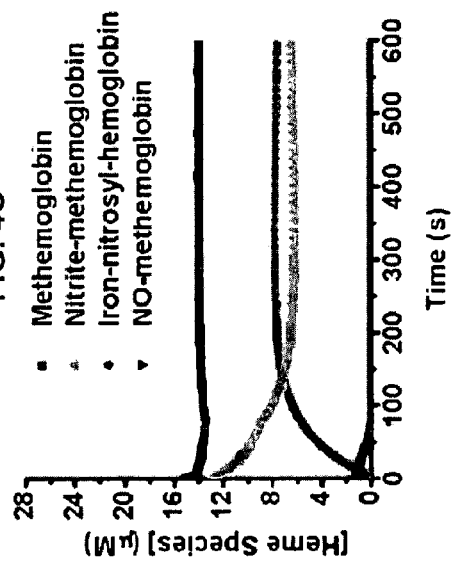
Figure 4F:
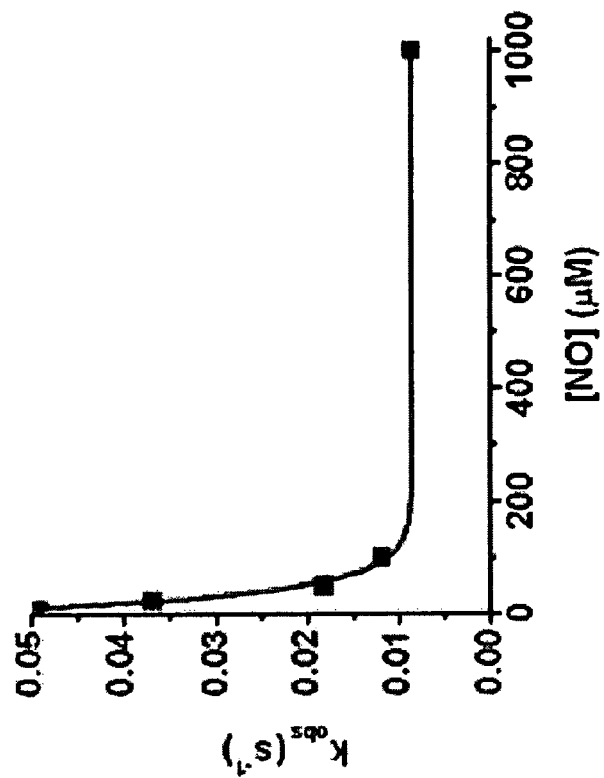
Figure 4E:
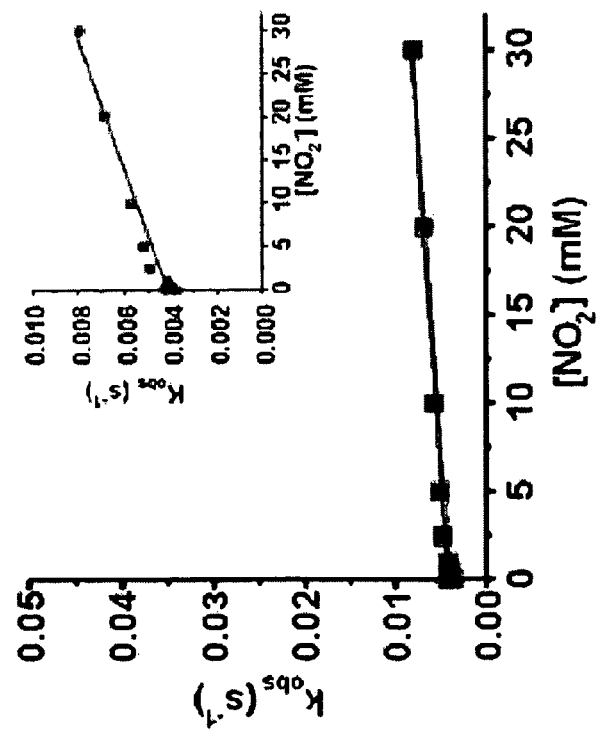

To test this hypothesis, the effect of varying the nitrite concentration in the presence of excess NO was examined (1 mM) and similar rates of MetHb reduction and iron-nitrosyl-hemoglobin formation with increasing nitrite concentration were observed as reported earlier by Fernandez and Ford (Fernandez & Ford, *J Am Chem Soc* 125:10510-10511, 2003). FIG. 4A traces the change in all heme species over time as measured by absorption spectroscopy, while FIG. 4B shows the fit for HbFe$^{II}$—NO formation to a single exponential process. A summary of observed rates measured with 1 mM NO and various nitrite concentrations is shown in FIG. 4E. The deviation of the fit from measured HbFe$^{II}$—NO in FIG. 4E suggests that the process is more complicated than a single exponential process, possibly due to a faster concurrent process in which NO reacts with HbFe$^{II}$—NO$_2^-$. This hypothesis is confirmed by the observation that the observed reaction rate for HbFe$^{II}$—NO formation is actually significantly faster at lower NO concentrations (FIGS. 4C, 4D and 4F). The observed rate of formation of HbFe$^{II}$—NO from the reaction of 30 μM MetHb with 1 mM NO and 5 mM nitrite is 0.0086 s$^{-1}$. For the mechanism of nitrite-mediated catalysis of reductive nitrosylation suggested by Fernandez and Ford, the rate should decrease as the NO concentration is decreased. In contrast, the observed rate of the reaction actually increased when 30 μM MetHb was mixed with 50 μM NO and 5 mM nitrite (0.018 s$^{-1}$). The calculated observed reaction rates as a function of variable NO with 5 mM nitrite and 30 μM MetHb are summarized in FIG. 4F. Notably, the observed reaction rate increased significantly with decreasing NO concentrations, consistent with inhibition of nitrite-MetHb formation at high NO concentrations secondary to competitive binding of excess NO. Examination of reaction intermediates by spectral deconvolution (FIGS. 4A and 4C) also indicates that after NO addition, MetHb-NO$_2^-$ is consumed faster than MetHb, consistent with a predominant and faster reaction between nitrite-MetHb and NO.

Figure 5A:
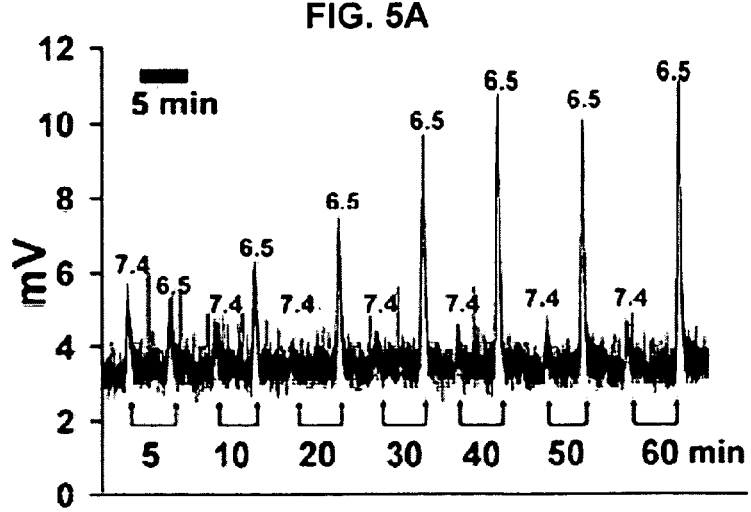
FIG. 5 is a series of graphs showing nitrite mediated nitrosothiol formation. (A) Time course of GSNO formation in the reaction of 1 mM nitrite and 1 mM GSH in PBS, pH 6.5 or in PBS, pH 7.4 at room temperature. Injections were made into a purge vessel in-line with the nitric oxide analyzer at regular intervals to detect GSNO by the 2C-assay. The figure represents raw chemiluminescence data of individual injections made at indicated time intervals for one of 5 repeats of the time course studies. Notably, no signals were detected when samples were pretreated with 5 mM $HgCl_2$ for 3 minutes. NEM was found to have no effect on the size of the signal when tested on a sample incubated for 30 minutes. (B) Formation of SNO-Hb in the reaction of 300 µM deoxygenated Hb with 1 mM nitrite and 1 mM GSH, at pH 6.5 for 30 minutes at room temperature followed by treatment with SNO-stabilizing solution for 1 hour (modified 2C assay). The figure represents one of three repeats of the experiment and shows the raw data of individual injections either directly (−Hg) or treated with 5 mM $HgCl_2$ for 3 minutes (+Hg). (C) Formation of SNO-Hb in the reaction of 5 mM deoxygenated hemoglobin with 1 mM nitrite and 1 mM GSH, at pH 6.5 for 30 minutes at room temperature followed by treatment with SNO-stabilizing solution for 1 hour (modified 2C assay). The figure represents raw data of individual injections either directly (−Hg) or treated with 5 mM $HgCl_2$ for 3 minutes (+Hg).
FIGS. 5B and 5C show the presence of mercury stable peaks that could be due to N-nitroso, O-nitroso, or C-nitroso. (Feelisch et al., *Faseb J.* 16:1775-1785, 2002). (D) 1 mM GSH was reacted with 1 mM nitrite in either oxygenated or deoxygenated PBS and at either pH 6.5 or pH 7.4 at room temperature. These results are an average±standard error of GSNO concentration measured by the 2C assay (n=5). (E) Hemoglobin (300 µM) in PBS with 100 µM DTPA at pH 6.5 or pH 7.4 was reacted with 1 mM nitrite and 1 mM GSH for 30 minutes at room temperature under different oxygen saturations: 100% oxygenated Hb (oxyHb), 51±4% deoxygenated Hb (partially deoxyHb) or 97±2% deoxygenated Hb (deoxyHb). The samples were treated with SNO-stabilizing solution (2-fold dilution) for 1 hour (modified 2C assay). The results represent the average SNO-Hb measured from three trials±one standard deviation. Prior to addition of SNO-stabilization solution, low molecular weight species were separated from Hb by Centricon filters. Addition of NEM to the filtrate did not affect the measured concentrations of GSNO (n=3). The concentration of GSNO measured was 0.51±0.04 µM, 0.046±0.08 µM and 0.11±0.1 µM for oxyHb, partially deoxyHb and deoxyHb respectively at pH 6.5, and 0.21±0.13 µM, 0 µM and 0.05±0.08 µM for oxyHb, partially deoxyHb and deoxyHb respectively at pH 7.4. When the above reaction was repeated without DTPA, the average SNO-Hb measured for deoxyHb was 4.35±0.44 µM at pH 6.5 and 0.91±0.23 µM at pH 7.4. It was generally found that detected nitrosation was 1-3 times smaller when DTPA was not included in the incubations. When the reaction was repeated without GSH at pH 6.5, the average SNO-Hb measured was 4.32±0.51 µM for 98±2% deoxyHb. (F) Hemoglobin (5 mM) was reacted with 1 mM nitrite and 1 mM GSH in PBS with 100 µM DTPA, at either pH 6.5 or pH 7.4, 30 minutes. These reactions were carried out at two oxygen tensions: 100% oxygenated Hb (oxyHb) and 98±1% deoxygenated Hb (deoxyHb), followed by 6-fold dilution in SNO-stabilization solution for 1 hour (modified 2C assay, n=3). The average concentration of SNO-Hb was 0 µM (oxyHb) and 24.44±3.52 µM (deoxyHb) at pH 6.5 and 0 µM (oxyHb) and 8.94±2.49 µM (deoxyHb) at pH 7.4. There was no GSNO formed based on measurements on the filtrate obtained using Centricon filters.

Evidence for $N_2O_3$ Formation in the Reaction of Nitrite and deoxyHb: Oxygen and pH Dependence of S-Nitrosation In order to examine if the nitrite/deoxyhemoglobin reaction generates a nitrosating agent, a modified Cu/cysteine (2C) reductive-chemiluminescent assay (see Materials and Methods) was used to examine SNO formation in a large variety of conditions with and without inclusion of glutathione (GSH), in order to determine if S-nitrosoglutathione (GSNO) is formed. FIG. 5 shows representative and summation data for the different conditions studied. To assess Hb-dependent RSNO formation it was important to first assess basal levels of RSNO formation that occur when nitrite is incubated with GSH. The degree of nitrosation in the absence of Hb was examined. In FIG. 5A, 1 mM GSH and 1 mM nitrite were mixed under anaerobic conditions at pH 7.4 or pH 6.5 and GSNO was measured by the 2C assay at the indicated time points. Within twenty minutes of mixing, the GSNO signal was much larger at pH 6.5 than at pH 7.4. FIG. 5D summarizes GSNO formation as measured by the nitric oxide analyzer (NOA) at the indicated time points under oxygenated and deoxygenated reaction conditions in the presence of 1 mM GSH and 1 mM nitrite. The samples were injected directly into a nitric oxide analyzer at the times indicated. The most GSNO was formed at pH 6.5 under deoxygenated conditions. Under these conditions about 200 nM GSNO is formed within five minutes of mixing and almost 1 µM GSNO accumulated after one hour. The pH dependence of nitrosation that was observed suggests the involvement of nitrous acid. The $pK_a$ of nitrous acid is about 3.15 so that (in the absence of any other reactions) adding 1 mM nitrite would yield about 60 nM nitrous acid at pH 7.4 and 500 nM nitrous acid at pH 6.5 (Williams (Elsevier, Amsterdam, 2004) *Nitrosation Reactions and the Chemistry of Nitric Oxide*). Nitrosation can occur through direct reaction of nitrous acid and a thiol but the nature of the acid catalysis of this reaction and its kinetics make it unlikely that this would occur in the experiments described above (Morris & Williams, *J Chem Society-Perkin Transactions* 2 513-516, 1988). Another possibility is that nitrosation occurred via the intermediacy of $N_2O_3$ which is in equilibrium with nitrous acid (Williams (Elsevier, Amsterdam, 2004) *Nitrosation Reactions and the Chemistry of Nitric Oxide*). Since the concentration of $N_2O_3$ depends on the concentration of nitrous acid squared, one expects nitrosation to be about 100 times more efficient at pH 6.5 than at pH 7.4. The stability of nitrous acid has been reported to decrease as the oxygen tension increases (Williams (Elsevier, Amsterdam, 2004) *Nitrosation Reactions and the Chemistry of Nitric Oxide*; Beake & Moodie, *J Chem Society-Perkin Transactions* 2 1045-1048, 1995), suggesting a possible explanation for the enhanced nitrosation observed under anaerobic conditions.

Figure 5B:
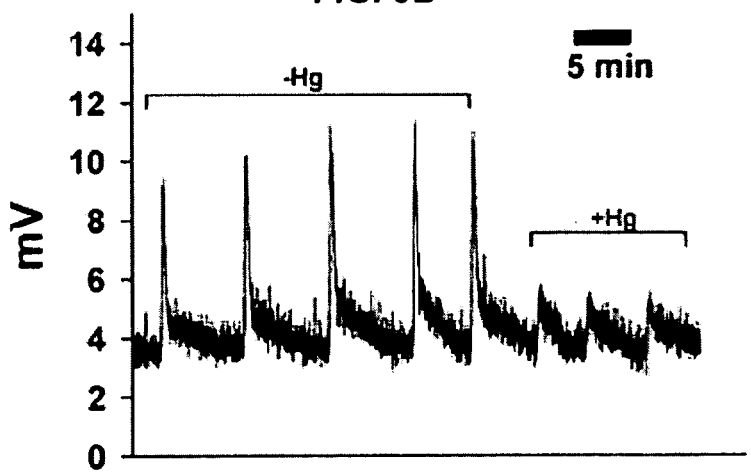
Figure 5C:
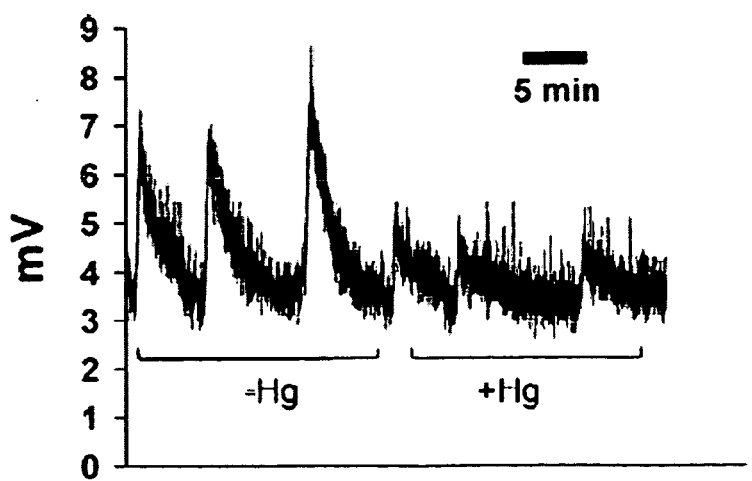

Having established the degree of nitrosation of GSH by nitrite under basal conditions, the effects of Hb were examined. FIGS. 5B and 5C show the result of nitrosothiol measurement by the modified 2C assay following a thirty minute incubation of 1 mM nitrite, 1 mM GSH, and either 300 µM (5b) or 5 mM (5c) deoxygenated Hb. The difference in the signal observed in the presence and absence of Hg is proportional to the amount of S-nitrosothiol produced. FIG. 5E summarizes the results of experiments performed similarly to those shown in FIG. 5D (where Hb is absent), but when 300 µM Hb is added to the mixture of 1 mM GSH and 1 mM nitrite and incubated for thirty minutes. The goal was to measure both low and high molecular weight nitrosothiols when both Hb and GSH were included. The low molecular weight fraction in a portion of the sample was separated from hemoglobin using Centricon filters to allow quantification of GSNO, and SNO-Hb was measured by the modified 2C assay in the remaining portion. It should be noted that GSNO reacts with deoxyHb to make NO (and hence $HbFe^{II}$—NO) and can also react with OxyHb through trans-nitrosation so that in oxygenated and partially oxygenated conditions, SNO-Hb may be a better assessment of accumulated $N_2O_3$ formation (Patel et al., *J. Biol. Chem.* 274:15487-15492, 1999; Spencer et al., *J. Biol. Chem.* 275:36562-36567, 2000). As with the mixtures without Hb present, most nitrosation was observed under deoxygenated conditions at pH 6.5, with SNO-Hb making up almost all of the nitrosated product. Comparison with FIG. 5D reveals that the presence of deoxygenated Hb significantly increases the yield of S-nitrosothiol from nitrite. Under oxygenated conditions all the nitrosation occurs on GSH, with more being formed at pH 6.5 (0.51±0.04 µM) than at pH 7.4 (0.21±0.13 µM) and that amount being more than when the Hb is absent (compare to FIG. 5D, where less than 0.3 µM GSNO was observed after 30 minutes at pH 6.5). These data suggest that nitrite reactions with hemoglobin involve S-nitrosation chemistry, with increasing S-nitrosation occurring under deoxygenated conditions and at lower pH. Notably, inclusion of Hb increases the total amount of nitrosated products from nitrite compared to when Hb is absent.

Figure 11:
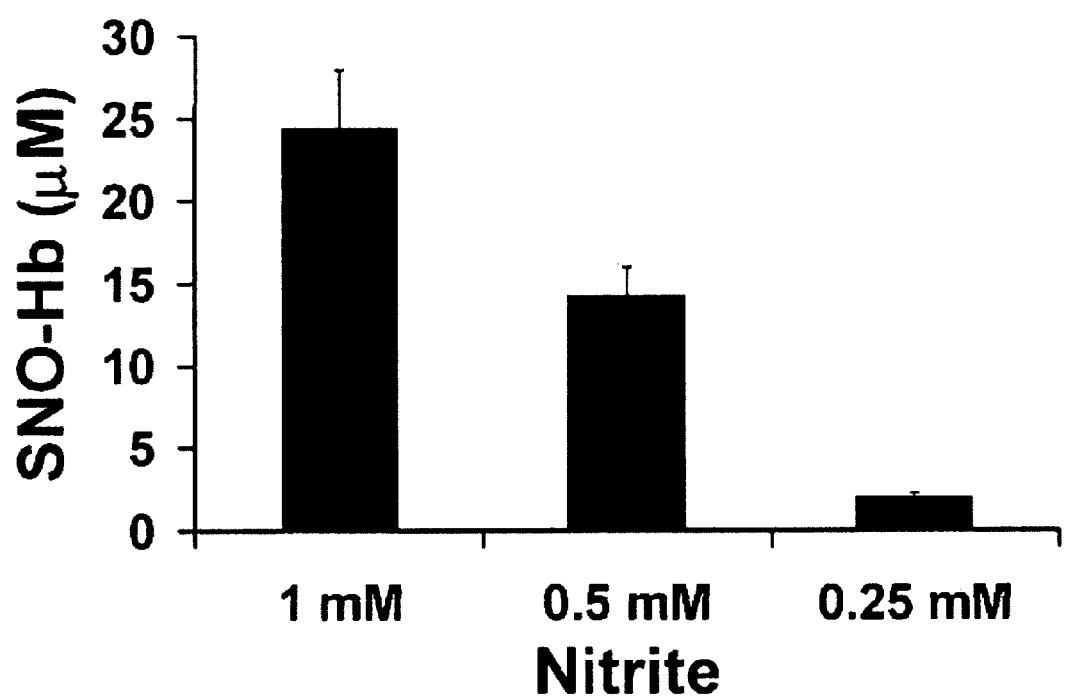
FIG. 11 is a graph showing that SNO-Hb is formed when 5 mM Hb is reacted with varying amounts of nitrite for 30 minutes at room temperature.

A summary of results obtained when 5 mM Hb is used are shown in FIG. 5F. The trends already illustrated in FIGS. 5C and 5D where the most SNO is made under deoxygenated conditions at pH 6.5 are observed under these conditions as well. The higher SNO yield at lower pH could be due to the increased stability of $N_2O_3$ at the lower pH (Williams (Elsevier, Amsterdam, 2004) *Nitrosation Reactions and the Chemistry of Nitric Oxide*) and/or the increased nitrite binding by MetHb at the lower pH (as shown in FIG. 2B). Remarkably, 23 µM SNO-Hb is produced when 5 mM deoxygenated Hb is mixed with 1 mM nitrite and 1 mM GSH for thirty minutes. When the nitrite concentration is reduced to the levels obtained in studies of nitrite infusions in humans (approximately 250 µM; Cosby et al., *Nat. Med.* 9:1498-505, 2003; Lauer et al., *Proc. Natl. Acad. Sci. USA* 98:12814-12819, 2001), 2.5 µM SNO-Hb is formed, similar to levels measured in vivo (Cosby et al., *Nat. Med.* 9:1498-505, 2003; FIG. 11).

$N_2O_3$ Formation by the Reaction of NO with Nitrite-MetHb

Figure 6A:
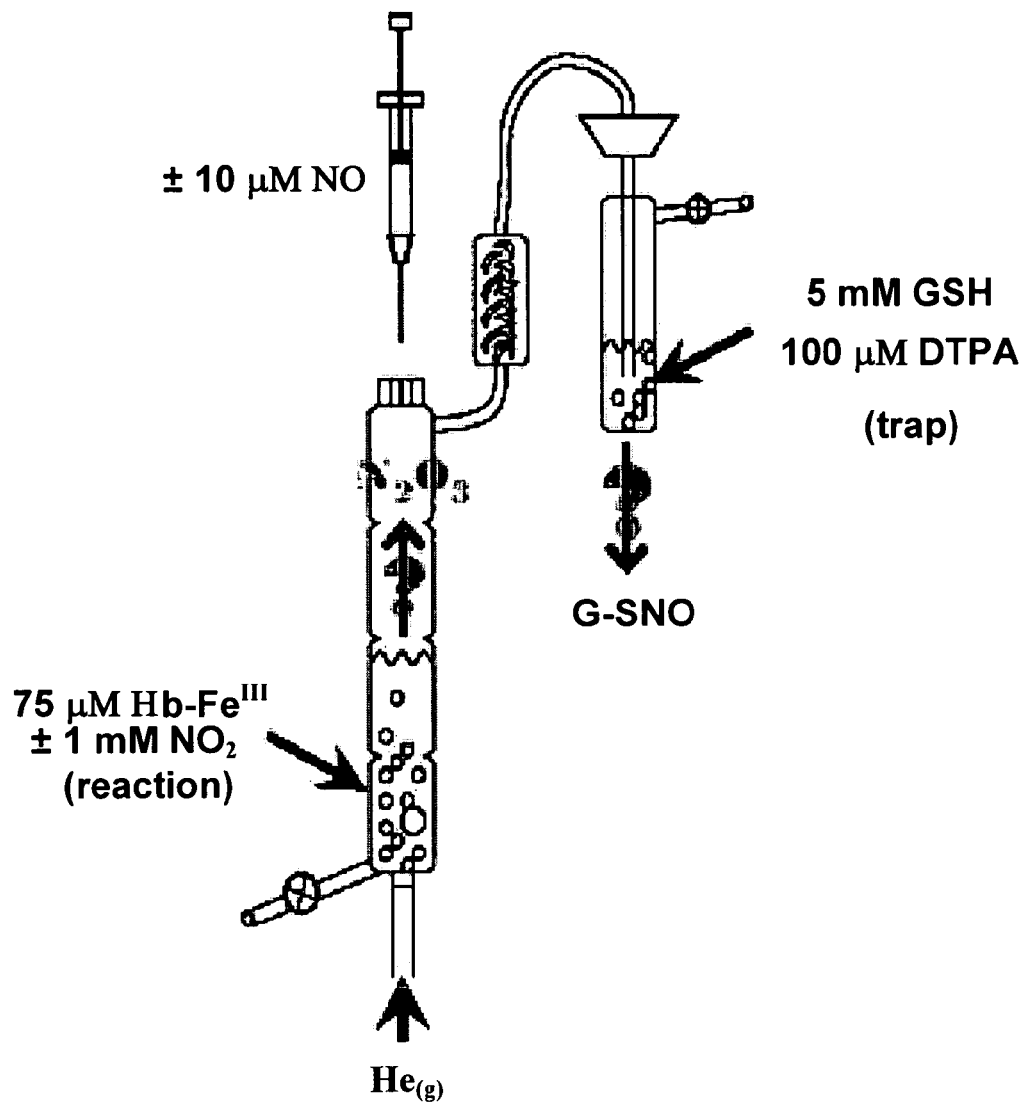
FIG. 6 is a series of graphs showing that NO-catalyzed reduction of nitrite-MetHb generates gas-phase $N_2O_3$. (A) Experimental set-up used to detect the formation and release of $N_2O_3$ into the gas phase. MetHb was pre-equilibrated with nitrite prior to the addition of NO. Any $N_2O_3$ released into the gas phase would subsequently flow into the upstream trap vessel, where it could nitrosylate GSH in the trap and form GSNO. Control reactions that excluded NO, nitrite, or both, were carried out in parallel. The first ("reaction") vessel was purged with helium and maintained under positive pressure to avoid oxygen leak into the system. (B) Detection of GSNO by reductive chemiluminescence. Prior to injection into tri-iodide (see Materials and Methods) aliquots of the trap vessel solution were pre-treated with either acidified sulfanilamide alone (±) or with mercuric chloride followed by acidified sulfanilamide (‡). The difference between the sulfanilamide and mercuric chloride/sulfanilamide peaks measures GSNO in those samples, while the absolute value of the mercuric chloride peak measures the amount of other nitrogen oxide species (such as $HbFe^{II}$—NO). (C) Comparison of average concentrations of GSNO formed in the trap vessel of the reactions of 375 nmoles MetHb and 50 nmoles NO with and without 5 µmoles nitrite. 3.82±2.92 nmoles GSNO was detected in the presence of nitrite, compared to 0.2±0.08 nmoles GSNO when nitrite was excluded from the reaction. (D) Comparison of average HbS—NO concentrations formed in the purge vessel of reactions in (D). 1.16±0.31 nmoles HbS—NO was detected in the presence of nitrite, compared to 1.44±0.16 nmoles HbS—NO when nitrite was excluded from the reaction. (E) Comparison of average Hb-NO concentrations formed in the purge vessel of reactions in (d). 4.65±1.12 nmoles Hb-NO was detected in the presence of nitrite, compared to 3.02±0.74 nmoles Hb-NO when nitrite was excluded from the reaction. Asterisk (*) denotes p value less than 0.05 for the paired analysis of mean daily experiments (n=9 sets of experiments) by the Wilcoxon matched pairs test.
Figure 6B:
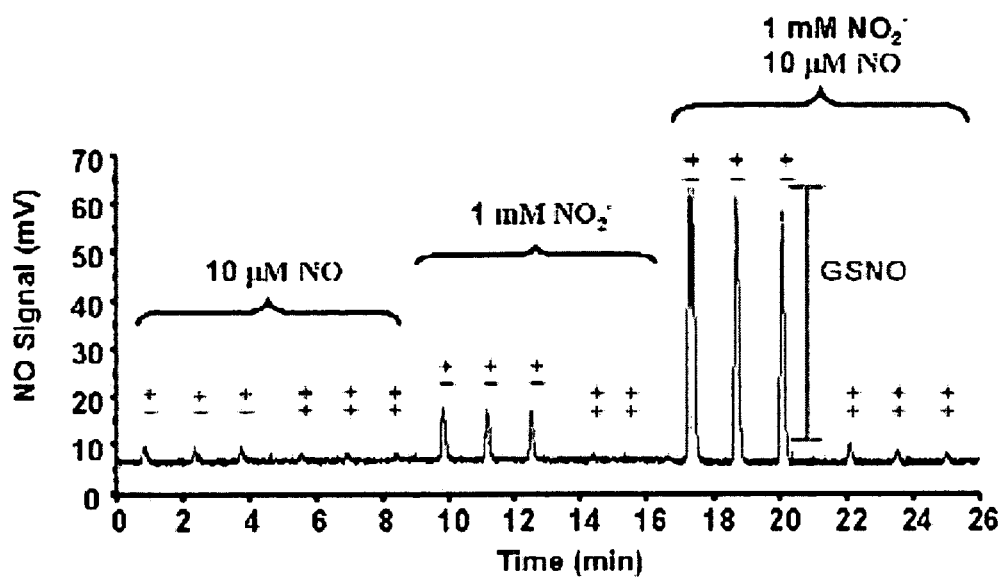
Figure 6C:
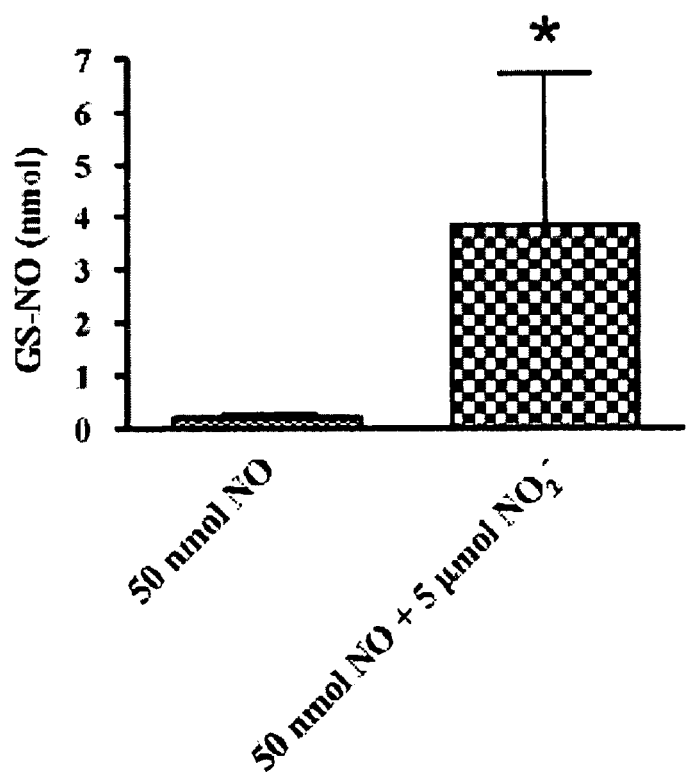

As shown herein (FIG. 4), NO reacts rapidly with the Met-Hb-nitrite complex. In order to see if this reaction generates a freely diffusible nitrosating agent, consistent with the formation of $N_2O_3$ predicted from Equation 3, the experimental system shown in FIG. 6A was assembled. Nitrite and hemoglobin are placed in a purge vessel and continuously bubbled with helium gas. The helium gas is then bubbled through a second chamber (trap) containing GSH and DTPA, and the accumulation of S-nitrosothiols in this second chamber is measured by reductive chemiluminescence. FIG. 6B shows raw chemiluminescence data indicating that addition of NO to a solution of MetHb/nitrite causes the accumulation of synergistically higher levels of GSNO when compared to either NO or nitrite alone. As shown in FIG. 6C, when 375 nmoles MetHb (75 µM in solution) is reacted with 50 nmoles NO (10 µM in solution) after brief pre-equilibration with 5 µmoles nitrite (1 mM in solution), 3.82±2.92 nmoles of GSNO is detected in the trap solution. Importantly, GSNO formation was significantly lower when nitrite was excluded from the reaction, such that only 0.2±0.08 nmoles of GSNO formed in the absence of nitrite (p<0.02). There was minimal GSNO formation in the absence of NO as well.

Figure 6D:
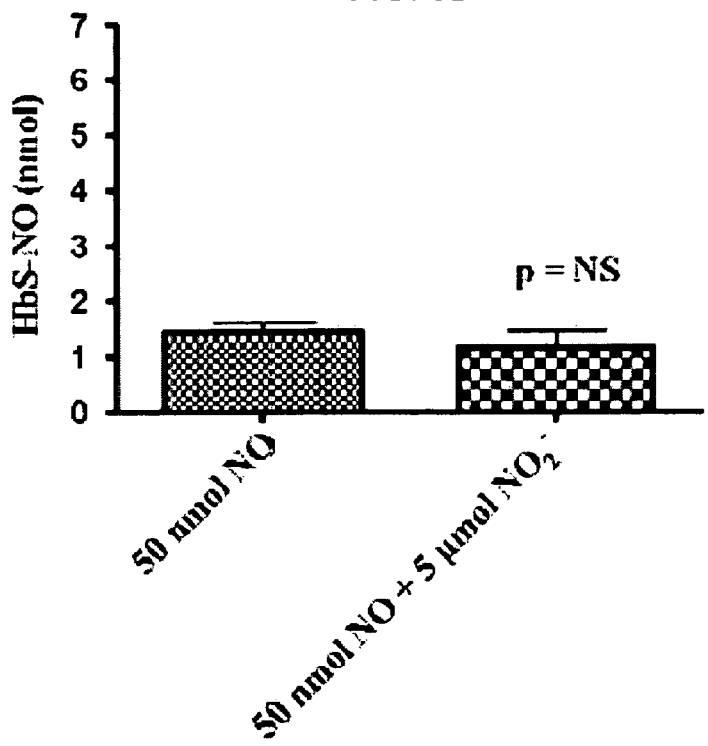
Figure 6E:
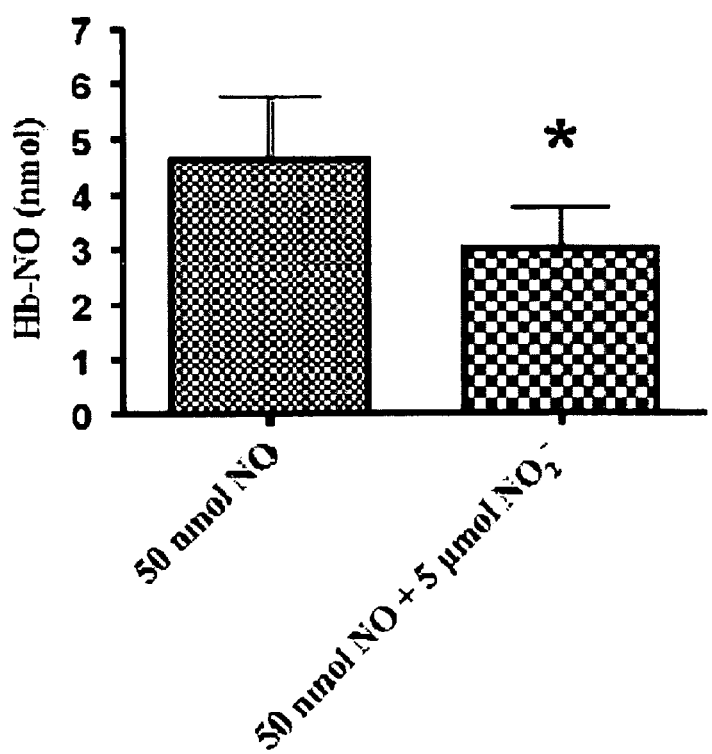

The extent of hemoglobin iron-nitrosylation and S-nitrosation (FIG. 6D) within the reaction solution itself was also investigated. There was no significant difference in SNO-Hb formation whether MetHb was reacted with NO alone (1.44±0.16 nmoles) or with both nitrite and NO (1.16±0.3 nmoles). Interestingly, as demonstrated in FIG. 6E, the amount of HbFe$^{II}$—NO in the reaction solution was significantly lower when MetHb was reacted with both nitrite and NO (3±0.74 nmoles) than when MetHb was reacted with NO alone (4.65±1.12 nmoles). This suggests that while the NO, in the absence of nitrite, can reduce MetHb via the uncatalyzed nitrite-independent reductive nitrosylation pathway, this mechanism generates less gas-phase $N_2O_3$ (limited GSNO in the trap vessel, see FIG. 6C) and HbFe$^{II}$—NO remains in the reaction solution. In contrast, NO-mediated reduction of nitrite-MetHb is simultaneously producing $N_2O_3$ which is then purged out of solution, such that the concentration of HbFe$^{II}$—NO in the reaction vessel is significantly lower (FIG. 6D) and the concentration of GSNO in the trap vessel is significantly higher (FIG. 6C). These results suggest that NO reactions with nitrite-MetHb can effectively compete with ferric heme autocapture and thus increase the efficiency of $NO_x$ escape.

$N_2O_3$ Formation and S-Nitrosation in the deoxyHb/Nitrite Reaction Requires Reactions with MetHb-$NO_2^-$ Nagababu et al. (*Nitric Oxide* 15:20-29, 2006) have recently reported the formation of SNO-Hb in the reaction of deoxyHb and nitrite. Using an ascorbate/Cu(II) chemiluminescence-based assay, they detected approximately 22 µM SNO-Hb formed after a sixty minute incubation of 250 µM nitrite with 1 mM deoxyHb at neutral pH. This is much more than is observed here, even when 1 mM nitrite is used (FIG. 5). One important difference between the methods used by Nagababu et al. and those used here is that when the heme reactions were stopped here with ferricyanide, the samples were also treated with N-ethylmaleimide (NEM) to block all free thiols. In contrast, Nagababu and colleagues did not treat with NEM to block thiol. Indeed, when their ascorbate/Cu(II) method was used and the samples were not treated with NEM along with the added ferricyanide, significantly more SNO-Hb was measured than when the NEM was added. Likewise, when NEM was left out of the SNO-Hb stabilization solution in the modified 2C assay, much more SNO was detected (4.1±2.6 µM vs. 1.7±2.4 µM SNO for one hour incubation of 250 µM deoxyHb with 1 mM nitrite). These results are consistent with recent observations by Feelisch and colleagues, who have also described artifactually high SNO-Hb formation after treatment with ferricyanide (Bryan et al., *Nitric Oxide-Biol Ch* 10:221-8, 2004). It is therefore likely that ferricyanide oxidizes deoxyhemoglobin to methemoglobin and thus increases the concentration of MetHb-$NO_2^-$ that is necessary for $N_2O_3$ formation via the reaction of the Nitrite-MetHb intermediate with NO generated in the nitrite-deoxyhemoglobin reaction.

Figure 12:
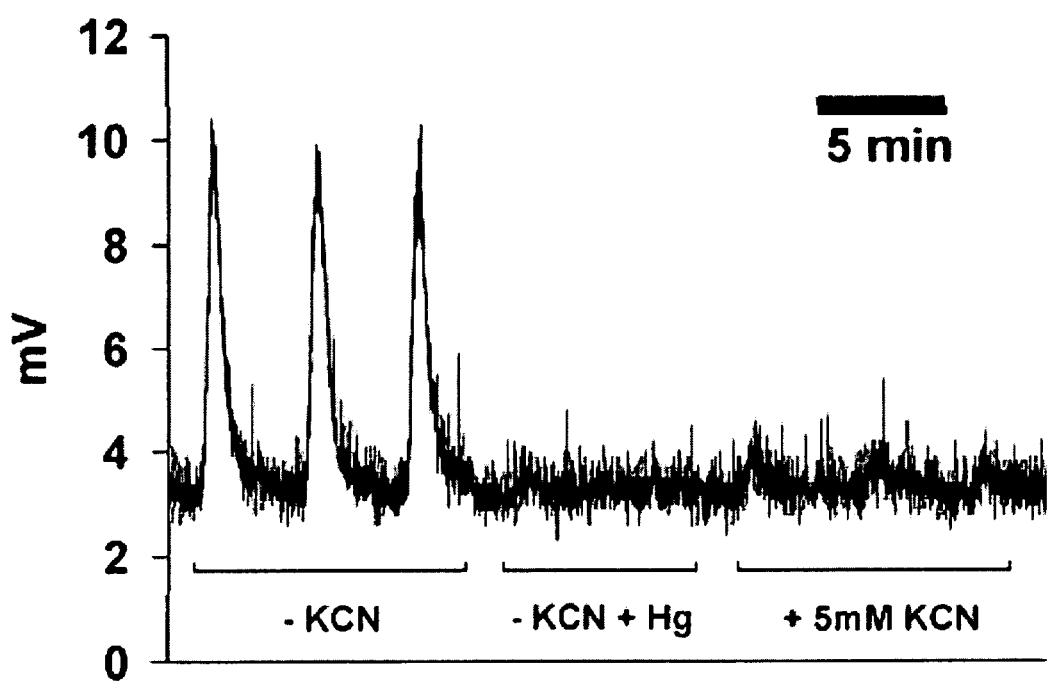
FIG. 12 is a graph showing the effect of KCN on nitrite-mediated SNO-Hb formation in 1 M phosphate buffer. The formation of SNO-Hb was measured during the reaction of 300 µM deoxygenated Hb (99.11±0.1% deoxy), 100 µM DTPA with 1 mM nitrite, in 1M phosphate buffer in the absence (−KCN) or presence (+KCN) of 5 mM KCN at pH 6.5 for 30 minutes at room temperature, followed by treatment with SNO-stabilizing solution for 1 hour (modified 2C assay). SNO-Hb was analyzed using the modified 2C assay. The figure represents one of three repeats of the experiment and shows the raw data of individual injections either directly (−KCN, +KCN) or treated with 5 mM HgCl$_2$ for 3 minutes (−KCN +Hg). SNO-Hb measured was 5.35±0.57 µM in the absence of KCN, and 0.70±0.02 µM in the presence of 5 mM KCN. The average SNO-Hb measured in three separate experiments was 5.7±0.3 µM in the absence of KCN, and 0.70±0.04 µM in the presence of 5 mM KCN. No SNO-Hb was detected in injections of +KCN treated with 5 mM HgCl$_2$ for 3 minutes.

If MetHb-$NO_2^-$ is involved in the formation of SNO-Hb then the binding of cyanide (CN) to the ferric heme should greatly reduce SNO-Hb formation. Since CN does not bind to ferrous hemes, it should not otherwise interfere with the nitrite-deoxyhemoglobin reaction. FIG. 7A shows that addition of KCN to the reaction mixture of deoxyhemoglobin and nitrite significantly lowered the SNO-Hb yield, confirming nitrite-MetHb participation. To ensure that the effect of KCN is not due an increase in pH, experiments like those shown in FIG. 7A were repeated using 1 M phosphate buffer. As shown in FIG. 12, KCN greatly reduces SNO-Hb formation without affecting pH.

The concentration of phosphate has been shown to influence $N_2O_3$ mediated nitrosation. In most cases, increasing the concentration of phosphate reduces $N_2O_3$ mediated nitrosation (DeMaster et al., *Biochem. Pharmacol.* 53:581-585, 1997; Singh et al., *Proc. Natl. Acad. Sci. USA* 93:14428-14433, 1996; Lewis et al., *J Am Chem Soc* 117:3933-3939, 1995) but under some conditions nitrosation can be enhanced (Dabora et al., *Iarc Scientific Publications* 311-316, 1984). The effect of incubating 300 µM deoxyHb with 1 mM nitrite for thirty minutes at pH 6.5 in either phosphate buffered saline (PBS: 10 mM phosphate) or 1 M phosphate (FIG. 7B) was therefore examined. The formation of SNO-Hb was increased in the presence of phosphate, consistent with other studies (Dabora et al., *Iarc Scientific Publications* 311-316, 1984). SNOHb formation was also measured in these two buffers after addition of the NO donor ProliNO to Nitrite-MetHb $NO_2^{III}$—$NO_2^-$; FIG. 7B). Consistent with the hypothesis that SNO-Hb formed in the nitrite-deoxyhemoglobin reaction relies on $N_2O_3$ generated in the reaction of NO with MetHb-$NO_2^-$, the addition of NO to Met-$NO_2^-$ resulted in SNO-Hb formation. Moreover, the dependence of SNOHb formation on phosphate concentration in the deoxyhemoglobin-nitrite reaction was identical to that of the MetHb-$NO_2^-$/ProliNO reaction, supporting a similar chemistry.

Examination of Other Proposed Mechanisms for Nitrite-Hemoglobin Dependent Nitrosation One proposed mechanism for SNO-Hb formation is the intra-molecular transfer of NO generated in the deoxyHb-nitrite reaction from the ferrous heme to the β-93 cysteine following the T-to-R conformational change upon hemoglobin oxygenation (Luchsinger et al., *Proc. Natl. Acad. Sci. USA* 100:461-466, 2003; Angelo et al., *Proc. Natl. Acad. Sci. USA* 103:8366-8371, 2006; Singel & Stamler, *Annu Rev Physiol* 67:99-145, 2005). However, such an allosterically-controlled intra-molecular transfer of NO from the heme to the cysteine during oxygenation is not observed by EPR and is not balanced electronically (Huang et al., *Blood* 107:2602-2604, 2006; Xu et al., *Proc. Natl. Acad. Sci. USA* 100:11303-11308, 2003). Moreover, this mechanism could not apply to the observations reported herein as the most nitrosation is observed under deoxygenated conditions—without subsequent oxygenation.

A second proposed mechanism for SNO-Hb formation in the nitrite-deoxyhemoglobin reaction is the formation of a MetHb bound with NO intermediate (HbFe$^{III}$—NO/HbFe$^{II}$—NO$^1$) that could lead to nitrosation (Equation 5) (Nagababu et al., *Nitric Oxide* 15:20-29, 2006; Angelo et al., *Proc. Natl. Acad. Sci. USA* 103:8366-8371, 2006).

$$HbFe^{III}NO + RSH \rightarrow HbFe^{II} + RSNO \qquad (5)$$

As the nitrosonium ion is not likely to survive in an aqueous environment, the nitrosonium transfer mechanism (Equation 5) is proposed to occur intra-molecularly to form SNO-Hb (Nagababu et al., *Nitric Oxide* 15:20-29, 2006; Angelo et al., *Proc. Natl. Acad. Sci. USA* 103:8366-8371, 2006). With subsequent binding of another NO, the nitrosonium transfer mechanism also encompasses reductive nitrosylation. One group has proposed that oxygen is necessary for this transfer (Angelo et al., *Proc. Natl. Acad. Sci. USA* 103:8366-8371, 2006), while another has proposed that oxygen inhibits the transfer (Nagababu et al., *Nitric Oxide* 15:20-29, 2006).

Figure 8A:
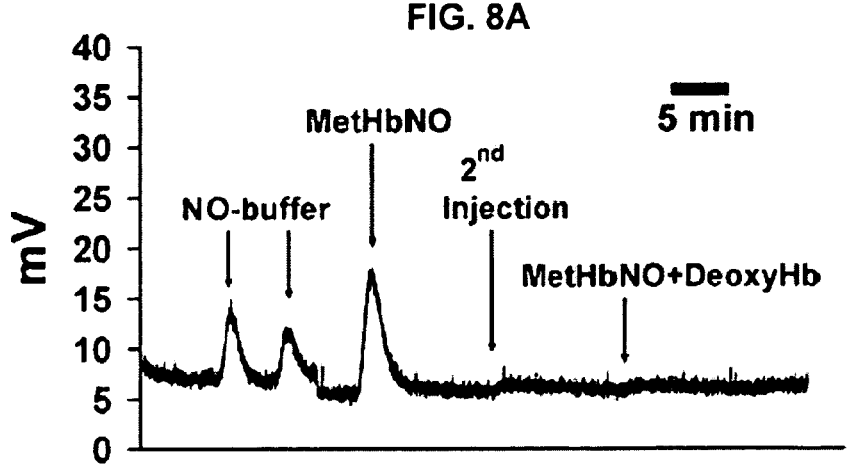
FIG. 8 is a series of graphs showing the absence of a stable HbFe$^{III}$—NO intermediate. (A) CO assay. Two 10 µL injections of partially NO saturated buffer (10 µM NO) followed by a single 10 µL injection of HbFe$^{III}$—NO (MetHbNO) into the NOA reservoir purged with a 1:1 mix of argon and CO. This sample was generated by incubation of 1 mM MetHb with 30 µM NO buffer followed by immediate injection into the NOA purge vessel. A second injection of this sample is also shown. Ferrous deoxyHb (100 µM final concentration) was added to a new reaction solution directly after addition of NO and immediately injected (MetHbNO+100 µM DeoxyHb). (B) EPR spectra for a sample obtained after adding NO to MetHb (MetHb+NO) and after subsequently adding ferrous deoxygenated Hb. The Fe$^{II}$NO-Hb spectrum in the "MetHb+NO" sample is secondary to the reductive nitrosylation reaction, while the spectrum in the "MetHb+NO+DeoxyHb" sample is most likely due to additional reductive nitrosylation and transfer of NO from EPR silent HbFe$^{III}$NO to Fe$^{II}$ hemes. (C) Progress of the reaction of deoxyHb (1 mM) with nitrite (250 µM) over 3 hours. Injections of 25 µM reaction aliquots into the pure CO assay were made at indicated time points. Long periods of time between consecutive injections were cut from the data shown.
Figure 8B:
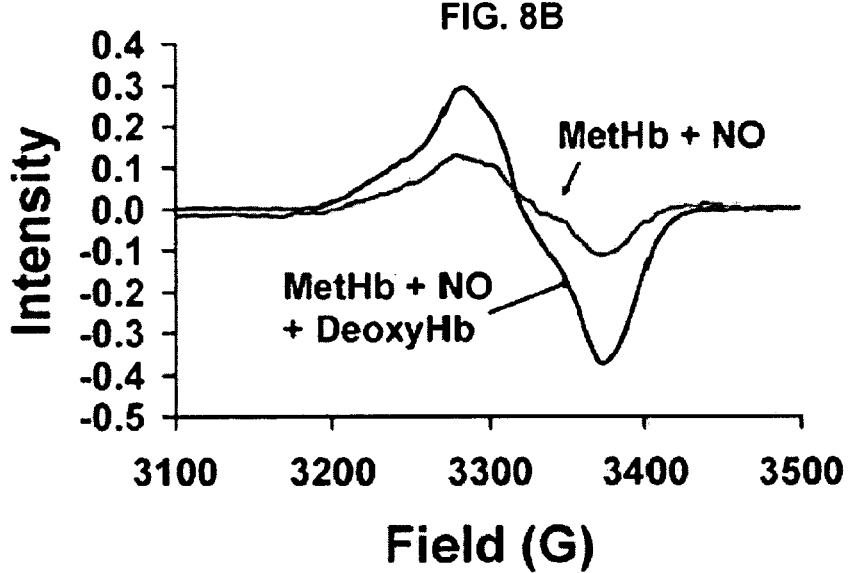
Figure 8C:
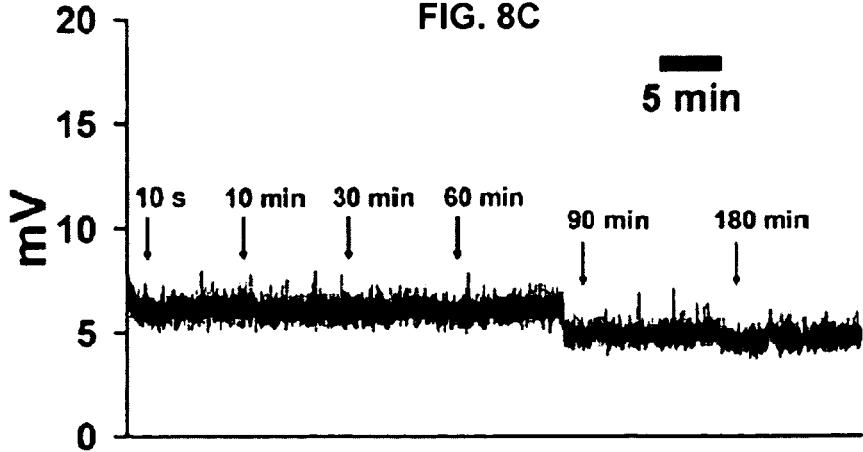

As described in FIG. 1, it was found that MetHb-$NO_2^-$ is the major spectral intermediate in the deoxyHb/nitrite reaction, rather than MetHb-NO. However, since it can be difficult to definitively identify minor species among many others using absorption spectroscopy, an additional sensitive and specific chemiluminescence-based assay for HbFe$^{III}$—NO was developed. Since NO dissociates from HbFe$^{III}$—NO at a rate of 1 s$^{-1}$ (Cooper, *Biochim. Biophys. Acta-Bioenerg.* 1411:290-309, 1999), HbFe$^{III}$—NO should be detectable when injected into a purge vessel in-line with a gas-phase chemiluminescent NO analyzer, without the need for any additional chemistry. To prevent capture of NO released from HbFe$^{III}$—NO by any ferrous deoxyhemoglobin present in solution, the NOA was purged with CO (mixed 1:1 with argon). The molar excess of CO would bind any ferrous hemes in milliseconds and thus prevent NO autocapture. FIG. 8A shows results from the validation of this assay. Partially saturated HbFe$^{III}$—NO was made by adding 10 to 30 µM NO to 1 mM MetHb. Based on the affinity of MetHb for NO (Cooper, *Biochim. Biophys. Acta-Bioenerg.* 1411:290-309, 1999), it was calculated that, for these conditions, approximately 80% of the added NO should be bound to the MetHb with the rest being free in solution. Within thirty seconds after NO addition to the MetHb, the sample was injected into the NOA. Overall, 78±39% recovery of the added NO was observed, indicating that most of the NO came from HbFe$^{III}$—NO. This signal decayed on the order of minutes as a second injection of the HbFe$^{III}$—NO produced a barely perceptible peak (FIG. 8A). The decay of the HbFe$^{III}$—NO signal was due to reductive nitrosylation, that generated HbFe$^{II}$—NO, which is not detectable in the CO-based chemiluminescence assay. These results were verified using EPR (FIG. 8B).

After this validation was performed, the stability of an HbFe$^{III}$—NO "intermediate" was tested in the presence of excess deoxyhemoglobin which is a necessary reactant in the deoxyhemoglobin-nitrite reaction. Based on the million-fold higher affinity of ferrous deoxyhemoglobin for NO compared to MetHb, and the fact that NO is released from MetHb at a rate of 1 s$^{-1}$ (Cooper, *Biochim. Biophys. Acta-Bioenerg.* 1411:290-309, 1999), one would not expect HbFe$^{III}$—NO to be stable in the presence of deoxyhemoglobin. To test this, 100 µM of ferrous deoxyHb was added to a new MetHb-NO sample followed by immediate injection of the mixture into the CO gas purging NOA system. The deoxyHb was added immediately after the NO, followed by injection into the NOA within thirty seconds. As shown in FIG. 8A, the mixture did not produce a signal in the NOA, indicating that all NO on the MetHb was quickly transferred to the added ferrous hemes. Finally, in order to examine whether any HbFe$^{III}$—NO accumulates in the nitrite-deoxyhemoglobin reaction, aliquots of a mixture of 1 mM deoxyHb and 250 µM nitrite were injected into the CO-purging NO analyzer at 10 seconds, and 1, 10, 30, 60, 90 and 180 minutes after the reaction began in pH 7.4 buffer. In all cases (n=3), no signal was observed in the NOA (representative data shown in FIG. 8C), indicating that HbFe$^{III}$—NO does not form as a stable or quasi-stable intermediate.

Another possible mechanism for SNO formation and reductive nitrosylation involves oxygen transfer (Equation 6).

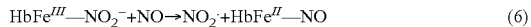

$$HbFe^{III}\text{—}NO_2^- + NO \rightarrow NO_2^- + HbFe^{II}\text{—}NO \qquad (6)$$

Oxygen transfer from nitrite to a variety of substrates including NO has been demonstrated for iron(III) porphyrins (Castro & Oshea, *J Org Chem* 60:1922-1923, 1995). In the context of nitrite-MetHb, oxygen transfer would directly lead to iron-nitrosyl-Hb and the NO$_2$ radical. A second NO could react with the NO$_2$ radical to form N$_2$O$_3$ with subsequent nitrosation. Alternatively, the NO$_2$ radical could oxidize cysteinyl thiol to form a thiol radical and a second NO could then react to form SNO-Hb. A similar route to SNO could take place when the NO$_2$ radical is released from N$_2$O$_3$.

A possible role of the oxygen transfer mechanism in the above-described Hb experiments was tested in two ways. Firstly, it was examined whether incubation of Nitrite-MetHb led to formation of iron-nitrosyl-Hb by following the reaction spectroscopically. This was done with several compounds shown to be efficient oxygen trapping substrates (Castro & Oshea, *J Org Chem* 60:1922-1923, 1995) including CO and dimethyl sulfide. In these experiments, no iron-nitrosyl-Hb formation was observed. In addition, there was no evidence for formation of dimethyl sulfoxide by gas chromatography after incubation of metHb-nitrite with dimethyl sulfide. Secondly, iron-nitrosyl-Hb formation was studied when $^{15}$N labeled nitrite bound to MetHb was combined with $^{14}$N nitric oxide. If the oxygen transfer mechanism (Equation 6) occurs, the iron nitrosyl would be entirely HbFe$^{II}$—$^{15}$NO, as it is derived from the nitrite. If, on the other hand, the Nitrite-MetHb+NO reaction to form N$_2$O$_3$ occurs (Equation 3), one would get HbFe$^{II}$—$^{14}$NO when the bound NO comes from that added to the nitrite-MetHb which could be mixed with some HbFe$^{II}$—$^{15}$NO if the bound NO comes from the N$_2$O$_3$. When treated to bring out the hyperfine structure, HbFe$^{II}$—$^{14}$NO produces a triplet whereas HbFe$^{II}$—$^{15}$NO produces a doublet in EPR (FIG. 9). Using isotope labeled nitrite, no evidence was found for oxygen transfer in the mechanism for reductive nitrosylation (and hence SNO formation) when NO is added to nitrite-MetHb (FIG. 9).

Example 3

Use of Inorganic Nitrite or Nitrite-Methemoglobin in a Cell-Free Blood Substitute This example demonstrates use of inorganic nitrite to detoxify a cell-free blood substitute to be administered to a subject in need of plasma expansion, tissue oxygenation, or treatment of another condition without concomitant vasoconstriction or resulting pathologies.

Nitrite Prevents Decreased Cardiac Output Resulting from Low-Level Hemolysis

Hemolysis is the rupturing of the erythrocyte membrane, and the subsequent release of free hemoglobin into the blood. Hemolysis results in a host of complications similar or identical to those resulting from transfusion with cell-free hemoglobin. As in cell-free hemoglobin transfusion, hemolysis introduces free hemoglobin into the blood where it scavenges nitric oxide and thereby causes vasoconstriction. Therefore, treatments that antagonize the vasoconstrictive effects of hemolysis by inhibiting the scavenging of nitric oxide by free hemoglobin are expected to be useful treatments for the detoxification of cell-free hemoglobin based blood substitutes.

Figure 16:
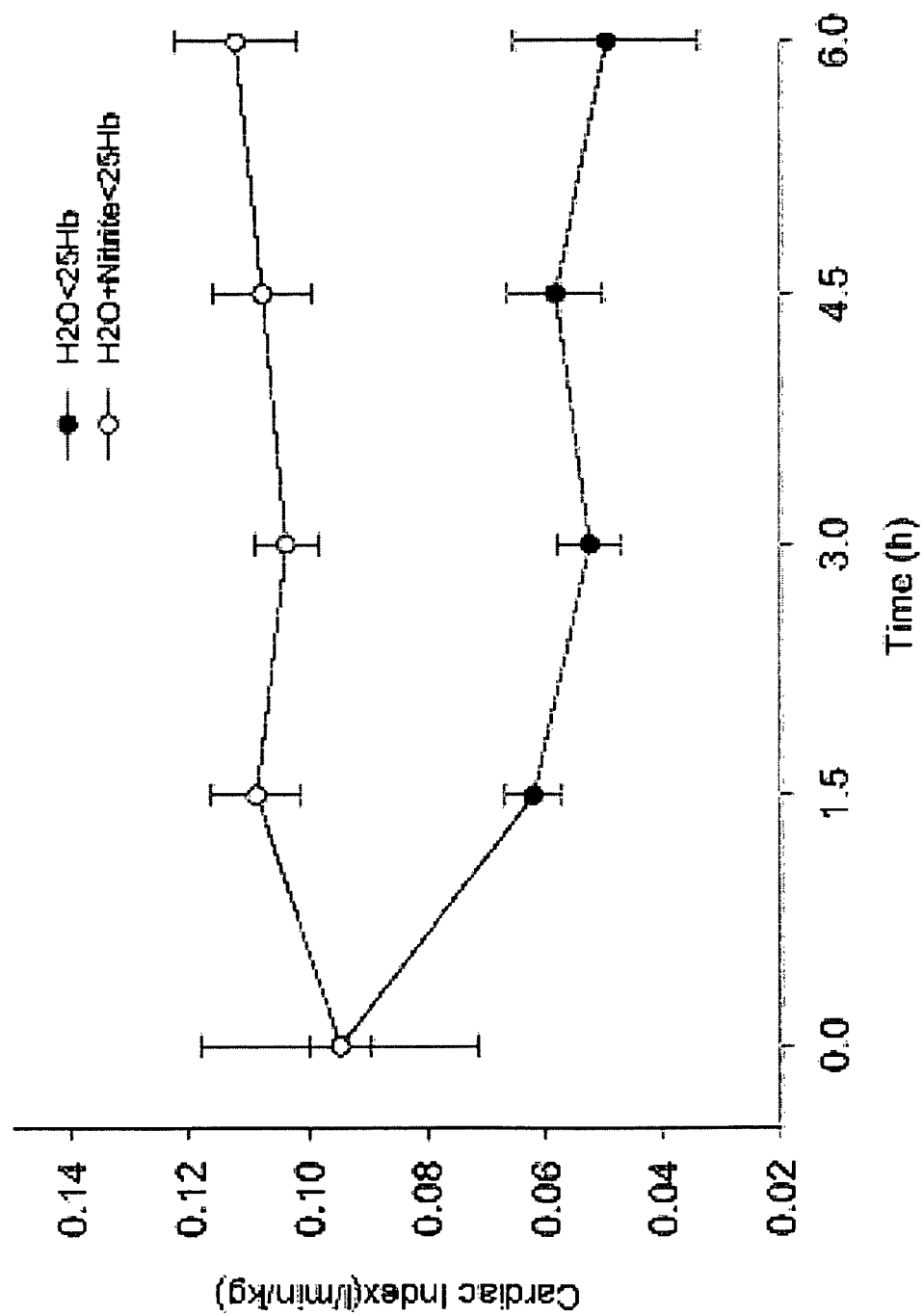
FIG. 16 is a graph showing data from a dog study in which hemolysis was induced using infusions of free water into the blood stream. Nitrite was infused at the same time. The effect of low-level hemolysis on decreasing cardiac output secondary to vasoconstriction and NO scavenging is shown. The addition of nitrite therapeutically reverses this effect.

Hemolysis was induced in dogs by infusing free water into the blood stream. The resulting osmotic pressure ruptured erythrocytes in vivo, releasing free hemoglobin. Consequently, cardiac output was reduced secondary to the primary effects of NO scavenging and vasoconstriction, but co-infusion with nitrite therapeutically reversed these effects (FIG. 16). This result demonstrates the therapeutic efficacy of nitrite in preventing NO scavenging and vasoconstriction by free hemoglobin in vivo.

Blood Substitute Comprising Nitrite Maintains Mean Arterial Blood Pressure During Trauma Hemorrhagic Shock and Resuscitation The toxicity of cell-free hemoglobin as a blood substitute is observed following resuscitation of a subject experiencing controlled hemorrhage as a restoration of mean arterial blood pressure above the normal range. Nitric oxide scavenging and vasoconstriction narrow the vasculature, thereby elevating blood pressure in the subject.

Figure 17:
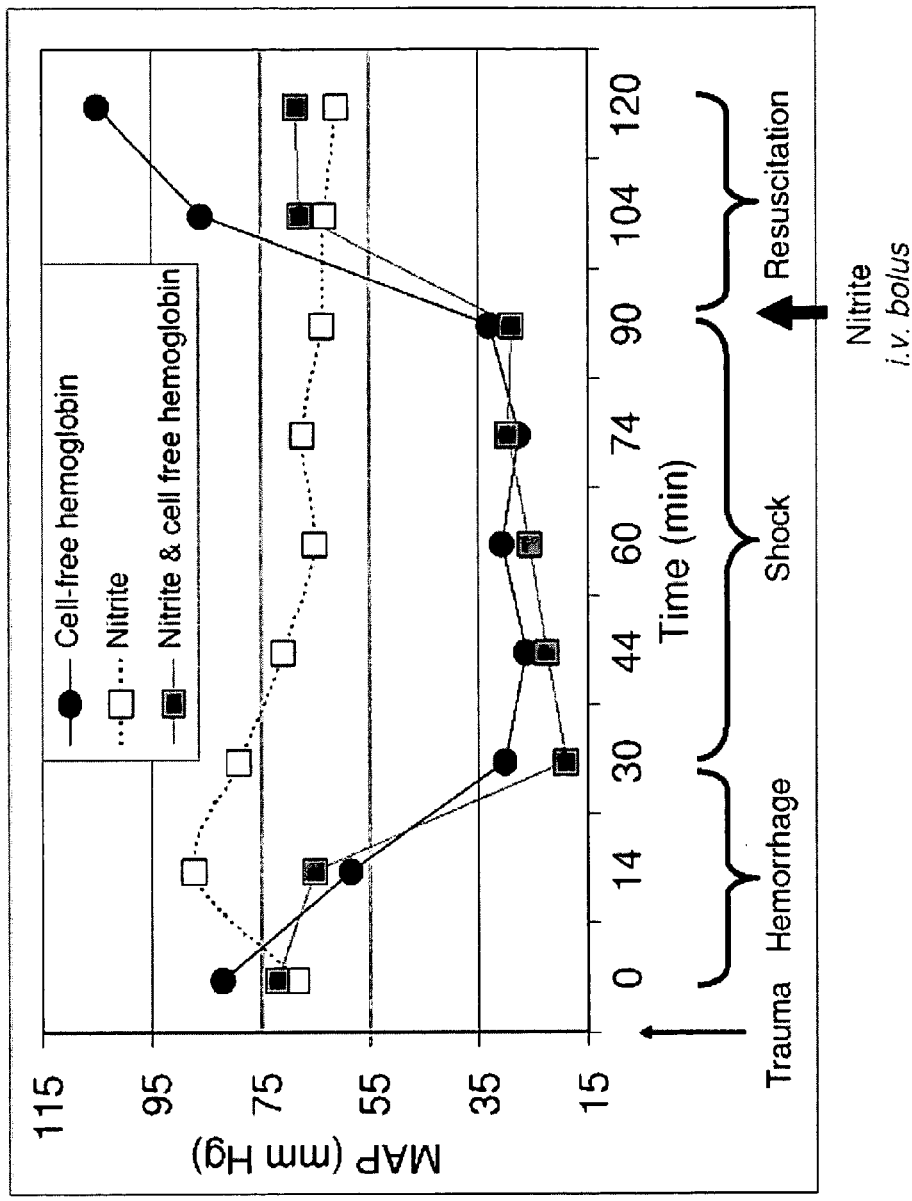
FIG. 17 is a graph showing the effect of resuscitating an animal with cell-free hemoglobin (stroma-free hemoglobin based oxygen carrier blood substitutes) with and without nitrite addition. After giving the hemoglobin, blood pressure improves but overshoots, while nitrite keeps the blood pressure normal. Sodium nitrite reduces final blood pressure following stroma-free hemoglobin resuscitation in a murine model of controlled hemorrhage, shock and resuscitation. The graph shows mean arterial pressure recorded in anesthetized mice treated at 90 minutes with i.v. bolus of sodium nitrite (final circulating concentrations 2 µM).

In a murine model of controlled hemorrhage, shock, and resuscitation, administration of a cell-free hemoglobin based oxygen carrier blood substitute indeed elevates mean arterial blood pressure in the resuscitated subject to more than 95 mm Hg, where approximately 75 mm Hg is the normal range (FIG. 17). Subjects receiving an i.v. bolus of nitrite experienced restoration of mean arterial blood pressure to the normal range (FIG. 17). This result demonstrates the utility of nitrite in the detoxification of cell-free hemoglobin based blood substitutes. In some embodiments, the detoxified blood substitute may be used as here, to resuscitate a subject following hemorrhage and shock.

Blood Substitute Comprising Nitrite Provides Superior Blood Oxygenation

It is an advantage of cell-free hemoglobin based blood substitutes detoxified by nitrite that free hemoglobin in the blood substitute catalyzes the generation of nitric oxide. Unexpectedly, this effect is only observed within the narrow range of nearly exact molar ratios of hemoglobin to nitrite. This result is shown in FIG. 18, where nearly exact ratios of nitrite and hemoglobin generate NO, and thereby inhibit mitochondrial respiration. Under conditions where there is almost half as much hemoglobin as nitrite, or more than twice as much, the effect is diminished (FIG. 18B). Without hemoglobin, or with a more than 5-fold molar excess, the effect is completely ablated.

Example 4

Hemodynamic Responses to Nitrite Infusion in a Canine Model

This example describes effects of sodium nitrite infusion in canines. Hemodynamic responses in study animals, including hemolysis, arterial pressure and vascular resistance, are described.

Physiologic Effects of Intravenous Sodium Nitrite

Figure 19B:
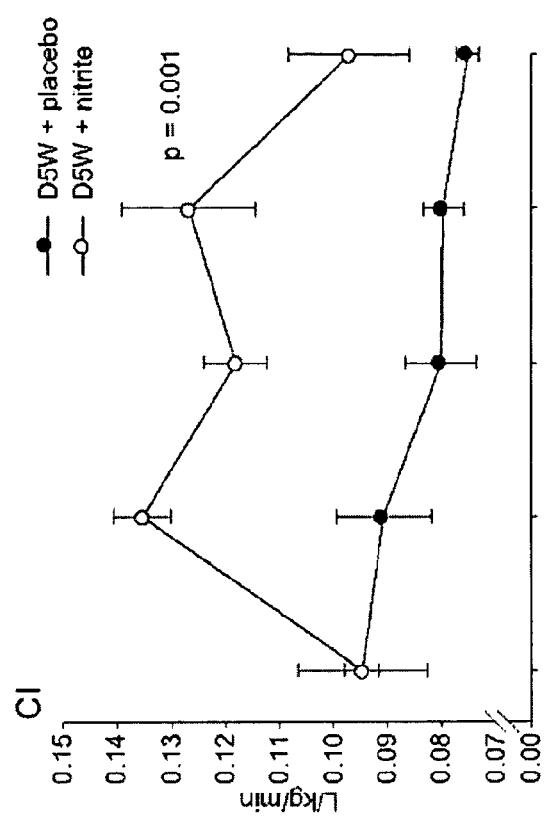
FIG. 19 is a series of graphs showing the cardiovascular effects of nitrite in non-hemolyzing animals. (A) Serial plasma nitrite levels (µM) in non-hemolyzing animals. In animals receiving a six hour infusion of 5% dextrose (D5W), a sodium nitrite infusion of 27.5 mg/h (open circles) led to a rapid rise and then a sustained plasma nitrite concentration (range: 15-21 µM) compared to a placebo infusion of 0.9% NaCl (closed circles). (B—H) In non-hemolyzing animals, sodium nitrite increased cardiac index (CI) and decreased systemic vascular resistance index (SVRI), pulmonary vascular resistance (PVRI), mean arterial pressure (MAP), mean pulmonary arterial pressure (PAM), central venous pressure (CVP), and pulmonary artery occlusion pressure (PAOP) compared to placebo. Intravenous nitrite enhanced cardiac performance (CI) by arterial vasodilation (SVRI, PVRI, MAP, PAM) and caused venodilation (CVP).
Figure 19A:
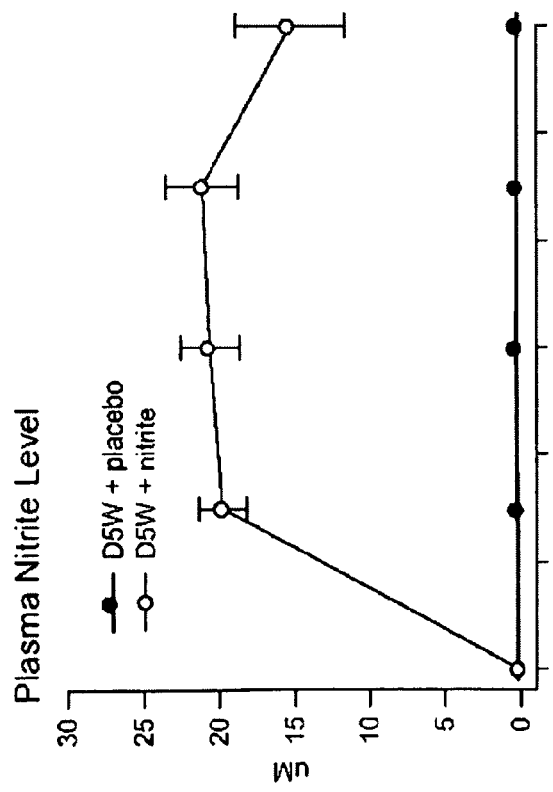
Figure 19F:
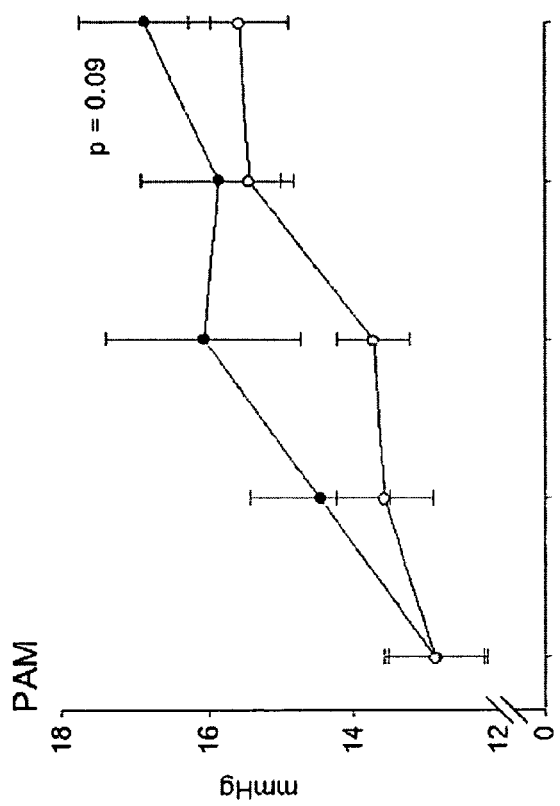
Figure 19E:
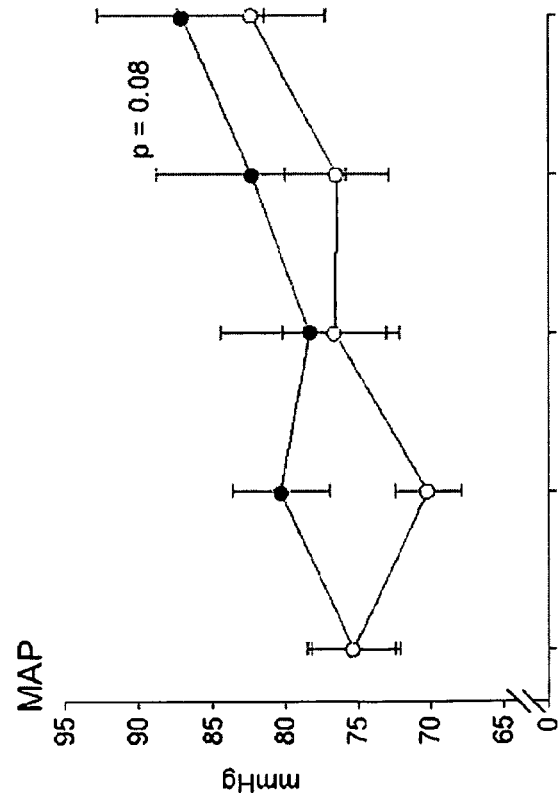

While many groups have now confirmed that sodium nitrite is a potent vasodilator in vivo, no group has characterized more specifically its activity in vivo as a relative arterial versus venous vasodilator or its effects on inotropy and chronotropy. Intravenous infusion of sodium nitrite (27.5 mg/h) rapidly increased plasma nitrite levels to a steady state concentration (range: 15-21 µM) that was maintained throughout the duration of the 6-hour infusion (FIG. 19A). In animals receiving a D5W infusion, sodium nitrite increased cardiac index (CI; p=0.001) and decreased systemic vascular resistance index (SVRI; p=0.04), pulmonary vascular resistance index (PURI; p=0.001), mean systemic arterial pressure (MAP; p=0.08), mean pulmonary arterial pressure (PAM; p=0.09), central venous pressure (CVP; p=0.01), and pulmonary artery occlusion pressure (PAOP; p=0.65) compared to placebo (normal saline) (FIGS. 19B-H). These physiologic effects suggest that low dose sodium nitrite is a more potent arterial vasodilator than a venodilator, and that nitrite increases cardiac performance by direct afterload reduction.

Figure 19H:
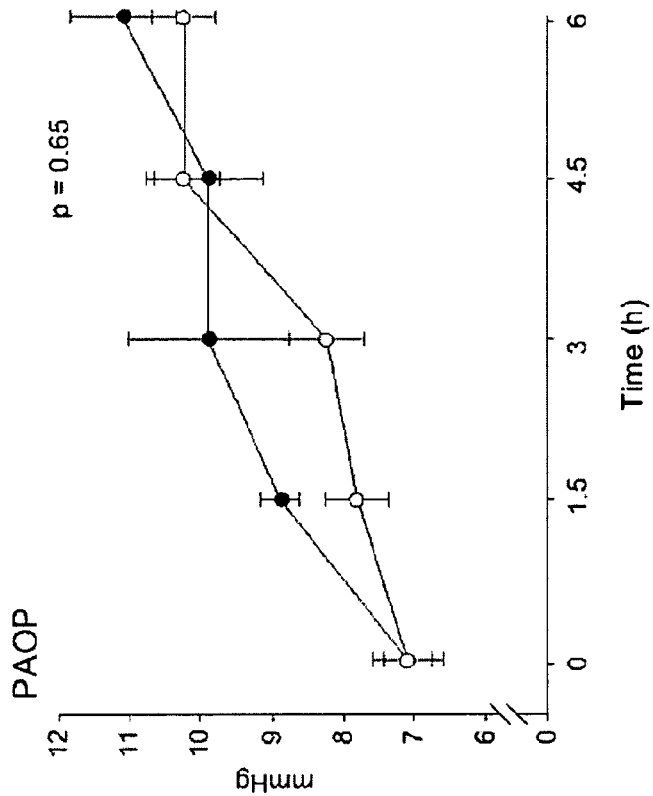
Figure 19G:
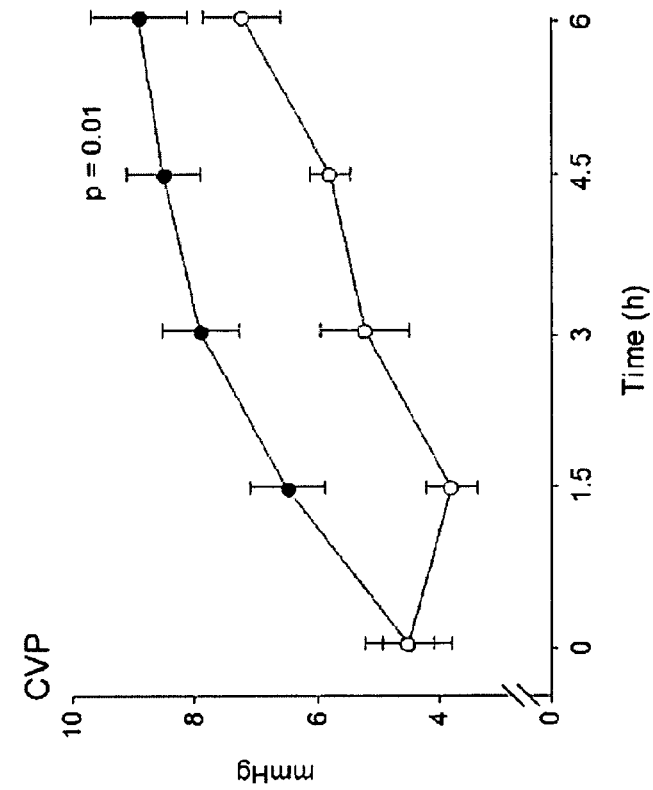
Figure 20A:
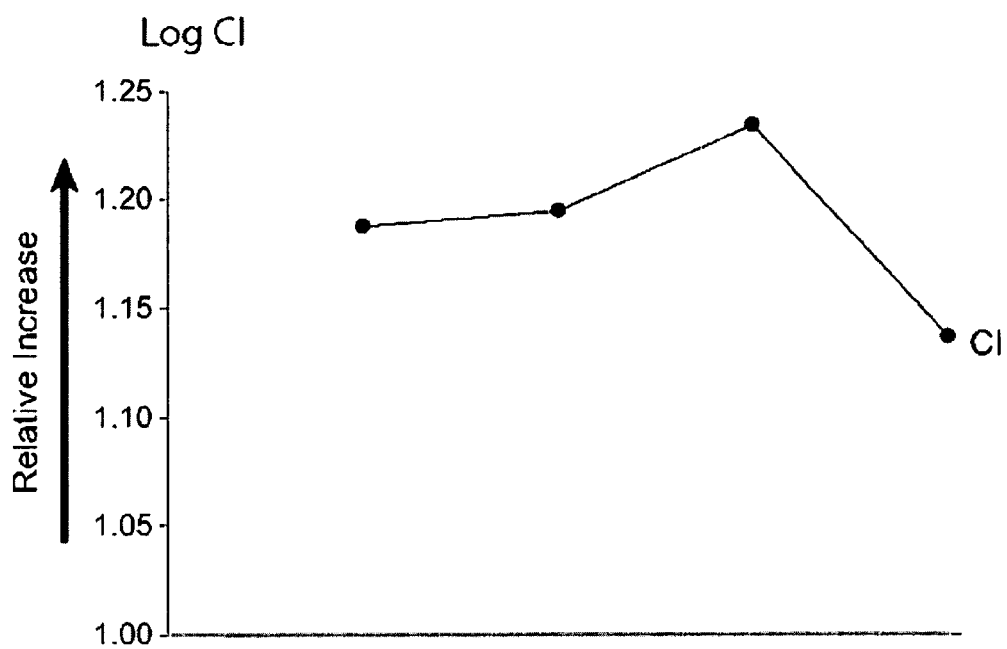
FIG. 20 is two graphs showing the effects of nitrite on the components of cardiac index in non-hemolyzing animals. Cardiac index (A) and its components (B) have been transformed into the log scale to demonstrate the individual contribution of heart rate (HR) and stroke volume index (SVI) to CI in additive fashion (normal scale: CI=SVI×HR; log scale: log CI=log SVI+log HR) (Rowland et al., *Pediatr. Cardiol.* 21:429-432, 2000). In animals receiving D5W and nitrite, the nitrite-induced increase in cardiac index is mediated predominantly through an increase in SVI and to a lesser extent by a chronotropic effect. Over time, the decrease in heart rate causes further increases in SVI by increasing diastolic filling time in the ventricles leading to higher end-diastolic volumes. Furthermore, the higher end-diastolic volumes translate into higher end-diastolic pressures which may explain the increase in PAOP over time (FIG. 19H).
Figure 20B:
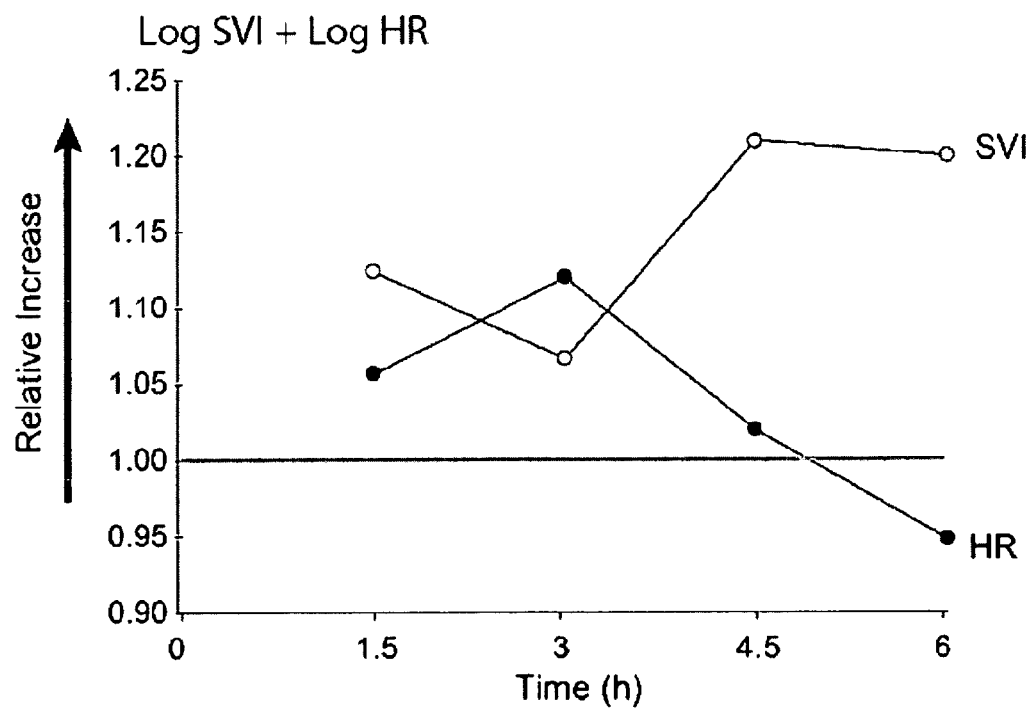

Supporting evidence for the vasodilatory effects of nitrite can be derived by examining the components of CI in the log scale (FIG. 20) (Rowland et al., *Pediatr. Cardiol.* 21:429-432, 2000). In this format, the individual contribution of each component of CI are additive (normal scale: CI=SVI×HR; log scale: log CI=log SVI+log HR). This transformation demonstrates that the nitrite-induced increase in CI is mediated predominantly through a sustained increase in stroke volume index (SVI) and to a lesser extent by a chronotropic effect. This transformation also accounts for the rise in PAOP during the last three hours of the study (FIG. 19H). The decrease in heart rate over time (an effect of anesthesia/analgesia seen in all groups in this model) (FIG. 20B) increases diastolic filling time in the ventricles leading to higher end-diastolic volumes and pressures that translate into increases in PAOP and further increases in SVI. These data imply that nitrite enhances cardiac performance by afterload reduction through an arterial vasodilatory mechanism. These data also indicate that isolated measures of MAP in animal studies may fail to sensitively assess the magnitude of nitrite-dependent vasodilation because of the rise in cardiac index.

Physiologic Effects of Sodium Nitrite During Intravascular Hemolysis

In previous intravascular hemolysis experiments (Minneci et al., *J. Clin. Invest.* 115:3409-3417, 2005) and in the current experiments, cell-free plasma hemoglobin increased systemic and pulmonary arterial pressures, systemic and pulmonary vascular resistance, and pulmonary arterial occlusion pressure (Table 1; p=0.04, 0.14, 0.06, 0.42, and 0.21 respectively for the interaction of hemolysis level and the mean change in each physiologic variable during baseline and intervention studies). If nitrite functioned purely as an NO donor medication, one would expect the vasoconstrictive effects of intravascular hemolysis to attenuate the vasodilatory effects of nitrite because any NO generated from nitrite would be readily scavenged by the cell-free plasma hemoglobin. However, in these experiments, the physiologic effects of nitrite were not simply inhibited by increasing levels of hemolysis.

TABLE 1

Physiological effects of intravascular hemolysis
(Mean change during 6 hour intervention study)

| Level of hemolysis | MAP (mmHg) | PAM (mmHg) | SVRI (dynes/sec/*cm$^{-5}$) | PVRI (dynes/sec/*cm$^{-5}$) | PAOP (mmHg) |
|---|---|---|---|---|---|
| zero (n = 5) | 6.7 | 3.0 | 15.1 | 1.3 | 2.9 |
| <25 µM (n = 4) | 7.9 | 4.2 | 28.1 | 3.0 | 2.8 |
| >25 µM (n = 4) | 16.4 | 4.8 | 33.9 | 2.3 | 3.8 |

Figure 21G:
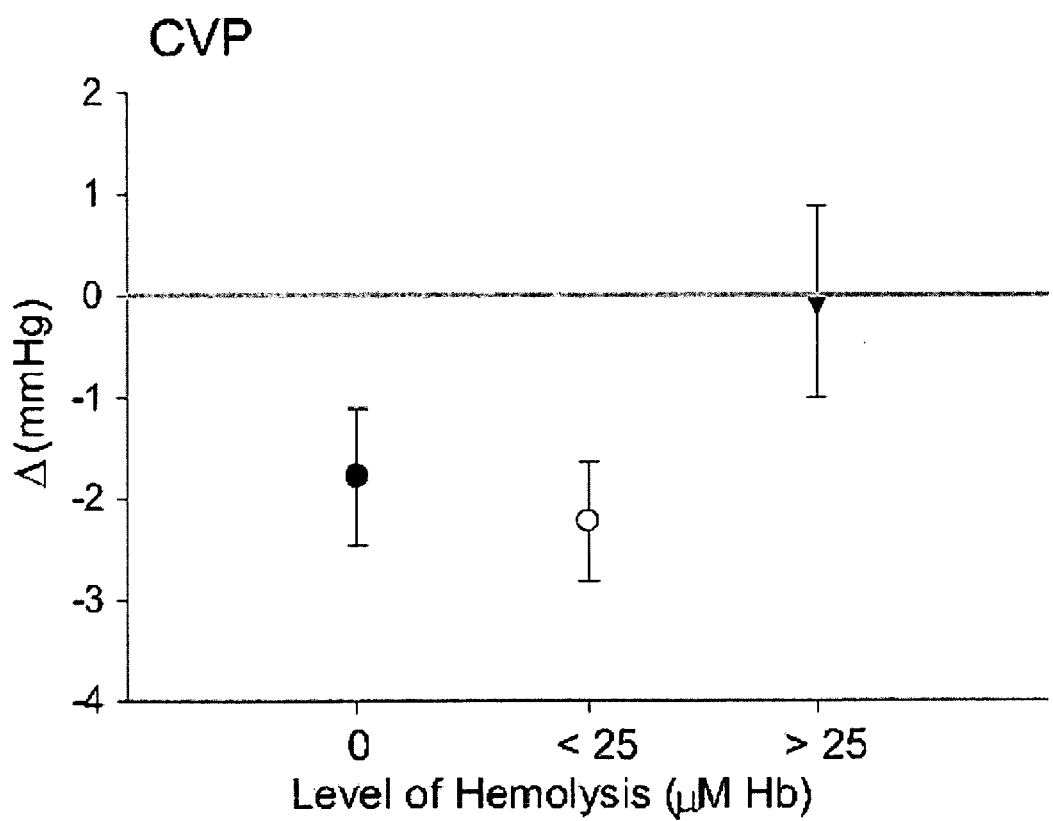
FIG. 21 is a series of graphs showing the cardiovascular effects of nitrite during intravascular hemolysis. The cardiovascular effects of nitrite (27.5 mg/hr) at different levels of cell-free plasma hemoglobin (zero, <25 µM, and >25 µM) are shown (A-G). For each parameter, the isolated effect of nitrite is displayed after controlling for animal variability and the independent effects of hemolysis. The depicted value represents the mean change in the parameter from time zero to 1.5, 3, 4.5 and 6 h for all animals within the specified hemolysis group (x-axis, zero=closed circles, <25 µM=open circles, and >25 µM=closed triangles). According to previous experiments, if nitrite functioned purely as an NO donor, then there should progressive attenuation of the vasodilatory effects of nitrite with increasing levels of hemolysis; the NO generated from nitrite should be progressively scavenged by the increasing levels of cell-free plasma hemoglobin (Minneci et al., *J. Clin. Invest.* 115:3409-3417, 2005). In these experiments, the effect of nitrite was dependent on the level of intravascular hemolysis ($p=0.01$ for a differing effect of nitrite at low level hemolysis compared to zero and high level hemolysis across the 7 physiologic variables combined). A consistent U-shaped relationship between the physiologic effects of nitrite and the levels of cell-free plasma hemoglobin was detected. At low levels of hemolysis (Hb concentration <25 µM), the vasodilatory effects of nitrite were potentiated, whereas with higher levels of hemolysis (cell-free plasma Hb>25 µM), the expected inhibition of the vasodilatory effects of nitrite were observed.

MAP: mean systemic arterial pressure;
PAM: mean pulmonary arterial pressure;
SVRI: systemic vascular resistance index;
PVRI: pulmonary vascular resistance index;
PAOP: pulmonary artery occlusion pressure In fact, the effect of nitrite was dependent on the level of intravascular hemolysis in an unusual way (FIG. 21). A consistent U-shaped relationship was detected between the physiologic effects of nitrite and the levels of cell-free plasma hemoglobin suggesting an interaction between the effects of nitrite and the amount of intravascular hemolysis (FIG. 21; p=0.01 for a differing effect of nitrite at low level hemolysis compared to zero and high level hemolysis across the 7 physiologic variables combined). At low levels of hemolysis (Hb<25 µM), the vasodilatory effects of nitrite are apparently potentiated, whereas with higher levels of hemolysis (Hb>25 µM), the expected inhibition of the vasodilatory effects of nitrite are observed. These results suggest that there are two reactions that regulate the availability of NO at the smooth muscle: the reaction of hemoglobin with nitric oxide and an opposing reaction of nitrite with deoxyhemoglobin that generates NO. The results described herein demonstrate that at low levels of hemoglobin, the physiologic effects of the latter reaction are detected; however with increasing hemoglobin concentration, the former reaction dominates. These effects are examined more closely and compared with the NO donor sodium nitroprusside in additional experiments described below.

Nitrite Levels and Hemoglobin Species Formed During Intravascular Hemolysis

In animals receiving nitrite, plasma nitrite levels were similar and were maintained within a range of 16-20 µM throughout the six hour experiment (FIG. 22 and FIG. 19A). Intravascular hemolysis occurred at varying rates (FIG. 22). Animals receiving D5W and nitrite represent the zero hemolysis control group with all measured cell-free plasma hemoglobin levels <5 µM. In animals receiving water and nitrite infusions with low levels of hemolysis (Hb<25 µM), the average peak cell-free plasma hemoglobin level was 20 µM. In animals receiving water and nitrite infusions with high levels of hemolysis, the average peak cell-free plasma hemoglobin level was 142 µM. In animals receiving D5W and nitrite (zero hemolysis), 81% of the measured cell-free plasma hemoglobin was oxyhemoglobin (FIG. 22, values depicted as a red reference line in FIG. 22B and FIG. 22E), consistent with observations in normal volunteers and sickle cell patients that plasma hemoglobin is maintained largely in the reduced or ferrous-oxygen bound state ($HbFe^{+2}—O_2$). In hemolyzing animals, oxyhemoglobin accounted for 71% and 69% of the measured cell-free plasma hemoglobin in animals with low and high levels of hemolysis respectively (FIG. 22).

Figure 22C:
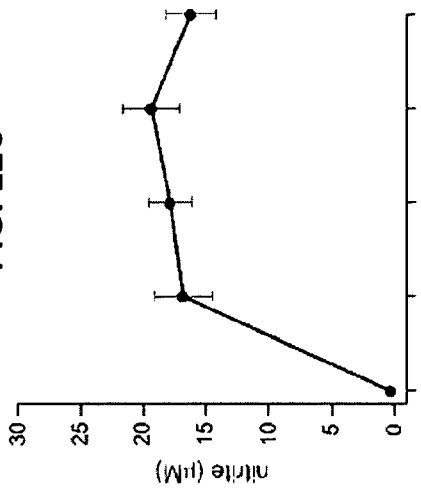
FIG. 22 is a series of graphs showing nitrite levels and plasma hemoglobin composition during intravascular hemolysis. (A, D) Intravascular hemolysis occurred at varying rates in animals receiving water and nitrite infusions. In the low level hemolysis group (Hb<25 µM; A), the average peak cell-free plasma hemoglobin level was 20 µM; in the high level hemolysis group (Hb>25 µM; D), the average peak cell-free plasma hemoglobin level was 142 µM. Animals receiving D5W and nitrite represent the zero hemolysis control group with all measured cell-free plasma hemoglobin levels <5 µM. (B, E) Total plasma hemoglobin composition in the low (B) and high (E) hemolysis groups (open circles=methemoglobin; closed circles=oxyhemoglobin). In animals receiving D5W and nitrite (zero hemolysis), 81% of the measured cell-free plasma hemoglobin was oxyhemoglobin (depicted as red reference lines) and 19% was methemoglobin. With increasing hemoglobin concentrations, the rate of methemoglobin formation increased from zero to 3 hours (p=0.0001) producing higher levels of methemoglobin from 3 to 6 hours (p=0.0001) in animals with higher levels of hemolysis compared to animals with lower levels of hemolysis. These results can be explained by the fact that the overall reactions of nitrite with oxy- and deoxy- hemoglobin are second order during their lag phases such that increasing hemoglobin concentrations lead to increasing rates of reaction. (C, F) In both the low and high level hemolysis groups, plasma nitrite levels were similar and were maintained within a range of 16-21 µM throughout the six hour experiment.
Figure 22B:
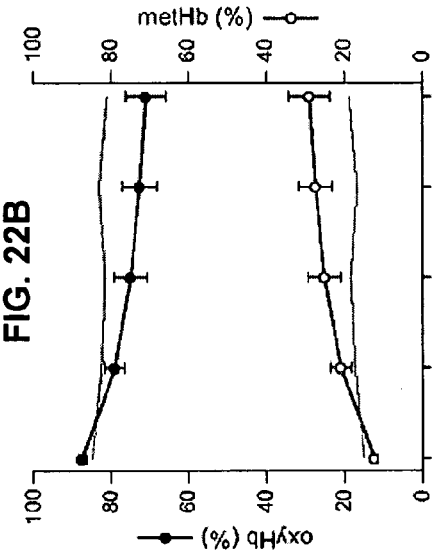
Figure 22A:
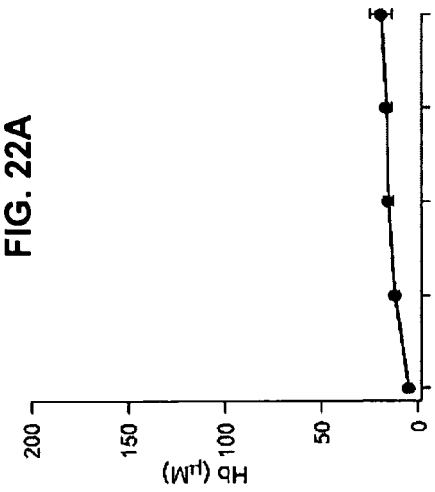
Figure 22F:
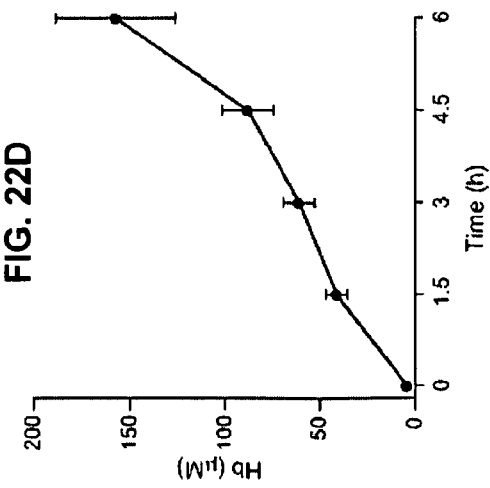
Figure 22E:
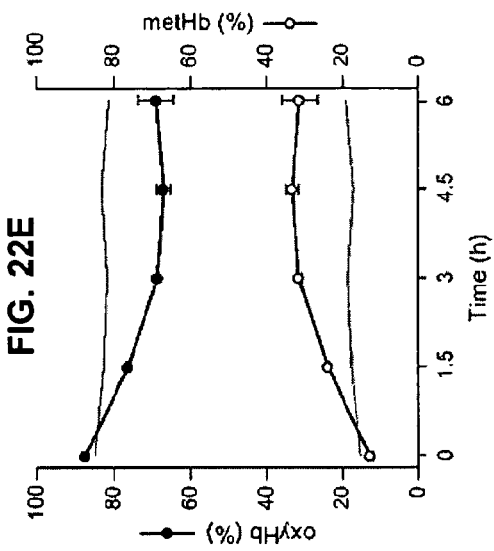
Figure 22D:
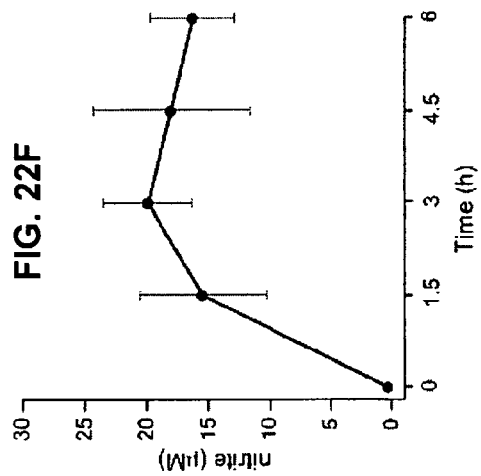
Figure 23D:
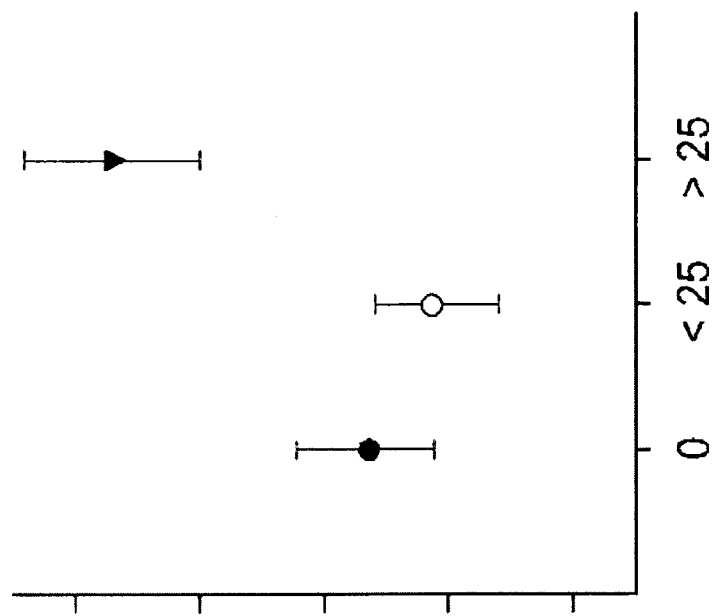
FIG. 23 is a series of graphs showing the effects of nitrite and intravascular hemolysis on cardiovascular responses to sodium nitroprusside. The physiologic effects of sodium nitroprusside (a direct NO donor) were dependent on the level (or dose) of hemolysis and the presence of sodium nitrite (p=0.09, 0.05 and 0.009 for interaction between level of hemolysis and nitrite on the effect of sodium nitroprusside for CI, SVRI, and PVRI respectively). The depicted value represents the mean percent change in the parameter for all doses of nitroprusside for all animals within the specified hemolysis group (zero=closed circles, <25 µM=open circles, and >25 µM=closed triangles). As expected for a direct NO donor, in animals not receiving nitrite, sodium nitroprusside-induced increases in CI and decreases in SVRI and PVRI were progressively inhibited by increasing levels of hemolysis (A, C, E). Compared to the non-hemolyzing animals not receiving nitrite (zero-hemolysis, no nitrite), the nonhemolyzing animals receiving nitrite (zero-hemolysis, nitrite) demonstrated blunted effects of sodium nitroprusside on CI, SVRI and PVRI suggesting a decreased vasodilator effect of the donated nitric oxide in the presence of nitrite (A vs. B, C vs. D, and E vs. F). In the animals receiving nitrite, the effects of sodium nitroprusside on CI, SVRI, and PVRI were accentuated with low levels of hemolysis (Hb<25 µM, nitrite) and attenuated with high levels of hemolysis (Hb>25 µM, nitrite) compared to non-hemolyzing animals (zero hemolysis, nitrite) (B, D, F).
Figure 23C:
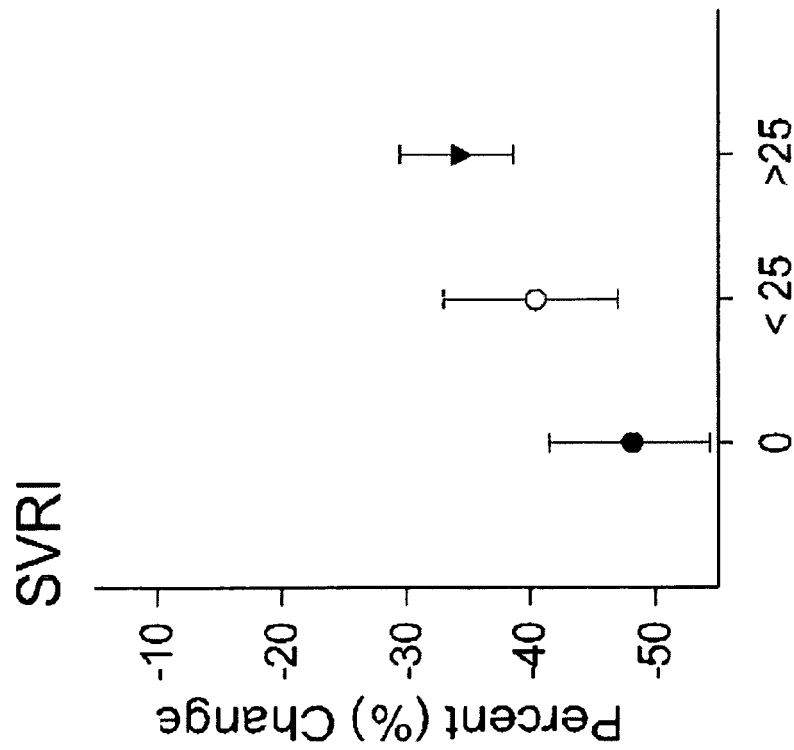
Figure 23F:
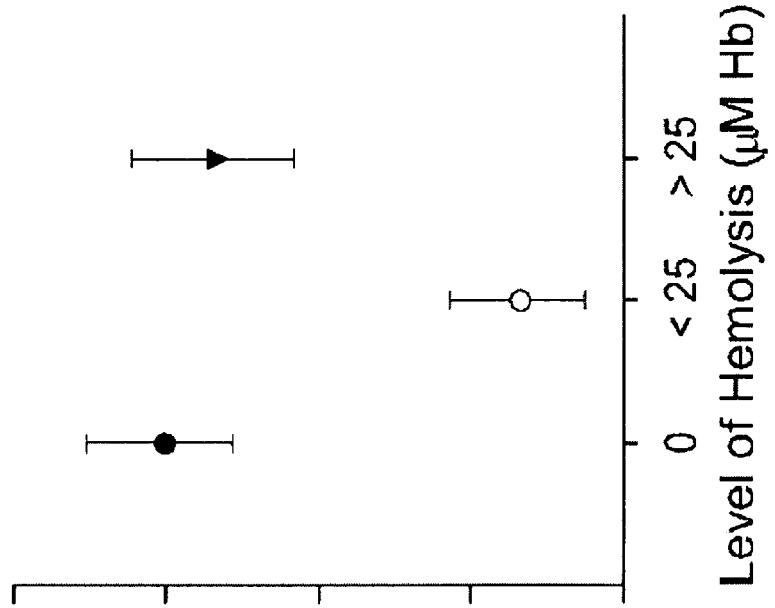
Figure 23E:
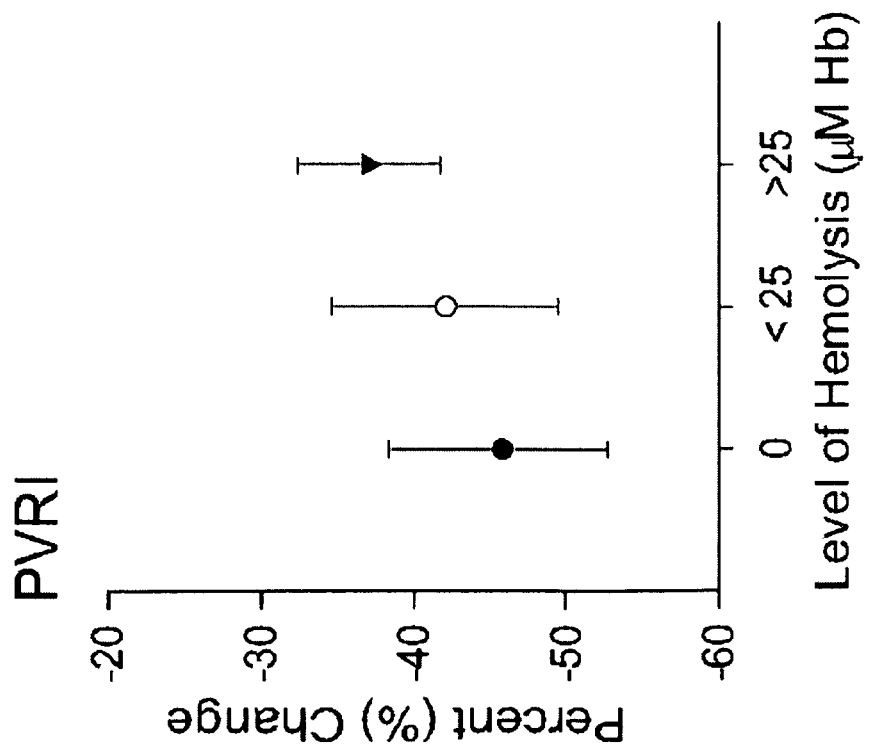

During nitrite infusions at low levels of hemolysis, the nitrite reacted with hemoglobin to form approximately 30% methemoglobin (FIG. 22; values for the D5W+nitrite zero-hemolysis control are depicted as a blue reference line in FIG. 22B and FIG. 22E). This reaction likely reflects two reactions of nitrite: the reaction of nitrite with oxyhemoglobin to form methemoglobin and nitrate ($NO^{2-}+HbO_2$. $MetHb+NO^{3-}$) and the reaction of nitrite with deoxyhemoglobin to form methemoglobin and NO. The former reaction will decrease NO scavenging and the latter reaction will contribute to NO generation. Note that paradoxically there is sufficient oxyhemoglobin at the end of 6 hours to almost completely scavenge and inhibit any NO that might form, yet the nitrite remains vasoactive and potentiated by low levels of hemoglobin (FIG. 21). As shown in FIG. 22B and FIG. 22E, with increasing hemoglobin concentrations, the rate of methemoglobin formation increases from zero to 3 hours (p=0.0001) producing higher levels of methemoglobin from 3 to 6 hours (p=0.0001) in animals with higher levels of hemolysis compared to animals with lower levels of hemolysis. This is because the overall reactions of nitrite and hemoglobin are second order during their lag phases, meaning that as hemoglobin concentration increases the rate of the reactions increase. Again, the amount of oxyhemoglobin at the end of the reaction is sufficient to almost completely scavenge any NO that might be formed if nitrite acted as a pure NO donor.

Effects of Nitrite and Level of Hemolysis on Hemodynamic Responses to Sodium Nitroprusside, an Infused NO Donor Sodium nitroprusside was administered to all animals to determine the physiologic effects of a direct NO donating agent in the setting of hemolysis with and without sodium nitrite. The physiologic effects of sodium nitroprusside were dependent on the level (or dose) of hemolysis and the presence of nitrite. As expected, in animals that did not receive nitrite, sodium nitroprusside-induced increases in CI and decreases in SVRI and PVRI were progressively inhibited by increasing levels of hemolysis, suggesting progressive consumption of the donated NO by increasing levels of cell-free plasma hemoglobin during intravascular hemolysis (FIG. 23). In contrast, the effects of sodium nitroprusside at the three levels of hemolysis were different in animals receiving nitrite compared to the animals not receiving nitrite (FIG. 23). Compared to the nonhemolyzing animals not receiving nitrite (zero-hemolysis, no nitrite), the non-hemolyzing animals receiving nitrite (zero-hemolysis, nitrite) demonstrated blunted effects of sodium nitroprusside on CI, SVRI and PVRI suggesting a decreased vasodilator effect of the donated NO in the presence of nitrite without hemolysis.

If the effect of nitrite on the response to sodium nitroprusside during hemolysis was additive (i.e. same effect at all levels of hemolysis), then the demonstrated relationship should be a similar linear relationship to the one demonstrated in the animals not receiving nitrite, but starting at a smaller magnitude percent change due to the decreased vasodilator effect of the donated NO from nitroprusside in the presence of nitrite (comparing zero hemolysis no nitrite to zero hemolysis+nitrite). However, in the animals receiving nitrite, the effects of sodium nitroprusside on CI, SVRI, and PVRI were accentuated with low levels of hemolysis (Hb<25 µM, nitrite) and then attenuated with high levels of hemolysis (Hb>25 µM, nitrite) compared to non-hemolyzing animals (zero hemolysis, nitrite) (FIGS. 23; p=0.09, 0.05 and 0.009 for the interaction demonstrating a different relationship between level of hemolysis and nitrite on the effect of sodium nitroprusside for CI, SVRI, and PVRI respectively). Animals with low level hemolysis demonstrated a similar or greater percent change on the physiologic variables than zero hemolysis (instead of the expected smaller effect in an additive model) and animals with higher level hemolysis demonstrated blunted physiologic responses. This interaction is consistent with the U-shaped physiologic effects of nitrite demonstrated during the 6-hour hemolysis study; compared to the effect in animals with zero hemolysis, the physiologic effect of nitrite is accentuated with low level hemolysis and then attenuated at higher levels of hemolysis. This interaction may be explained by the additional nitrite reduction reaction with hemoglobin contributing to vasodilation.

Nitrite reacts with oxy- and deoxy-hemoglobin to form methemoglobin and methemoglobin+NO respectively (Cosby et al., Nat. Med. 9:1498-1505, 2003). These nitrite reactions may lead to enhanced vasodilation by sodium nitroprusside in the setting of low levels of hemolysis by: 1) minimizing the amount of oxyhemoglobin available in the plasma to consume the donated NO from sodium nitroprusside and 2) by directly causing vasodilation secondary to the NO generated by the reaction of nitrite with deoxyhemoglobin. At higher levels of intravascular hemolysis, the nitrite reduction reaction with hemoglobin may be overwhelmed by the large amounts of cell-free plasma hemoglobin that consume any NO formed from the reaction. Consequently the donated NO from sodium nitroprusside and the generated NO from the reaction of nitrite with deoxyhemoglobin are consumed by the excess oxyhemoglobin in the plasma.

Confirmatory In Vitro Mitochondrial Respiration Experiments

In vitro mitochondrial respiration experiments were performed with nitrite and cell-free hemoglobin levels similar to those obtained in vivo to confirm that the effects of nitrite on vasoactivity during hemolysis are dependent on the reaction of nitrite and deoxyhemoglobin to generate NO. In these experiments, mitochondria serve as NO sensors because NO avidly binds to cytochrome-C oxidase to inhibit respiration. In this experimental system, mitochondria suspended in a closed chamber respire until the chamber becomes anoxic (oxygen trace reads zero). Removal of the chamber lid allows oxygen diffusion into the chamber; however the trace remains at zero due to rapid oxygen consumption by the respiring mitochondria. The oxygen trace deviates from zero only once the mitochondria stop respiring due to the exhaustion of substrate or inhibition (FIG. 18A). Time to inhibition (oxygen reaccumulation) should be dependent on the rate of NO production from reactions of nitrite with deoxyhemoglobin and the rate of NO consumption by excess oxyhemoglobin.

With the addition of nitrite (18 µM) and low levels of hemoglobin (10-20 µM), mitochondrial respiration was inhibited in comparison to mitochondria with nitrite or hemoglobin alone. The shortest time to inhibition was observed with nitrite and 20 µM hemoglobin, above which increasing concentrations of hemoglobin resulted in longer times to inhibition (FIG. 18B). These mitochondrial inhibition experiments demonstrate a U-shaped relationship between nitrite and hemoglobin level consistent with the results of the in vivo experiments described above. The animal experiments suggest an interaction between the effects of nitrite and the level of hemolysis such that low levels of hemolysis accentuate the vasodilatory effects of nitrite.

These mitochondrial experiments demonstrate that NO generation and accumulation from nitrite reduction by hemoglobin is maximal at low levels of hemolysis and decreases with higher levels of hemolysis. These results suggest that the in vivo accentuated vasodilatory effects of nitrite during low levels of hemolysis may be mediated by the generation of NO from the reduction of nitrite by hemoglobin.

Example 5

Administration of a Cell-Free Blood Substitute Detoxified by Nitrite to a Human Subject This example describes that a cell-free blood substitute can be detoxified by nitrite and used for treating oxygen deficiency or replacing lost blood in a human subject.

Patient Selection

In one embodiment, the human subject is a human diagnosed with hypoxia, hypoxemia, ischemia, anoxia or another disease for which treatment includes increasing blood oxygenation by administration of a blood substitute, and wherein the human subject is, has been, or will be treated with transfusion of whole blood or a blood substitute. In another embodiment, the human subject is afflicted or is predisposed to being afflicted with a disease or condition treatable by transfusion of whole blood or a blood substitute, for example, anemia, bleeding disorders, burns, coagulopathy, ectopic pregnancy, favism, gastrointestinal bleeding, hemolytic uremic syndrome, hemophilia, microcytosis, ulcer, hemorrhage, rhabdomyolysis, hemorrhagic shock, sickle cell anemia, spherocytosis, thalassemia, or yellow fever. In a further embodiment, the human subject is undergoing, or has undergone, a surgical procedure wherein a clinically dangerous amount of blood has been lost, or wherein a clinically dangerous amount of blood may be lost. In such embodiments, the human subject may develop shock immediately after blood loss occurs, shortly after blood loss occurs, or a longer period of time after blood loss occurs. In some embodiments, the human subject may need to be resuscitated.

In most embodiments, the human subject is under the care of a physician. The physician can identify the presence of a disease or condition treatable by transfusion of whole blood or a blood substitute in the subject according to any methods disclosed above or known to one skilled in the art. A representative method of treatment for such diseases is by administration of a cell-free hemoglobin based blood substitute detoxified by nitrite. The physician can also assess the severity of blood loss in a human subject according to methods known to one skilled in the art, and determine the necessity of blood replacement. A representative method for blood replacement in such subjects is by administration of a cell-free hemoglobin based blood substitute detoxified by nitrite.

Administration of Cell-Free Hemoglobin Based Blood Substitute Detoxified by Nitrite to a Human Subject A therapeutically effective amount of a cell-free hemoglobin based blood substitute detoxified by nitrite is administered to the human subject. In some embodiments, the blood substitute is detoxified by pretreatment with nitrite. In other embodiments, nitrite is co-administered with the blood substitute to detoxify the blood substitute. The cell-free hemoglobin based blood substitute is administered according to any method known to one skilled in the art. For example, in some embodiments the blood substitute is administered intravenously. In other embodiments, the blood substitute is administered intraarterially. In further embodiments, the blood substitute is administered according to any technique appropriate for transfusion of whole blood.

For example, two i.v. bags of cell free hemoglobin would be prepared: one bag would contain ferric methemoglobin ($Fe^{III}$) with nitrite (at a ratio of less than 1:2); a second bag would contain oxyhemoglobin ($Fe^{II}$—$O_2$). The two solutions would be coinfused into a subject at ratios less than 1 part methemoglobin-nitrite to 1 part oxyhemoglobin. After and during the infusion, the oxyhemoglobin would deliver oxygen to the tissue as the oxygen delivery vehicle to form deoxyhemoglobin ($Fe^{II}$). Some of this would react with excess nitrite from the first bag to form NO. The methemoglobin-nitrite from that same bag would form an intermediate ($Fe^{II}$—$NO_2$ radical); this would react with NO to form $N_2O_3$ and $Fe^{II}$(deoxyhemoglobin). The $N_2O_3$ would vasodilate and restore NO homeostasis, and the deoxyhemoglobin would now be able to bind oxygen again in the lung. This system thus delivers oxygen, generates $N_2O_3$ and NO, and redox cycles to rebind oxygen in the lung.

Patient Recovery and Outcome Assessment

The physician can then assess the therapeutic efficacy of the cell-free hemoglobin based blood substitute detoxified by nitrite in increasing blood oxygenation in the human subject according to any of the methods disclosed above, or according to methods known to one skilled in the art, wherein a reduction of symptoms associated with hypoxia in the human subject indicates the effectiveness of the blood substitute in treating pathological blood deoxygenation in the subject.

In some embodiments, the human subject is treated with the cell-free hemoglobin based blood substitute detoxified by nitrite until the human subject exhibits relief from hypoxia, for example a lessening of one or more hypoxic symptoms or a cure, or inhibition of the development (for instance, prevention) of hypoxia. In such embodiments, treatment with the blood substitute can be discontinued at that point, or it can be continued to an endpoint according to the direction of a physician. It is also possible for the blood substitute to be administered to the human subject during the subject's surgical procedure, or following the surgical procedure. A physician uses methods known to one skilled in the art to assess vascular tone and blood oxygenation during the procedure and during the administration of the blood substitute. Blood substitute is administered according to a regime designed to restore and/or maintain a desirable vascular tone and level of blood oxygenation.

A unique aspect of adding nitrite or nitrite-methemoglobin to hemoglobin based blood substitutes is that the latter treatments (on their own) are associated with myocardial infarctions (heart attacks). Nitrite has potent effects at limiting myocardial infarction and will thus serve to limit this specific toxicity of the hemoglobin based blood substitutes. In addition, when nitrite or nitrite-methemoglobin are administered particularly in settings of civilian or military trauma with hemorrhage or organ injury, the cytoprotective effects of nitrite are expected to improve organ function and survival following resuscitation with hemoglobin-based blood substitutes.

This disclosure describes production of cell free blood substitutes. The disclosure further provides methods of preparing and using such compositions, as well as the advantages provided by compositions described herein. It will be apparent that the precise details of the methods described may be varied or modified without departing from the spirit of the described invention. We claim all such modifications and variations that fall within the scope and spirit of the claims below.

The invention claimed is:

1. A pharmaceutical composition, consisting essentially of a ferric ($Fe^{III}$) heme-containing molecule and nitrite, wherein the molar ratio of nitrite to the heme-containing molecule in the pharmaceutical composition is between about 1:2 and about 2:1.

2. The pharmaceutical composition of claim 1, wherein the ferric heme-containing molecule is hemoglobin.

3. The pharmaceutical composition of claim 1, wherein the ferric heme-containing molecule is methemoglobin.

4. The pharmaceutical composition of claim 1, wherein the ferric heme-containing molecule is cross-linked hemoglobin.

5. The pharmaceutical composition of claim 1, wherein the ferric heme-containing molecule is cross-linked methemoglobin.

6. The pharmaceutical composition of claim 1, wherein the ferric heme-containing molecule is a protein that binds oxygen.

7. The pharmaceutical composition of claim 1, wherein the molar ratio of nitrite to the ferric heme-containing molecule is greater than about 1:1.

8. The pharmaceutical composition of claim 1, wherein the molar ratio of nitrite to the ferric heme-containing molecule is less than about 1:1.

9. The pharmaceutical composition of claim 1, wherein the molar ratio of nitrite to the ferric heme-containing molecule is about 1:1.

10. The pharmaceutical composition of claim 1, further comprising a pharmaceutically acceptable carrier, an adjuvant, or a combination thereof.

11. A method of treating a subject having or predisposed to hypoxia, hypoxaemia, ischemia or anoxia, comprising administering to the subject a therapeutically effective amount of the pharmaceutical composition of claim 1, thereby treating the subject.

12. The method of claim 11, wherein the method is a method of replacing blood in a subject, comprising administering to the subject a therapeutically effective amount of the pharmaceutical composition of claim 1, thereby replacing blood in the subject.

13. The method of claim 11, wherein the subject has or is predisposed to anemia, bleeding disorder, trauma, injury, burn, coagulopathy, ectopic pregnancy, favism, gastrointestinal bleeding, hemolytic uremic syndrome, hemophilia, microcytosis, ulcer, bleeding in surgery, bleeding in pregnancy, hemorrhage, rhabdomyolysis, hemorrhagic shock, sickle cell anemia, hemoglobinopathy spherocytosis, thalassemia, and/or yellow fever.

14. The method of claim 11, wherein the subject has lost blood during a surgical procedure.

15. The method of claim 11, wherein the subject is a human.

16. The method of claim 11, wherein the subject is a non-human animal.

17. The method of claim 12, wherein the subject has or is predisposed to anemia, bleeding disorder, trauma, injury, burn, coagulopathy, ectopic pregnancy, favism, gastrointestinal bleeding, hemolytic uremic syndrome, hemophilia, microcytosis, ulcer, bleeding in surgery, bleeding in pregnancy, hemorrhage, rhabdomyolysis, hemorrhagic shock, sickle cell anemia, hemoglobinopathy spherocytosis, thalassemia, and/or yellow fever.

18. The method of claim 12, wherein the subject has lost blood during a surgical procedure.

19. The method of claim 12, wherein the subject is a human.

* * * * *